US011400052B2

(12) United States Patent
Walsh et al.

(10) Patent No.: US 11,400,052 B2
(45) Date of Patent: Aug. 2, 2022

(54) ALCOHOL-RESISTANT DRUG FORMULATIONS

(71) Applicant: Jazz Pharmaceuticals Ireland Limited, Dublin (IE)

(72) Inventors: Edwin Walsh, Dublin (IE); Clark Patrick Allphin, Seattle, WA (US)

(73) Assignee: Jazz Pharmaceuticals Ireland Limited, Dublin (IE)

( * ) Notice: Subject to any disclaimer, the term of this patent is extended or adjusted under 35 U.S.C. 154(b) by 2 days.

(21) Appl. No.: 16/688,797

(22) Filed: Nov. 19, 2019

(65) Prior Publication Data
US 2020/0330393 A1 Oct. 22, 2020

Related U.S. Application Data

(60) Provisional application No. 62/769,380, filed on Nov. 19, 2018, provisional application No. 62/769,382, filed on Nov. 19, 2018.

(51) Int. Cl.
*A61K 45/06* (2006.01)
*A61K 9/28* (2006.01)

(52) U.S. Cl.
CPC .......... *A61K 9/2866* (2013.01); *A61K 9/2846* (2013.01); *A61K 45/06* (2013.01)

(58) Field of Classification Search
CPC ..... A61K 9/2866; A61K 9/2846; A61K 45/06
See application file for complete search history.

(56) References Cited

U.S. PATENT DOCUMENTS

| | | |
|---|---|---|
| 3,051,619 A | 8/1962 | Laborit |
| 3,419,588 A | 12/1968 | De Man |
| 4,221,778 A | 9/1980 | Raghunathan |
| 4,374,441 A | 2/1983 | Carter et al. |
| 4,393,236 A | 7/1983 | Klosa |
| 4,510,128 A | 4/1985 | Khanna |
| 4,524,217 A | 6/1985 | Davenport et al. |
| 4,687,662 A | 8/1987 | Schobel |
| 4,738,985 A | 4/1988 | Kluger et al. |
| 4,916,161 A | 4/1990 | Patell |
| 4,939,949 A | 7/1990 | Langenberg |
| 4,983,632 A | 1/1991 | Gessa et al. |
| 5,294,430 A | 3/1994 | Borch et al. |
| 5,380,937 A | 1/1995 | Koehler et al. |
| 5,415,870 A | 5/1995 | Gergely et al. |
| 5,594,030 A | 1/1997 | Conte et al. |
| 5,753,708 A | 5/1998 | Koehler et al. |
| 5,758,095 A | 5/1998 | Albaum et al. |
| 5,833,599 A | 11/1998 | Schrier et al. |
| 5,840,331 A | 11/1998 | Van Cauter et al. |
| 5,845,255 A | 12/1998 | Mayuad |
| 5,955,106 A | 9/1999 | Moeckel et al. |
| 5,990,162 A | 11/1999 | Scharf |
| 6,014,631 A | 1/2000 | Teagarden et al. |
| 6,022,562 A | 2/2000 | Autant et al. |
| 6,067,524 A | 5/2000 | Byerly et al. |
| 6,112,182 A | 8/2000 | Akers et al. |
| 6,317,719 B1 | 11/2001 | Schrier et al. |
| 6,322,819 B1 | 11/2001 | Burnside et al. |
| 6,356,873 B1 | 3/2002 | Teagarden et al. |
| 6,384,020 B1 | 5/2002 | Flanner et al. |
| 6,436,998 B1 | 8/2002 | Cacciaglia et al. |
| 6,472,431 B2 | 10/2002 | Cook et al. |
| 6,472,432 B1 | 10/2002 | Perricone |
| 6,495,598 B1 | 12/2002 | Yoneda et al. |
| 6,565,872 B2 | 5/2003 | Wu et al. |
| 6,780,889 B2 | 8/2004 | Cook et al. |
| 7,015,200 B2 | 3/2006 | Mamelak et al. |
| 7,072,840 B1 | 7/2006 | Mayuad |
| 7,262,219 B2 | 8/2007 | Cook et al. |
| 7,568,822 B2 | 8/2009 | Ibrahim |
| 7,668,730 B2 | 2/2010 | Reardan et al. |

(Continued)

FOREIGN PATENT DOCUMENTS

| | | | |
|---|---|---|---|
| CA | 2 112 663 C | 4/2002 | |
| CA | 2510289 A1 * | 7/2004 | ............. A61K 45/06 |

(Continued)

OTHER PUBLICATIONS

Rujivipat et al., Improved drug delivery to the lower intestinal tract with tablets compression-coated with enteric/nonenteric polymer powder blends, Sep. 22, 2010, European Journal of Pharmaceutics and Biopharmaceutics, vol. 76, pp. 486-492 (Year: 2010).*
Thorpy, Update on Therapy for Narcolepsy, Apr. 9, 2015, Curr Treat Options Neurol, vo. 17, pp. 20-32 (Year: 2015).*
"HIB-IMUNE," Physicians Desk Reference (41st ed.), (1987), 1095-1096.
"HibVAX," Physicians Desk Reference (41st ed.), (1987), 870.
"Malic Acid," The Handbook of Pharmaceutical Excipients, 2nd Ed., (1994), pp. 285-286, 633.
"Phospholine Iodide," Physicians Desk Reference (50th ed.), (1996), 2784.

(Continued)

*Primary Examiner* — Ali Soroush

(74) *Attorney, Agent, or Firm* — Cooley LLP

(57) ABSTRACT

The invention relates to modified release oral formulations of therapeutic agents, including gamma hydroxybutyrate (GHB), paracetamol, codeine or oxycodone, which are resistant to alcohol induced dose dumping. Provided are formulations that have improved resistance to rapid release of the active ingredient in the presence of increasing amounts of alcohol. Also provided are formulations that can reduce or prevent the release of the active ingredient following exposure to alcohol-containing media. The invention also relates to methods of making the formulations, and methods of their use for the treatment of sleep disorders such as apnea, sleep time disturbances, narcolepsy, cataplexy, sleep paralysis, hypnagogic hallucination, sleep arousal, insomnia, and nocturnal myoclonus.

47 Claims, 35 Drawing Sheets

(56) References Cited

U.S. PATENT DOCUMENTS

| | | |
|---|---|---|
| 7,765,106 B2 | 7/2010 | Reardan et al. |
| 7,765,107 B2 | 7/2010 | Reardan et al. |
| 7,797,171 B2 | 9/2010 | Reardan et al. |
| 7,851,506 B2 | 12/2010 | Cook et al. |
| 7,895,059 B2 | 2/2011 | Reardan et al. |
| 8,101,209 B2 | 1/2012 | Legrand et al. |
| 8,193,211 B2 | 6/2012 | Liang et al. |
| 8,202,537 B2 | 6/2012 | Mehta et al. |
| 8,263,125 B2 | 9/2012 | Vaya et al. |
| 8,263,650 B2 | 9/2012 | Cook et al. |
| 8,324,275 B2 | 12/2012 | Cook et al. |
| 8,457,988 B1 | 6/2013 | Reardan et al. |
| 8,461,197 B2 | 6/2013 | Tung |
| 8,461,203 B2 | 6/2013 | Cook et al. |
| 8,529,954 B2 | 9/2013 | Lebon et al. |
| 8,589,182 B1 | 11/2013 | Reardan et al. |
| 8,591,922 B1 | 11/2013 | Allphin et al. |
| 8,598,191 B2 | 12/2013 | Liang et al. |
| 8,680,228 B2 | 3/2014 | Guo et al. |
| 8,731,963 B1 | 5/2014 | Reardan et al. |
| 8,759,394 B2 | 6/2014 | Tung et al. |
| 8,771,735 B2 | 7/2014 | Rourke et al. |
| 8,772,306 B1 | 7/2014 | Eller |
| 8,778,301 B2 | 7/2014 | Mamelak et al. |
| 8,778,398 B2 | 7/2014 | Rourke et al. |
| 8,859,619 B2 | 10/2014 | Cook et al. |
| 8,901,173 B2 | 12/2014 | Allphin et al. |
| 8,952,029 B2 | 2/2015 | Eller |
| 8,952,062 B2 | 2/2015 | Cook et al. |
| 9,023,400 B2 | 5/2015 | Guimberteau et al. |
| 9,050,302 B2 | 6/2015 | Eller |
| 9,132,107 B2 | 9/2015 | Allphin et al. |
| 9,486,426 B2 | 11/2016 | Eller |
| 9,539,330 B2 | 1/2017 | Cook et al. |
| 9,555,017 B2 | 1/2017 | Allphin et al. |
| 9,770,514 B2 | 9/2017 | Ghebre-Sellassie |
| 9,795,567 B2 | 10/2017 | Rourke et al. |
| 9,801,852 B2 | 10/2017 | Allphin |
| 10,195,168 B2 | 2/2019 | Allphin et al. |
| 10,213,400 B2 | 2/2019 | Eller |
| 10,272,062 B2 | 4/2019 | Mégret et al. |
| 10,398,662 B1 | 9/2019 | Allphin et al. |
| 10,736,866 B2 | 8/2020 | Mégret et al. |
| 10,758,488 B2 | 9/2020 | Allphin et al. |
| 10,813,885 B1 | 10/2020 | Allphin et al. |
| 10,925,844 B2 | 2/2021 | Grassot et al. |
| 10,952,986 B2 | 3/2021 | Megret et al. |
| 10,959,956 B2 | 3/2021 | Allphin et al. |
| 10,966,931 B2 | 4/2021 | Allphin et al. |
| 10,973,795 B2 | 4/2021 | Megret et al. |
| 10,987,310 B2 | 4/2021 | Allphin et al. |
| 11,077,079 B1 | 8/2021 | Allphin et al. |
| 11,090,269 B1 | 8/2021 | Allphin et al. |
| 11,147,782 B1 | 10/2021 | Allphin et al. |
| 2003/0180249 A1 | 9/2003 | Khanna et al. |
| 2004/0092455 A1 | 5/2004 | Mamelak et al. |
| 2005/0031688 A1 | 2/2005 | Ayala |
| 2005/0037077 A1 | 2/2005 | Legrand et al. |
| 2005/0113366 A1 | 5/2005 | Bourguignon et al. |
| 2005/0142192 A1 | 6/2005 | Benjamin et al. |
| 2006/0018933 A1 | 1/2006 | Vaya et al. |
| 2006/0024365 A1 | 2/2006 | Vaya et al. |
| 2006/0069040 A1 | 3/2006 | Mamelak |
| 2006/0078614 A1* | 4/2006 | Venkatesh ............ A61K 9/0056 424/469 |
| 2006/0210630 A1 | 9/2006 | Liang et al. |
| 2006/0228410 A1* | 10/2006 | Dumont ................ A61P 29/00 424/464 |
| 2007/0270491 A1 | 11/2007 | Cook et al. |
| 2008/0003267 A1 | 1/2008 | Spencer et al. |
| 2008/0069871 A1 | 3/2008 | Vaughn et al. |
| 2008/0085304 A1 | 4/2008 | Baichwal et al. |
| 2008/0118571 A1 | 5/2008 | Lee et al. |
| 2008/0226564 A1 | 9/2008 | Weers et al. |
| 2008/0292700 A1 | 11/2008 | Nghiem et al. |
| 2008/0293698 A1 | 11/2008 | Johnson |
| 2009/0137565 A1 | 5/2009 | Frucht |
| 2009/0155357 A1 | 6/2009 | Muhuri |
| 2009/0317355 A1 | 12/2009 | Roth et al. |
| 2010/0112056 A1 | 5/2010 | Rourke et al. |
| 2010/0266701 A1 | 10/2010 | Guimberteau et al. |
| 2011/0034727 A1 | 2/2011 | Luchi et al. |
| 2011/0039929 A1 | 2/2011 | Cook et al. |
| 2011/0091537 A1 | 4/2011 | Castan et al. |
| 2011/0111027 A1 | 5/2011 | Rourke et al. |
| 2011/0213004 A1* | 9/2011 | Kim ..................... A61P 3/06 514/381 |
| 2012/0020833 A1 | 1/2012 | Cook et al. |
| 2012/0076865 A1* | 3/2012 | Allphin ............ A61K 9/2866 424/495 |
| 2012/0148672 A1 | 6/2012 | Mehta et al. |
| 2012/0202879 A1 | 8/2012 | Cook et al. |
| 2012/0202880 A1 | 8/2012 | Cook et al. |
| 2013/0230587 A1 | 9/2013 | Pilgaonkar et al. |
| 2013/0273159 A1 | 10/2013 | Howard et al. |
| 2014/0004202 A1 | 1/2014 | Suplie et al. |
| 2014/0037745 A1 | 2/2014 | Liang et al. |
| 2014/0072624 A1* | 3/2014 | Jung .................... A61K 9/2081 424/451 |
| 2014/0093578 A1 | 4/2014 | Mehta et al. |
| 2014/0127306 A1 | 5/2014 | Mehta et al. |
| 2014/0141090 A1* | 5/2014 | Wilson ................ A61K 31/485 424/495 |
| 2014/0171506 A1 | 6/2014 | Allphin et al. |
| 2014/0271896 A1 | 9/2014 | Abu Shmeis et al. |
| 2014/0348917 A1 | 11/2014 | Rourke et al. |
| 2015/0005334 A1 | 1/2015 | Shah et al. |
| 2015/0073052 A1 | 3/2015 | Cook et al. |
| 2015/0328168 A1 | 11/2015 | Daviaud-Venet et al. |
| 2016/0068463 A1* | 3/2016 | Peoples ................ A61K 9/28 424/474 |
| 2016/0228379 A1 | 8/2016 | Kumar et al. |
| 2016/0271070 A1 | 9/2016 | Singh et al. |
| 2016/0338966 A1 | 11/2016 | Guimberteau et al. |
| 2016/0346200 A1 | 12/2016 | Sommer et al. |
| 2016/0346216 A1 | 12/2016 | Chen |
| 2017/0119627 A1 | 5/2017 | Bhargava et al. |
| 2017/0340519 A9 | 11/2017 | Bhargava et al. |
| 2018/0008539 A1 | 1/2018 | Singh et al. |
| 2018/0021284 A1 | 1/2018 | Mégret et al. |
| 2018/0042855 A1 | 2/2018 | Rourke et al. |
| 2018/0263936 A1 | 9/2018 | Allphin et al. |
| 2018/0318222 A1 | 11/2018 | Allphin et al. |
| 2019/0183806 A1 | 6/2019 | Guillard |
| 2019/0183836 A1 | 6/2019 | Mégret et al. |
| 2019/0269640 A1 | 9/2019 | Megret et al. |
| 2019/0269641 A1 | 9/2019 | Megret et al. |
| 2019/0274990 A1 | 9/2019 | Megret et al. |
| 2019/0282532 A1 | 9/2019 | Megret et al. |
| 2020/0113840 A1 | 4/2020 | Allphin et al. |
| 2020/0197347 A1 | 6/2020 | Megret et al. |
| 2020/0276142 A1 | 9/2020 | Grassot et al. |
| 2020/0360293 A1 | 11/2020 | Guillard |
| 2020/0360319 A1 | 11/2020 | Grassot et al. |
| 2020/0368187 A1 | 11/2020 | Grassot et al. |
| 2021/0121423 A1 | 4/2021 | Allphin et al. |
| 2021/0186907 A1 | 6/2021 | Skobieranda |

FOREIGN PATENT DOCUMENTS

| | | |
|---|---|---|
| CN | 102905688 A | 1/2013 |
| CN | 102958930 A | 3/2013 |
| CN | 103209966 A | 7/2013 |
| CN | 103209967 A | 7/2013 |
| EP | 0203768 A2 | 12/1986 |
| EP | 0235408 A1 | 9/1987 |
| EP | 0344704 A1 | 12/1989 |
| EP | 0616804 A1 | 9/1994 |
| EP | 0635265 A1 | 1/1995 |
| EP | 0709087 B1 | 12/1999 |
| EP | 0635265 B1 | 2/2000 |
| EP | 1140061 A2 | 10/2001 |
| EP | 1140061 B1 | 5/2003 |

(56) References Cited

FOREIGN PATENT DOCUMENTS

| | | | |
|---|---|---|---|
| EP | 1316309 A1 | 6/2003 | |
| EP | 2760911 B1 | 11/2017 | |
| EP | 1434572 B1 | 12/2017 | |
| GB | 922029 A | 3/1963 | |
| GB | 2295390 A | 5/1996 | |
| JP | S57-042651 A | 3/1982 | |
| JP | 62-12715 A | 1/1987 | |
| JP | 04-049212 A | 2/1992 | |
| JP | 05-508422 A | 11/1993 | |
| JP | H06-508839 A | 10/1994 | |
| JP | 7-53365 A | 2/1995 | |
| JP | H8-511257 A | 11/1996 | |
| JP | 09-104620 A | 4/1997 | |
| JP | H10-505604 A | 6/1998 | |
| JP | 2001-513552 A | 9/2001 | |
| JP | 2002-533388 A | 10/2002 | |
| JP | 2004-514732 A | 5/2004 | |
| JP | 2007-521231 A | 8/2007 | |
| JP | 2008-512386 A | 4/2008 | |
| JP | 2008-519847 A | 6/2008 | |
| JP | 2008-528571 A | 7/2008 | |
| JP | 2009-532331 A | 9/2009 | |
| JP | 2011-500865 A | 1/2011 | |
| JP | 2012-507532 A | 3/2012 | |
| RU | 2210360 C1 | 8/2003 | |
| WO | WO 1994/028880 A1 | 12/1994 | |
| WO | WO 1996/040105 A1 | 12/1996 | |
| WO | WO 1999/009972 A1 | 3/1999 | |
| WO | WO 2000/038672 A2 | 7/2000 | |
| WO | WO 2002/045684 A2 | 6/2002 | |
| WO | WO 2005/016318 A1 | 2/2005 | |
| WO | WO-2005030174 A1 * | 4/2005 | ........... A61K 9/1635 |
| WO | WO 2005/099671 A2 | 10/2005 | |
| WO | WO 2006/029155 A2 | 3/2006 | |
| WO | WO 2006/053186 A2 | 5/2006 | |
| WO | WO 2006/080029 A1 | 8/2006 | |
| WO | WO 2007/053698 A2 | 5/2007 | |
| WO | WO 2007/103200 A2 | 9/2007 | |
| WO | WO 2008/086804 A2 | 7/2008 | |
| WO | WO 2009/056550 A2 | 5/2009 | |
| WO | WO 2010/053691 A1 | 5/2010 | |
| WO | WO 2010/055260 A1 | 5/2010 | |
| WO | WO 2011/119839 A1 | 9/2011 | |
| WO | WO 2011/127252 A2 | 10/2011 | |
| WO | WO 2011/135461 A2 | 11/2011 | |
| WO | WO 2011/139271 A1 | 11/2011 | |
| WO | WO 2011/140310 A2 | 11/2011 | |
| WO | WO 2012/028688 A1 | 3/2012 | |
| WO | WO 2012/107652 A1 | 8/2012 | |
| WO | WO 2014/078014 A2 | 5/2014 | |
| WO | WO 2015/120006 A1 | 8/2015 | |
| WO | WO 2015/120110 A2 | 8/2015 | |
| WO | WO 2016/087952 A1 | 6/2016 | |
| WO | WO 2016/178132 A1 | 10/2016 | |
| WO | WO 2015/166473 A1 | 3/2017 | |
| WO | WO 2017/147375 A1 | 8/2017 | |
| WO | WO 2017/182851 A1 | 10/2017 | |
| WO | WO 2018/015563 A1 | 1/2018 | |
| WO | WO 2019/123269 A1 | 6/2019 | |
| WO | WO 2020/178695 A1 | 9/2020 | |
| WO | WO 2021/168403 A1 | 8/2021 | |

OTHER PUBLICATIONS

"Taxotere," Physicians Desk Reference (51st ed.), (1997), 2204-2207.
21 C.F.R. 184, Food and Drug Administration, HHS, (1998), pp. 441-535.
Activase, Physicians Desk Reference (50th ed.), (1996), pp. 312, 1058-1061.
Akifuddin et al. "Preparation, characterization and in-vitro evaluation of microcapsules for controlled release of Diltiazem hydrochloride by Ionotropic gelation technique." Journal of Applied Pharmaceutical Science (2013); 3.4: 35-42.
Anand et al. "Ion-exchange resins: carrying drug delivery forward." Drug Discovery Today (2001); 6.17: 905-914.
Baldrick, P., "Pharmaceutical Excipient Development: The Need for Preclinical Guidance," Regul. Toxicol. Pharmacol. Oct. 2000 32(2):210-218.
Bedard, "Nocturnal γ-Hydroxybutyrate—Effect on Periodic Leg Movements and Sleep Organization of Narcoleptic Patients," Clin Neuropharmacol., 12(1), Feb. 1989, 29-36.
Berner, Jon E., "A Case of Sodium Oxybate Treatment of Tardive Dyskinesia and Bipolar Disorder," J. Clin. Psychiatry, 2008, 69:5, p. 862.
Berthier, et al., "Possible Involvement of a Gamma-Hydroxybutyric Acid Receptor in Startle Disease," Acta Paediatr, 83, 1994, 678-680.
Bodmeier, R., "Tableting of coated pellets," European Journal of Pharmaceutics and Biopharmaceutics, (1997) 43(1), 1-8.
Borgen et al., "The influence of gender and food on the pharmacokinetics of sodium oxybate oral solution in healthy subjects." J Clin Pharmacol. (2003); 43(1): 59-65.
Borgen, L., et al. "Xyrem® (sodium oxybate): A Study of Dose Proportionality in Healthy Human Subjects." J. Clin. Pharmacol. (2000); 40: 1053.
Broughton et al., "The Treatment of Narcolepsy-Cataplexy with Nocturnal Gamma-Hydroxybutyrate." Can J. Neural Sci (1979); 6(1): 1-6.
Broughton, et al. "Effects of Nocturnal Gamma-Hydroxybutyrate on Spell/Waking Patterns in Narcolepsy-Cataplexy." Can J. Neural Sci (1980); 7 (1): 23-31.
Broughton, et al. "Gamma-Hydroxy-Butyrate in the Treatment of Narcolepsy: a Preliminary Report." (1976) Narcolepsy, Ny, N.Y., Spectrum Publications, Inc. 659-668.
Caballero et al. "Characterization of alginate beads loaded with ibuprofen lysine salt and optimization of the preparation method." International Journal of Pharmaceutics (2014); 460.1: 181-188.
Chem Abstract ES302338, SciFinder®, (1964), 1 pg.
Chemical Abstracts: Seventh Collective Index, vols. 56-65, (1962-1966), 4 pgs.
Davis et al. "Active chloride secretion in the normal human jejunum." J Clin Invest. (1980); 66(6): 1326-1333.
Ferrara, S. D., et al., "Pharmacokinetics of Y-Hydroxybutyric Acid in Alcohol Dependent Patients After Single and Repeated Oral Doses." Br. J. Clin. Pharmacol. (1992); 34: 231-235.
Ferris, T.J., et al., "Synthesis, characterisation and detection of gamma-hydroxybutyrate salts," Forensic Science International, 2012, 216: 158-162.
Frucht, et al. "A pilot Tolerability and Efficacy Trial of Sodium Oxybate in Ethanol-Responsive Movement Disorders." Movement Disorders (2005); 20 (10): 1330-1337.
Frucht, S.J., et al., "A Single-Blind, Open-Label Trial of Sodium Oxybate for Myoclonus and Essential Tremor," Neurology (2005); 65 (12): 1967-1970.
Gallimberti, L., "Gamma-hydroxybutyric Acid for Treatment of Alcohol Withdrawal Syndrome," The Lancet, 2(8666), (1989), 787-789.
Gallimberti, L., "Gamma-Hydroxybutyric Acid in the Treatment of Alcohol Dependence: A Double-Blind Study," Alcohol Clin. Exp. Res. (1992), 16(4): 673-676.
Gallimberti et al., "Clinical efficacy of gamma-hydroxybutyric acid in treatment of opiate withdrawal," Eur Arch Psychiatry Clin Neurosci. 1994;244(3):113-114.
Gallimberti et al., "Gamma-Hydroxybutyric Acid for Treatment of Opiate Withdrawal Syndrome," Neuropsychopharmacology, 1993, vol. 9, No. 1, pp. 77-81.
Gerra, G., et al., "Flumazenil effects on growth hormone response to gamma-hydroxybutyric acid," Int Clin Psychopharmacol. (1994); 9 (3): 211-215.
Gessa, G. L., "Gamma-hydroxybutyric Acid in the Treatment of Alcohol Dependence," Clin. Neuropharm., vol. 15 Suppl. 1, Pt A, (1992), 303a-304a.
Gessa, G. L., et al., "Gamma-hydroxybutyric acid (GHB) for treatment of ethanol dependence," European Neuropsychopharmacology, 3(3), (1993), 224-225.

(56) References Cited

OTHER PUBLICATIONS

Grove-White, I. G., "Critical Flicker Frequency after Small Doses of Methohexitone, Diazepam and Sodium 4-Hydroxybutyrate." Brit. J. Anaesth (1971); 43 (2): 110-112.
Grove-White, I. G., et al., "Effect of Methohexitone, Diazepam and Sodium 4-Hydroxybutyrate on Short-Term Memory." Brit. J. Anaesth (1971); 43 (2): 113-116.
Hasenbos, M.A., et al., "Anaesthesia for bullectomy. A technique with spontaneous ventilation and extradural blockade." Anaesthesia (1985); 40 (10): 977-980.
Hoes, M. J., "Gamma-hydroxybutyric acid (*) as hypnotic. Clinical and pharmacokinetic evaluation of gammahydroxybutyric acid as hypnotic in man," L'Encéphale: Revue de psychiatrie clinique biologique et thérapeutique (1980); 6 (1): 93-99.
Laborit, H., "Gamma-Hydroxybutyrate, Succinic Semialdehyde and Sleep," Laboratoire d'Eutonologie, (1973), 257-274.
Ladinsky, H., et al., "Mode of Action of Gamma-Butyrolactone on the Central Cholinergic System, Naunyn-Schmiedeberg's," Arch. Pharmacol. (1983); 322 (1): 42-48.
Lammers, G. J., "Gammahydroxybutyrate and Narcolepsy: A Double-Blind Placebo-Controlled Study." Sleep (1993); 16 (3): 216-220.
Lapierre et al., "The Effect of Gamma-Hydroxybutyrate: A Double-Blind Study of Normal Subjects," Sleep Research (1988); 17:99, 1988, 6 pages. (Abstract Only).
Lapierre, O., "The Effect of Gamma-Hydroxybutyrate on Nocturnal and Diurnal Sleep of Normal Subjects: Further Considerations on REM Sleep-Triggering Mechanisms." Sleep (1990); 13 (1): 24-30.
Lee, C. R., "Evidence for the β-oxidation of orally administered 4-hydroxybutyrate in humans." Biochemical Medicine (1977); 17 (3): 284-291.
Lubrano, et al. "Fibromyalgia in Patients with Irritable Bowel Syndrome. An Association with the Severity of the Intestinal Disorder." Int J Colorectal Dis. (2001); 16 (4): 211-215.
Mahore et al. "Ion exchange resins: pharmaceutical applications and recent advancement." Int J Pharm Sci Rev Res (2010); 1.2: 8-13.
Mamelak, et al. The Effects of γ-Hydroxybutyrate on Sleep. Biol Psych (1977); 12 (2): 273-288.
Mamelak, M., "Gammahydroxybutyrate: An endogenous regulator of energy metabolism." Neuroscience and Biobehavioral Reviews (1989); 13 (4): 187-198.
Mamelak, M., "Sleep-Inducing Effects of Gammahydroxybutyrate." The Lancet (1973); 302 (7824): 328-329.
Mamelak, M., et al., "Treatment of Narcolepsy and Sleep Apnea with Gammahydroxybutyrate: A clinical and polysomnographic case study." Sleep (1981); 4 (1): 105-111.
Mamelak, M., et al., "Treatment of Narcolepsy with γ-hydroxybutyrate. A review of Clinical and Sleep Laboratory Findings." Sleep (1986); 9 (1): 285-290.
Moldofsky et al. "A Chronobiologic Theory of Fibromyalgia." J. Muscoloskel. Pain, 1, 49 (1993).
Moldofsky, et al. "Musculoskeletal Symptoms and Non-REM Sleep Disturbance in Patients with 'Fibrositis Syndrome' and Healthy Subjects." Psychosom. Med. (1975); 37 (4): 341-351.
Morrison, Robert Thornton, et al., Organic Chemistry, 3rd Edition, (1973), pp. 672-677.
Nema, S, et al., "Excipients and Their Use in Injectable Products." PDA J. Pharm. Sci. Technol. (1997); 51(4): 166-171.
Neuman, Ariel, "GHB's Path to Legitimacy: An Administrative and Legislative History of Xyrem." Apr. 2004, Harvard Law School, Class of 2005, Food and Drug Law, Winter Term 2004, Professor Peter Barton Hutt. (2004), 1-39.
Ohta et al. "Development of a simple method for the preparation of a silica gel based controlled delivery system with a high drug content." European Journal of Pharmaceutical Sciences (2005); 26.1: 87-96.
Ondo, William G., et al., "Sodium Oxybate for Excessive Daytime Sleepiness in Parkinson's Disease: A Polysomnographic Study." Arch. Neural. (2008); 65 (10): 1337-1340.
Order, filed Sep. 14, 2012, in the case of *Jazz Pharmaceuticals, Inc.*, Plaintiff, v. *Roxane Laboratories, Inc.*, Defendant (United States District Court for the District of New Jersey, Civil 10-6108 ES), (Sep. 14, 2012).
Outlaw, et al. "Dyspepsia and its Overlap with Irritable Bowel Syndrome." Curr Gastroenterol Rep. (2006); 8 (4): 266-272.
Palatini, P., "Dose Dependent Absorption and Elimination of Gamma-Hydroxybutyric Acid in Healthy Volunteers." Eur. J. Clin. Pharmacol. (1993); 45 (4): 353-356.
Patil et al. "A review on ionotropic gelation method: novel approach for controlled gastroretentive gelispheres." International Journal of Pharmacy and Pharmaceutical Sciences (2012); 4.4: 27-32.
Puguan et al. "Diffusion characteristics of different molecular weight solutes in Ca—alginate gel beads." Colloids and Surfaces A: Physicochemical and Engineering Aspects (2015); 469: 158-165.
Remington. The Science and Practice of Pharmacy. 20th Edition, Gennaro, Ed,. Lippincott Williams & Wilkins (2000). (See e.g. p. 861).
Remington. The Science and Practice of Pharmacy. 20th Edition, Gennaro, Ed,. Lippincott Williams & Wilkins. Chapter 45 (Oral Solid Dosage Forms) (2000).
Rohm and Haas. "Duolite AP143/1083 Pharmaceutical Grade Anion Exchange Resin." Feb. 2006, 4 pages.
Roth, et al., "γ-Butyrolactone and γ-Hydroxybutyric Acid-I, Distribution and Metabolism." Biochemical Pharmacology (1966); 15 (9):1333-1348.
Roth, R. H., et al., "γ-Butyrolactone and .gamma.-Hydroxybutyric acid-II. The Pharmacologically active form." J. Neuropharmacol. (1966); 5 (6): 421-428.
Roxane Laboratories, Inc.'s Answer and Affirmative Defenses to Plaintiff's Complaint, (Jan. 4, 2013).
Roxane Laboratories, Inc.'s Answer, Affirmative Defenses and Counterclaims to Plaintiff's Complaint, (Dec. 29, 2010).
Roxane Laboratories, Inc.'s Answer, Affirmative Defenses and Counterclaims to Plaintiff's Complaint, (Jun. 1, 2011).
Roxane Laboratories, Inc.'s Answer, Affirmative Defenses and Counterclaims to Plaintiff's Complaint, (Mar. 9, 2011).
Roxane Laboratories, Inc.'s Answer, Affirmative Defenses and Counterclaims to Plaintiff's Complaint, (Nov. 9, 2012).
Roxane Laboratories, Inc.'s Initial Invalidity and Noninfringement Contentions Pursuant to Local Patent Rule 3.6, (Apr. 14, 2011).
Rubbens et al., "Gastric and Duodenal Ethanol Concentrations after intake of Alcoholic Beverages in Postprandial Conditions," Molecular Pharmaceutics, (2017) 14(12):4202-4208.
Russell, I. Jon, et al., "Sodium Oxybate Relieves Pain and Improves Function in Fibromyalgia Syndrome." Arthritis. Rheum. (2009); 60 (1): 299-309.
Scharf, et al., "Effect of Gamma-Hydroxybutyrate on Pain, Fatigue, and the Alpha Sleep Anomaly in Patients with Fibromyalgia," (1998) J. Rheumatol. (1998) 25:1986-1990.
Scharf, M. B., "The Effects and Effectiveness of γ-Hydroxybutyrate in Patients with Narcolepsy." J. Clin. Psychiatry (1985); 46 (6): 222-225.
Scharf, M. B., et al., "GHB—New Hope for Narcoleptics?" Biol Psychiatry (1989); 26 (4): 329-330.
Scharf, Martin B., et al., "The Effects of Sodium Oxybate on Clinical Symptoms and Sleep Patterns in Patients with Fibromyalgia." J. Rheumatol. (2003); 30 (5): 1070-1074.
Scrima, et al., "Effect of Gamma-Hydroxybutyrate on a Patient with Obstructive Sleep Apnea." Sleep Research (1987); 16: 137.
Scrima, et al., "Effect of High Altitude on a Patient with Obstructive Sleep Apnea." Sleep Research (1987); 16: 427.
Scrima, et al., "Effects of Gamma-Hydroxybutyrate (GHB) on Narcolepsy-Cataplexy Symptoms and MSLT Results in Male and Female Patients." Association of Professional Sleep Societies (1988); 251.
Scrima, et al., "Gamma-Hydroxybutyrate Effects on Cataplexy and Sleep Attacks in Narcoleptics." Sleep Research (1987); 16: 134.
Scrima, L., "The Effects of γ-Hydroxybutyrate on the Sleep of Narcolepsy Patients: A Double-Blind Study." Sleep (1990); 13 (6): 479-490.

(56) References Cited

OTHER PUBLICATIONS

Scrima, L., et al., "Efficacy of Gamma-Hydroxybutyrate Versus Placebo in Treating Narcolepsy-Cataplexy: Double-Blind Subjective Measures," Biol. Psychiatry (1989); 26 (4): 331-343.

Scrima, L., et al., "Narcolepsy." New England J. Med. (1991); 324 (4): 270-272.

Seno and Yamabe. "The Rheological Behavior of Suspensions of Ion-exchange Resin Particles." Bulletin of the Chemical Society of Japan (1966); 39.4: 776-778.

Series, F., "Effects of Enhancing Slow-Wave Sleep by Gamma-Hydroxybutyrate on Obstructive Sleep Apnea." Am. Rev. Respir. Dis. (1992); 145 (6): 1378-1383.

Shah et al., "In vitro Dissolution Profile Comparison—Statistics and Analysis of the Similarity Factor, f2," Pharm Research, (1998) 15(6):889-896.

Singh et al. "Ion exchange resins: drug delivery and therapeutic applications." Fabad J. Pharm. Sci (2007); 32: 91-100.

Snead, et al., "Ontogeny of γ-Hydroxybutyric Acid. I. Regional Concentration in Developing Rat, Monkey and Human Brain." Brain Res. (1981); 227 (4): 579-589.

Snead, O. Carter, "γ-Hydroxybutyrate Model of Generalized Absence Seizures: Further Characterization and Comparison with Other Absence Models." Epilepsia (1988); 29 (4): 361-368.

Srikanth et al., "Ion-exchange resins as controlled drug delivery carriers." Journal of Scientific Research (2010); 2.3: 597-611.

Stock, G., "Increase in brain dopamine after axotomy or treatment with Gammahydroxybutyric acid due to elimination of the nerve impulse flow." Naunyn-Schmiedeberg's Arch. Pharmacol. (1973); 278 (4): 347-361.

Strong, A.J., "γ-Hydroxybutyric acid and intracranial pressure." The Lancet (1984); 1 (8389): 1304.

Suner, Selim, et al., "Pediatric Gamma Hydroxybutyrate Intoxication." Acad Emerg. Med. (1997); 4 (11): 1041-1045.

Takka and Gürel. "Evaluation of chitosan/alginate beads using experimental design: formulation and in vitro characterization." AAPS PharmSciTech (2010); 11.1: 460-466.

Transcript of a Markman Hearing, dated Apr. 26, 2012, in the case of *Jazz Pharmaceuticals, Inc.*, Plaintiff, v. *Roxane Laboratories, Inc.*, Defendant (United States District Court for the District of New Jersey, Civil 106108 ES), (Apr. 26, 2012).

Tunnicliff, Godfrey, "Sites of Action of Gamma-Hydroxybutyrate (GHB)—A Neuroactive Drug with Abuse Potential." Clinical Toxicology (1997); 35 (6): 581-590.

Turnberg, L.A. "Abnormalities in intestinal electrolyte transport in congenital chloridorrhoea." Gut. (1971); 12(7): 544-551.

U.S. Department of Health and Human Services et al., "Dissolution Testing of Immediate Release Solid Oral Dosage Forms," Food and Drug Administration, CDER, Aug. 1997, 17 pages.

U.S. Department of Health and Human Services et al., "Extended Release Oral Dosage Forms: Development, Evaluation, and Application of In Vitro/In Vivo Correlations", Food and Drug Administration, CDER, Sep. 1997, 27 pages.

United States Pharmacopeial Convention, Inc.: The National Formulary, 23/NF18, (1995), p. 2205.

Unknown author, title: definition of biotransformation; Medical dictionary; downloaded Jun. 21, 2018 (Year: 2018), 3 pages.

Van Den Bogert, A. G., et al., "Placentatransfer of 4-hydroxybutyric acid in man," Anaesthesiology and Intensive Care Medicine (1978); 110: 55-64.

Vickers, M.D., "Gammahydroxybutyric Acid." Int. Anesth. Clinic (1969); 7 (1): 75-89.

Walden et al., "The Effect of Ethanol on the Release of Opioids 30 from Oral Sustained-Release Preparations," Drug Development and Industrial Pharmacy, 2007, 33:10, 1101-1111.

Wermuth (Ed.), The Practice of Medicinal Chemistry, Academic Press, Third Edition, "Preparation of Water-Soluble Compounds Through Salt Formulation," Chapter 37, 2008, p. 758, 6 pages.

World Health Organization, "Annex 7: Multisource (generic) pharmaceutical products: guidelines on registration requirements to establish interchangeability," WHO Expert Committee on Specifications for Pharmaceutical Preparations Fortieth Report, pp. 347-390, 2006, retrieved from http://apps.who.int/prequal/info_general/documents/TRS937/WHO_TRS_937_eng.pdf#page=359.

Yamada, Y., "Effect of Butyrolactone and Gamma-Hydroxybutyrate on the EEG and Sleep Cycle in Man," Electroencephalography and Clinical Neurophysiology (1967); 22 (6): 558-562.

Zheng (Ed.), "Formulation and Analytical Development for Low-Dose Oral Drug Products," John Wiley & Sons, Inc., Hoboken, New Jersey, Table 4.1, p. 65, 2009, 3 pages.

International Search Report and Written Opinion of the International Searching Authority for International Application No. PCT/US2019/062237, dated Mar. 31, 2020, 11 pages.

Alshaikh et al., "Sodium Oxybate for Narcolepsy with Cataplexy: Systematic Review and Meta-Analysis," Journal of Clinical Sleep Medicine, 2012, vol. 8, No. 4, 451-458.

Chen et al, "harmacokinetics, relative bioavailability and food effect of JZP-258 and sodium oxybate: results of two phase 1, open-label, randomised crossover studies in healthy volunteers," Sleep Medicine, Abstracts, 2019, vol. 64, pp. S65-S66.

Erowid, "Gamma-hydroxybutyrate (GHB) Basic Synthesis Procedure," http://www.erowid.org/chemicals/ghb/ghb_synthesis.shtml (as downloaded on Aug. 8, 2013) 2 pages.

Fides, "Solutions of 4-hydrox-ybutyric acid salts for injection," Chem Abstract ES302338. Laboratorio M. Cuatecases, S.A., 2011. pp. 2.

Geekwench et al., "Title: Does anyone know why Jazz choose to make sodium oxybate?", Sep. 14, 2010; downloaded from http://www.talkaboutsleep.com/message/boards/topic/does-anybody-know-why-jazz-chose-to-make-sodium-oxybate/#sthash.no0PSCkL.dpuf on Jan. 21, 2015.

Geek Wench et al., "Title: Does anyone know why Jazz choose to make sodium oxybate?", Sep. 14, 2010: downloaded from http://www.talkaboutsleep.com/message-boards/topic/docs-anybody-know-why-jazz-chose-to-make-sodium-oxybate/ on Nov. 13, 2017 (30 pages).

International Search Report and Written Opinion of the International Searching Authority for International Application No. PCT/US2020/066561, dated Apr. 13, 2021, 12 pages.

International Search Report and Written Opinion of the International Searching Authority for International Application No. PCT/US2021/019024, dated Jun. 2, 2021, 10 pages.

International Searching Authority, "International Search Report, dated Apr. 15, 2014, for International Patent Application No. PCT/US2013/074954" 3 pages.

International Searching Authority, "Written Opinion, dated Apr. 15, 2014, for International Patent Application No. PCT/US2013/074954" 8 pages.

International Searching Authority, International Search Report and Written Opinion, dated Jun. 27, 2018 for International Patent Application No. PCT/EP2018/056745 (12 pages).

International Searching Authority, International Search Report for International Application Serial No. PCT/US99/30740, dated Jul. 21, 2000, 1 pg.

Jazz Pharmaceuticals, "Jazz Pharmaceuticals Announces Positive Top-line Results from Phase 3 Study of JZP-258 in Adult Narcolepsy Patients with Cataplexy and Excessive Daytime Sleepiness," Mar. 26, 2019, 2 pages, retrieved from https://investor.jazzpharma.com/node/16206/pdf.

Jazz Pharmaceuticals, Inc., "Xyrem.RTM. (sodium oxybate) oral solution Prescribing Information," Xyrem® US Package Insert available at http://pp.jazzpliamia.com/pi/xyem.en.USPI.pdf (downloaded Sep. 12, 2017, 32 pages).

Jha, M.K, "Modified release formulations to achieve the quality target product profile (Qtpp)," I Jpsr, 2012; vol. 3(8): 2376-2386.

Keating, GM, "Sodium Oxybate: A Review of Its Use in Alcohol Withdrawal Syndrome and in the Maintenance of Abstinence in Alcohol Dependence," Clinical Drug Investigation (2014) 34, 63-80.

Khediri et al., "Efficacy of Diosmectite (Smecta)® in the Treatment of Acute Watery Diarrhea in Adults: A Multicenter, Randomized, Double-Blind, Placebo-Controlled, Parallel Group Study," Hindawi Publishing Corporation, Gastroenterology Research and Practice, 2011, vol. 2011, Article ID 783196, 8 pages.

(56) References Cited

OTHER PUBLICATIONS

Leu-Semenescu et al., "Benefits and risk of sodium oxybate in idiopathic hypersomnia versus narcolepsy type 1: a chart review," Sleep Medicine, Jan. 2016, vol. 17, pp. 38-44.
Luhn, O., "Using Excipients in Powder Formulations," Pharmaceutical Technology Europe, Jan. 7, 2011, vol. 23, Issue 1, 6 pages, retrieved from https://www.pharmtech.com/view/using-excipients-powder-formulations.
Medicines for Children, "Oral Rehydration Salts," Leaflet information published Jul. 25, 2013, by Neonatal and Paediatric Pharmacists Group (NPPG), 6 pages, retrieved from https://www.medicinesforchildren.org.uk/oral-rehydration-salts.
Morrison, Robert T., et al., "Organic Chemistry", Chapter 20: "Functional Derivatives of Carboxylic Acids," 3rd Edition, 1973, pp. 658-700.
Parmar et al., "Clinical Characteristics of Cataplectic Attacks in Type 1 Narcolepsy," Current Neurology and Neuroscience Reports (2020) 20:38, 9 pages.
Rohm and Haas, "AMBERLITE® IRN78 Industrial Nuclear Grade Strong Base Anion Resin," 2000, PDS 0547—Jan. 1998, 2 pages.
Thorpy, M.J., "Recently Approved and Upcoming Treatments for Narcolepsy," CNS Drugs (2020) 34:9-27.
Vogel et al., 2018, "Toxicologic/transport properties of NCS-382, a γ-hydroxybutyrate (GHB) receptor ligand, in neuronal and epithelial cells: Therapeutic implications for SSADH deficiency, a GABA metabolic disorder," Toxicol In Vitro, 46:203-212 (Epub 2017).
Allphin, C., Declaration under 37 C.F.R. § 1.132 filed in U.S. Appl. No. 16/025,487 on Mar. 6, 2020, 7 pages.

\* cited by examiner

ALCOHOL-RESISTANT DRUG FORMULATIONS

RELATED APPLICATIONS

This application claims priority from U.S. application Ser. No. 62/769,380 filed Nov. 19, 2018 and U.S. application Ser. No. 62/769,382 filed Nov. 19, 2018, each of which is incorporated herein by reference in its entirety.

FIELD OF THE INVENTION

The present invention relates to modified release formulations of therapeutic agents such as gamma hydroxybutyrate (GHB or oxybate), paracetamol, opioids or opiates that are resistant to alcohol-induced dose dumping. The invention is particularly applicable to therapeutic agents whereby there is a serious clinical consequence of an alcohol induced dose dumping event (e.g. GHB, paracetamol, codeine or oxycodone). The invention also relates to methods for safely administering such therapeutic agents (e.g. GHB, paracetamol, codeine or oxycodone), methods of making the formulations, and methods of their use for the treatment of sleep disorders such as apnea, sleep time disturbances, narcolepsy, cataplexy, sleep paralysis, hypnagogic hallucination, sleep arousal, insomnia, and nocturnal myoclonus.

BACKGROUND OF THE INVENTION

"Dose dumping" refers to the unintended, rapid release of a drug contained in a dosage form within a short period of time. Dose dumping poses a significant risk to patients because of safety issues and/or diminished efficacy, particularly in oral dosage forms where the active drug may be present in relatively high amounts and especially when it is intended to release the drug slowly. Many modified release oral dosage forms are vulnerable to "alcohol-induced dose dumping" which, depending on the drug being "dumped", can also cause serious side effects.

Certain drugs, including GHB (commercially sold as Xyrem®), may cause respiratory depression or distress or changes in alertness if large amounts are released due to dose dumping. The FDA requires strict Important Safety Information to be provided with such medicines and which must clearly outline that one should not drink alcohol when taking these drugs. The onus thus falls on the user to regulate the timing of their alcohol consumption in comparison to when they take the drug. As alcohol is known to impair judgement, it runs the risk that someone who is intoxicated may still ingest these types of agents even after consuming significant amounts of alcohol. Thus there is a need for modified release formulations that can prevent or delay the release of such drugs in the presence of alcohol which is either intentionally or accidentally co-ingested.

Development of modified release oral dosage forms have been studied for many years and they often use multiple release-rate-controlling mechanisms. Typical release-rate-controlling mechanisms include swellable polymers, gel matrixes and polymeric coatings.

The problem of dose dumping in the presence of alcohol has not yet been satisfactorily resolved. Accordingly, there exists a need in the art to provide modified release oral dosage forms which have reduced potential for alcohol induced dose dumping, particularly at increasing concentrations of alcohol. The inventors have surprisingly found that by coating a drug-containing core with a specific mixture of polymers, normal release of the drug occurs when exposed to low levels of alcohol; however, drug release is rapidly and significantly reduced as the amount of alcohol increases.

SUMMARY OF THE INVENTION

The present invention overcomes deficiencies in the prior art by providing drug compositions that are resistant to alcohol induced dose dumping. One embodiment of a drug is gamma-hydroxybutyrate (GHB) or a salt thereof. Other embodiments are drugs used for mild, moderate and/or severe pain, including paracetamol, opioids or opiates. In certain embodiments the opioid or opiate is selected from codeine, morphine, methadone, buprenorphine, hydrocodone or oxycodone. Compositions of the invention can also suppress the release of these drugs following exposure to alcohol and have adjusted drug product dissolution properties when the composition is exposed to increasing concentrations of alcohol. One embodiment of the present invention also provides methods to treat a number of conditions treatable by GHB, paracetamol, an opioid and/or opiate referred to herein as "therapeutic categories." Therapeutic categories for the present invention include, but are not limited to, sleeping disorders, drug abuse, alcohol and/or opiate withdrawal, a reduced level of growth hormone, anxiety, analgesia (including the treatment of mild, moderate and/or severe pain; including acute, chronic, breakthrough, somatic, visceral or neuropathic pain), effects in certain neurological disorders, such as Parkinson's Disease, depression, certain endocrine disturbances and tissue protection following hypoxia/anoxia such as in stroke or myocardial infarction, or an increased level of intracranial pressure or other conditions treatable with GHB, paracetamol, an opioid or opiate. Prevention of alcohol induced dose dumping is particularly pertinent for alcohol, opioid and/or opiate withdrawal.

One embodiment of the invention is an oral formulation with increased resistance to alcohol-mediated dissolution comprising at least one population of drug carrier cores comprising at least one therapeutic agent; wherein said core is coated with one or more functional coatings; and wherein said one or more functional coatings comprises a polymer blend of cellulose polymers and polymethacrylates. In some embodiments, the drug carrier core comprises granules, nanoparticles, micro-particles, beads, pellets, mini-tablets, tablets and/or capsules (hard and/or soft gelatin), or a combination thereof. In other embodiments, the drug carrier core comprises drug crystals. Smaller drug carrier cores or drug crystals may see thicker film coats due to higher surface area and substantially thicker gel layers in the presence of ethanol. In some embodiments, the drug carrier core can be the size and/or shape of a pellet, bead, mini-tablet or tablet.

In some embodiments, the polymer blend comprises ethyl cellulose and a polymethacrylate. In certain embodiments, the ethyl cellulose and a polymethacrylate polymer are present at a weight ratio of ethyl cellulose:polymethacrylate polymer from 50:1 to 1:50, 25:1 to 1:25, 10:1 to 1:10, 5:1 to 1:5 or 3:1 to 1:3. In specific embodiments, the ethyl cellulose and a polymethacrylate polymer are present at a weight ratio of ethyl cellulose:polymethacrylate polymer from 3:1 to 1:3. In other embodiments, the ethyl cellulose and a polymethacrylate polymer are present at a weight ratio of ethyl cellulose:polymethacrylate polymer from 3:1 to 1:3, 2:1 to 1:2, or 1:1. In still other embodiments, the ethyl cellulose and a polymethacrylate polymer are present at a weight ratio of ethyl cellulose:polymethacrylate polymer of 3:1, 2:1, 3:2, 1:1, 2:3, 1:2, or 1:3. In some embodiments, the polymethacrylate is a methyl methacrylate. In other embodiments, the polymethacrylate is a methacrylic acid-ethyl acrylate co-polymer. In specific embodiments, the polymethacrylate is methacrylic acid-ethyl acrylate co-polymer 1:1.

In certain embodiments, the polymer blend comprises at least two alcohol-soluble polymers.

In other embodiments, the polymer blend comprises at least one polymer with pH-dependent dissolution and at least one polymer with pH-independent dissolution properties.

In some embodiments, the polymer blend comprises at least two polymers with pH-independent dissolution properties or at least two polymers with pH-dependent dissolution properties.

In some embodiments, the polymer with pH-independent dissolution properties is selected from ethyl cellulose and/or ethyl acrylate-methyl methacrylate co-polymer and/or ethyl acrylate-methyl methacrylate-trimethylammonioethyl methacrylate chloride co-polymer. In specific embodiments, the ethyl acrylate-methyl methacrylate-trimethylammonioethyl methacrylate chloride co-polymer is present at a ratio from about 1:2:0.1 to 1:2:0.2.

In some embodiments, the polymer with pH-dependent dissolution properties is selected from methacrylic acid ethyl acrylate co-polymer and/or butyl methacrylate-(2-dimethylaminoethyl) methacrylate-methyl methacrylate co-polymer and/or methacrylic acid methyl methacrylate co-polymer and/or methyl acrylate-methyl methacrylate-methacrylic acid co-polymer. In specific embodiments, the methacrylic acid-ethyl acrylate co-polymer is methacrylic acid-ethyl acrylate co-polymer 1:1.

In some embodiments, the oral formulation further comprises a second polymer film coat or top coat. In certain embodiments, the second polymer film coat or top coat comprises a single polymer (preferably ethylcellulose), or a blend of at least two polymers (ethylcellulose and a polymethacrylate for example). In certain embodiments, the second polymer film coat or top coat further comprises a polysaccharide gum such as acacia gum, guar gum, tragacanth gum or xanthan gum. In certain embodiments, the second polymer film coat or top coat comprises an alginic acid, or salt thereof.

In some embodiments, the therapeutic agent is selected from GHB and pharmaceutically acceptable salts, hydrates, tautomers, solvates, isotopologues and complexes of GHB. Preferably, the GHB salt is selected from sodium oxybate, calcium oxybate, potassium oxybate, magnesium oxybate or combinations thereof, See U.S. Pat. Nos. 8,591,922 or 9,132,107 which are hereby incorporated by reference in their entireties. In some embodiments, the GHB is present as a prodrug or drug-conjugate. In other embodiments, the therapeutic agent is selected from paracetamol, an opioid or an opiate and pharmaceutically acceptable salts, hydrates, tautomers, solvates, isotopologues and complexes of paracetamol, an opioid or an opiate. In specific embodiments, the therapeutic agent is selected from paracetamol, codeine or oxycodone and pharmaceutically acceptable salts, hydrates, tautomers, solvates, isotopologues and complexes of paracetamol, codeine or oxycodone.

In some embodiments, provided is an oral formulation that is resistant to alcohol-induced dose dumping. In certain embodiments, provided is an oral formulation wherein the composition is adjusted to achieve the required drug release kinetics, including, but not limited to, immediate, sustained or delayed release, to meet the target in vivo pharmacokinetic profile for said drug.

In some embodiments, the oral formulation comprises a population of drug carrier cores comprising the therapeutic agent. In other embodiments, the oral formulation comprises two or more populations of drug carrier cores comprising the therapeutic agent.

In some embodiments, the oral formulation comprises a one or more populations of immediate release (IR) drug carrier cores that provide an immediate release of the therapeutic agent in the absence of ethanol. In specific embodiments, the IR drug carrier cores release between about 70% and about 100% of the therapeutic agent after about 5 minutes to about 60 minutes of being in an aqueous buffer. In certain embodiments, the IR drug carrier cores release between about 70% and about 100% of the therapeutic agent after about 5 minutes to about 60 minutes of being in a aqueous buffer. In particular embodiments, the IR drug carrier cores release between about 70-80%, 70-90%, 70-100%, 80-90%, 80-100%, or 90-100% of the therapeutic agent in about 5-10, 5-15, 5-20, 5-30, 5-45, 5-60, 10-15, 10-20, 10-30, 10-45, 10-60, 15-30, 15-45, 15-60, 20-30, 20-45, 20-60, 30-45, 30-60, or 45-60 minutes.

In some embodiments, the oral formulation comprises one or more populations of sustained release (SR) drug carrier cores that provide a sustained release profile of the therapeutic agent in the absence of ethanol. In specific embodiments, the sustained release profile provides not more than about 10% to about 50% release of the therapeutic agent within about 1 hour of being in an aqueous buffer, between about 20% to about 70% release within about 2 hours to about 4 hours of being in an aqueous buffer, and between about 50% to about 80% release within about 4 hours to about 10 hours of being in an aqueous buffer.

In some embodiments, the oral formulation comprises one or more populations of delayed release (DR) drug carrier cores that provide a delayed release profile of the therapeutic agent in the absence of ethanol. In some embodiments, release of the therapeutic agent is delayed during gastric transit following ingestion. In specific embodiments, release of the therapeutic agent is delayed during gastric transit following ingestion and having not more than about 0% to 40% release of the therapeutic agent within about 1 hour to about 2 hours of being in an acidic aqueous buffer (pH<5). In other embodiments, release of the therapeutic agent is delayed during exposure to the acidic aqueous buffer (pH<5), and then release of the therapeutic agent increases after the formulation is subsequently exposed to a non-acidic (pH>5) aqueous solution such that release of the therapeutic agent increases to between about 50% to about 100% release within about 1 hour of being in said non-acidic aqueous solution; or to between about 10% to about 70% release within about 1 hour to about 4 hours of being in said non-acidic aqueous solution.

In some embodiments, the release rate of the therapeutic agent from the formulation demonstrates no significant change in release rate when exposed to between about 5 to about 40% ethanol (v/v) as compared to when said ethanol is not present. In certain embodiments, the release rate of the therapeutic agent from the formulation when exposed to between about 5% to about 40% ethanol (v/v) is within about 1%, 2%, 3%, 4%, 5%, 7%, 8%, 9%, 10%, 15%, 20% or 25% or more of the release when ethanol is not present. In some embodiments, the release rate of the therapeutic agent from the formulation demonstrates no significant change in release rate when exposed to about 5%, about 10%, about 15%, about 20%, about 25%, about 30%, about 35%, or about 40% ethanol (v/v) as compared to when said ethanol is not present. In certain embodiments, the release rate of the therapeutic agent from the formulation when exposed to between about 5% to about 40%, or about 5%, about 10%, about 15%, about 20%, about 25%, about 30%, about 35%, or about 40% ethanol (v/v) is within about 1%, 2%, 3%, 4%, 5%, 7%, 8%, 9%, 10%, 15%, 20% or 25% or more of the release when ethanol is not present. In specific embodiments, the release rate of the therapeutic agent is measured using an in vitro dissolution test and the about 5% to about 40%, about 5%, about 10%, about 15%, about 20%, about 25%, about 30%, about 35%, or about 40% ethanol (v/v) is present in the acidic aqueous buffer. In some embodiments, the F2 Similarity Factor is used to determine if the release rate of the therapeutic agent from the drug carrier cores demonstrates no significant change when exposed to between about 5% to about 40%, or about 5%, about 10%, about 15%, about 20%, about 25%, about 30%, about 35%, or about 40% ethanol (v/v) as compared to when said ethanol is not present. The F2 Similarity Factor is described in Shah, V P et al., *In vitro Dissolution Profile Comparison—Statistics and Analysis of the Similarity Factor, f2*. Pharm. Research, (1998) 15 (6), which is incorporated herein by reference in its entirety.

In some embodiments, the release rate of the therapeutic agent from the formulation or drug carrier core decreases by at least 5%, at least 10%, at least 20%, at least 30%, at least 40%, at least 50%, at least 60% or more, when exposed to about 5%, about 10%, about 15%, about 20%, about 25%, about 30%, about 35%, or about 40% ethanol (v/v) as compared to the release rate of said therapeutic agent when ethanol is not present.

In some embodiments, the release rate of the therapeutic agent from the formulation or drug carrier core decreases by no more than about 5%, about 10%, or about 15%, when exposed to about 5% ethanol (v/v) as compared to the release rate of said therapeutic agent when exposed to ethanol at levels greater than 5% (v/v).

In some embodiments, the release rate of the therapeutic agent from the formulation or drug carrier core decreases by no more than about 5%, about 10%, or about 15%, when exposed to about 10% ethanol (v/v) as compared to the release rate of said therapeutic agent when exposed to ethanol at levels greater than 10% (v/v).

In some embodiments, the release rate of the therapeutic agent from the formulation or drug carrier core decreases by no more than about 5%, about 10%, or about 15%, when exposed to about 15% ethanol (v/v) as compared to the release rate of said therapeutic agent when exposed to ethanol at levels greater than 15% (v/v).

In some embodiments, the release rate of the therapeutic agent from the formulation or drug carrier core decreases by no more than about 5%, about 10%, or about 15%, when exposed to about 20% ethanol (v/v) as compared to the release rate of said therapeutic agent when exposed to ethanol at levels greater than 20% (v/v).

In some embodiments, the release rate of the therapeutic agent from the formulation or drug carrier core decreases when exposed to between about 10% to about 40% ethanol (v/v) as compared to when said ethanol is not present. In some embodiments, the release rate of the therapeutic agent from the formulation demonstrates an ethanol concentration-dependent decrease in release when between about 10% to about 40% ethanol (v/v) is added to the acidic aqueous buffer. Thus in certain embodiments, the release rate of the therapeutic agent from the formulation decreases as the concentration of ethanol increases. In certain embodiments, the ethanol concentration is about at least about 10%, 15%, 20%, 25%, 30%, 35%, 40%, or greater than 40% (v/v). In specific embodiments, the ethanol concentration is at least about 10% (v/v) or more; at least about 20% (v/v) or more; at least about 30% (v/v) or more; or at least about 40% (v/v) or more.

In some embodiments, the release rate of the therapeutic agent from the formulation or drug carrier core decreases when exposed to between about 5% to about 40% ethanol (v/v) as compared to when said ethanol is not present. In some embodiments, the release rate of the therapeutic agent from the formulation demonstrates an ethanol concentration-dependent decrease in release when between about 5% to about 40% ethanol is added to the acidic aqueous buffer. Thus in certain embodiments, the release rate of the therapeutic agent from the formulation decreases as the concentration of ethanol increases. In certain embodiments, the ethanol concentration is about at least about 5%, 10%, 15%, 20%, 25%, 30%, 35%, 40%, or greater than 40%. In specific embodiments, the ethanol concentration is at least about 10% or more; at least about 20% or more; at least about 30% or more; or at least about 40% or more.

In some embodiments, the release rate or percent release of the therapeutic agent is measured using an in vitro dissolution test and the about 5% to about 40% ethanol (v/v) is present in an acidic buffer. In specific embodiments, the release rate or percent release of the therapeutic agent is measured using an in vitro dissolution test wherein the about 5% to about 40% ethanol (v/v) is present in an acidic buffer for up to two hours. Measuring ethanol-dependent dissolution rates in the presence of ethanol is believed to mimic ingested alcohol which would be present in the low pH environment of the stomach (see Rubbens J., et al., Gastric and Duodenal Ethanol Concentrations after intake of Alcoholic Beverages in Postprandial Conditions. *Molecular Pharmaceutics*, (2017) 14(12), which is incorporated herein by reference in its entirety). In specific embodiments, the percent release, or release rate, of the therapeutic agent is measured in vitro using a standard US Pharmacopeia (USP) dissolution test. For example, in certain embodiments, the test is conducted using the USP Dissolution Apparatus 2 (paddle) operated at 100 RPM as in US 2012/0076865, by the steps of:
 (a) Stage I: exposing the formulation to 750 mL solution of 0.1N hydrochloric acid (HCl) (approximately pH 1.2), 37° C. for 15 minutes or 2 hours;
 (b) Stage II: adding 250 mL of 0.316M Tris buffer (degassed and pre-equilibrated to 37° C.) and adjusting the pH to 6.8 using 25% HCl; and exposing the formulation for 2 hours;
 (c) drawing samples at prescribed intervals;
 (d) filtering the sample through a suitable filter; and,
 (e) determining the drug concentration using high performance liquid chromatography (HPLC).
 In further embodiments, this test is conducted in the presence of 5-40% v/v ethanol, wherein the solution of Stage I further comprises 5-40% v/v ethanol. E.g., if the test is conducted at 5% (v/v), the solution of Stage I is a 750 mL solution of 0.1N HCl and 5% v/v EtOH; if the test is conducted at 20% (v/v), the solution of Stage I is a 750 mL solution of 0.1N HCl and 20% v/v EtOH.
 In other embodiments, the test can be conducted with other volumes of an acidic solution and/or buffer.

In some embodiments, dissolution of the pharmaceutical formulation with increased resistance to alcohol-mediated dissolution provides an immediate release profile. In certain embodiments, dissolution of the drug carrier core provides about 70-100% release of the therapeutic agent after about 5 to about 60 minutes of being in an aqueous buffer having an initial pH of about 6.8. In some embodiments, the IR drug carrier cores release between about 70% and about 100% of the therapeutic agent after about 5 minutes to about 60 minutes of being in an aqueous buffer having an initial pH of about 6.8. In particular embodiments, the IR drug carrier cores release between about 70-80%, 70-90%, 70-100%, 80-90%, 80-100%, or 90-100% of the therapeutic agent in about 5-10, 5-15, 5-20, 5-30, 5-45, 5-60, 10-15, 10-20, 10-30, 10-45, 10-60, 15-30, 15-45, 15-60, 20-30, 20-45, 20-60, 30-45, 30-60, or 45-60 minutes.

In some embodiments, dissolution of the pharmaceutical formulation with increased resistance to alcohol-mediated dissolution provides about 20-90% release of the therapeutic agent after 60 minutes of being in a non-acidic aqueous buffer having an initial pH of about 6.8. In some embodiments, dissolution of the pharmaceutical formulation with increased resistance to alcohol-mediated dissolution in a USP II dissolution apparatus in non-acidic aqueous buffer having initial pH of about 6.8 provides about 30-70% release of the therapeutic agent after 60 minutes of being in the buffer phase. In certain embodiments, a two hour incubation in an acidic/fluid phase precedes incubation in the non-acidic aqueous buffer as according to USP standards for dissolution profiling. Thus in some embodiments dissolution of the formulation provides about 20-90% release of the therapeutic agent after 60 minutes of being in a non-acidic aqueous buffer having an initial pH of about 6.8, wherein prior to incubation in said non-acidic aqueous buffer the formulation is incubated for two hours in an acidic solution. In certain embodiments incubation in the acidic phase is reduced to about 15 minutes, or from 10-20 minutes. In some embodiments dissolution of the formulation provides about 25-80% release of the therapeutic agent after 60 minutes of being in a non-acidic aqueous buffer having an initial pH of about 6.8, wherein prior to incubation in said non-acidic aqueous buffer the formulation is incubated for 15 minutes, or about 10-20 minutes, in an acidic solution. In some embodiments, dissolution of formulation in a USP II dissolution apparatus in anon-acidic aqueous buffer having initial pH of about 6.8 provides about 30-70% release of the therapeutic agent after 60 minutes of being in the buffer phase, wherein prior to incubation in said buffer phase the formulation is incubated for 15 minutes or two hours in an acidic solution.

In some embodiments, the cellulose and/or polymethacrylate polymers have been treated with a plasticizer. A plasticizer is selected based on its physicochemical properties to ensure compatibility with the cellulose and/or polymethacrylate polymers. Examples of suitable plasticizers include, but are not limited to, acetyltributyl citrate, acetyltriethyl citrate, benzyl benzoate, dibutyl phthalate, dibutyl sebacate, diethyl phthalate, dimethyl phthalate, glyceryl triacetate, polyethylene glycol ("PEG"), propylene glycol, pyrrolidone, triacetin, triethyl citrate ("TEC") and tributyl citrate ("TBC").

In some embodiments, the alcohol-resistant formulations provide modified release of the therapeutic agent in the absence of ethanol while preventing this release from accelerating in the presence of ethanol. In some embodiments, the alcohol-resistant formulations provide modified release of the therapeutic agent in the absence of ethanol while preventing this release from accelerating due to the simultaneous consumption of ethanol.

In some embodiments, the alcohol-resistant formulations provide modified release of the therapeutic agent with release kinetics that enable a single dose be taken by the patient in a 24 hour period. In some embodiments, the alcohol-resistant formulations provide modified release of the therapeutic agent with release kinetics that enable a single dose be taken by the patient in a 24 hour period and wherein release of the therapeutic agent from said formulation is prevented from accelerating in the presence of alcohol or due to the simultaneous consumption of alcohol. In specific embodiments, the therapeutic agent is GHB, paracetamol, an opioid or an opiate. In other specific embodiments, the therapeutic agent is GHB, paracetamol, codeine or oxycodone. In some specific embodiments, the therapeutic agent is GHB.

In some embodiments, alcohol-resistant formulations are used to treat a patient suffering from a disease or condition and/or a symptom caused by a disease or condition.

In some embodiments, the alcohol-resistant formulation comprises one or more populations of drug carrier cores comprising a therapeutic agent. In certain embodiments, the formulation comprises a core and one or more coatings. In particular embodiments, the core comprises between 70% and 90% (w/w of the core) GHB salt, 1-20% (w/w of the core) microcrystalline cellulose, and 1-10% (w/w of the core) hydroxypropylcellulose. In certain embodiments, the formulation comprises a core and a first coating disposed over the core comprising ethylcellulose and methacrylic acid-ethyl acrylate co-polymer (1:1), wherein said coating is targeted to be from about 5% to about 60% by weight of the core and the ratio of ethylcellulose to co-polymer is between about 1:3 and 3:1, respectively, based on polymer weight. In preferred embodiments, the ratio of ethylcellulose to co-polymer is between about 1:2 and 2:1, respectively, based on polymer weight. In other embodiments, said formulation further comprises a second coating disposed over the first coating comprising ethylcellulose, methacrylic acid-ethyl acrylate co-polymer (1:1) and guar gum, wherein guar gum is added at 1-10% w/w of the cellulose polymer, wherein said second coating is dispersed over the first coating and targeted to be from about 1% to about 50% by weight of the core and first coating, and wherein the ratio of ethylcellulose to co-polymer is between about 1:3 and 3:1, respectively, based on polymer weight. In certain embodiments, the ethyl cellulose in the first and/or second coating is Aquacoat® ECD.

In some embodiments, the alcohol-resistant formulation comprises a drug carrier core having between 70% and 90% (w/w) GHB salt, 1-20% (w/w) microcrystalline cellulose, and 1-10% (w/w) hydroxypropylcellulose; and, a first coating comprising Aquacoat® ECD and methacrylic acid-ethyl acrylate co-polymer (1:1) wherein said coating is targeted to be from about 5% to about 60% by weight of the core.

In some embodiments, the alcohol-resistant formulation comprises a drug carrier core having between 70% and 90% (w/w) GHB salt, 1-20% (w/w) Avicel 101 (microcrystalline cellulose), 0-3% (w/w) L-HPC LH31 (low-substituted hydroxypropyl cellulose), and 1-10% (w/w) Hydroxypropylcellulose 300-600 CPS, a first coat disposed over the core comprising ethylcellulose (as Aquacoat® ECD) and methacrylic acid-ethyl acrylate co-polymer 1:1 (as either Eudragit L30D55 or Eudragit L100-55) at a ratio of between 1:3 and 3:1 respectively, based on polymer weight; and, optionally, a top or second coat comprising ethyl cellulose, methacrylic acid-ethyl acrylate co-polymer (1:1) and guar gum which is dispersed over the first coating and targeted to be from about 1% to about 50% by weight of the core and first coating. In certain embodiments, the ethyl cellulose in the first and/or second coating is Aquacoat® ECD. In some embodiments, a sub-coat is present between the first coating and the core.

In certain embodiments, the GHB salt is a mixture of GHB salts. In specific embodiments, the GHB salt in the modified release formulation is calcium GHB monohydrate. In other embodiments, the GHB salt in the immediate release formulation is a mixture of sodium GHB and potassium GHB.

In some embodiments, drug carrier core comprises a mixed salt oxybate. In other embodiments, the immediate release portion of the formulation comprises a mixed salt oxybate. This mixed salt oxybate comprises varying percentages of oxybate, expressed as % molar equivalents (% mol. equiv.) of Na. GHB, K.GHB, Mg.(GHB)$_2$, and/or Ca.(GHB)$_2$. The terms "% molar equivalents" and "% mol. equiv.," as used herein, refer to molar composition of salts expressed as a percent of GHB equivalents. Those skilled in the art will understand that as each GHB unit is considered to be one molar equivalent, the monovalent cations, Na' and K', have one molar equivalent per salt, and the divalent cations, Mg$^{+2}$ and Ca$^{+2}$, have two molar equivalents per salt. See U.S. Pat. Nos. 8,591,922; 8,901,173; 9,132,107; 9,555,017; 10,195,168 for amounts of % mol. equiv. useful in the present disclosure.

In some embodiments, any of the salts, such as the Na. GHB salt, the K.GHB salt, the Mg.(GHB)$_2$ salt or the Ca.(GHB)$_2$, is present in about 1%-5%, about 5%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, about 90%-95%, or about 95%-100% (% mol. equiv.). In some embodiments, the Na. GHB salt is present in a % mol. equiv. of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (% mol. equiv.). In some embodiments, the Na.GHB salt is absent.

In some embodiments, where the mixed salt oxybate comprises a mixture of Na. GHB, K.GHB, Mg.(GHB)$_2$, and Ca.(GHB)$_2$, the Na.GHB salt is present in a % mol. equiv. of about 1%-15%, 5%-10%, or about 8%; the K.GHB salt is present in a % mol. equiv. of about 10%-30%, 15%-25%, or about 23%; the Mg.(GHB)$_2$ salt is present in a % mol. equiv. of about 10%-30%, 15%-25%, or about 21%; and the Ca.(GHB)$_2$ salt is present in a % mol. equiv. of about 30%-60%, 40%-50, or about 48% (% mol. equiv.).

In some embodiments, the mixed salt oxybate comprises about 8% mol. equiv. of sodium oxybate, about 23% mol. equiv. of potassium oxybate, about 21% mol. equiv. of magnesium oxybate and about 48% mol. equiv. of calcium oxybate. In some embodiments, where the mixed salt oxybate comprises a mixture of Na. GHB, K.GHB, Mg.(GHB)$_2$, and Ca. (GHB)$_2$, wherein the mixture comprises Na. GHB, K.GHB, Mg. (GHB)$_2$, and Ca. (GHB)$_2$ salts are present in a % mol. equiv. ratio of about 8:23:21:48, respectively.

In some embodiments, where the pharmaceutical composition comprises a mixture of Na.GHB, K.GHB, and Ca. (GHB)$_2$, the Na.GHB salt is present in a % mol. equiv. of about 5%-40%, the K.GHB salt is present in a % mol. equiv. of about 10%-40%, and the Ca.(GHB)$_2$ salt is present in a % mol. equiv. of about 20%-80%.

One embodiment of the present invention is a method for treating a patient who is suffering from a disease or condition, such as for example, a disease or condition that is treatable with GHB, paracetamol, an opioid and/or an opiate. In some embodiments, the disease or condition is treatable with GHB, paracetamol, codeine or oxycodone. In specific embodiments, the disease or condition is treatable with GHB. In certain embodiments the disease or condition is a Therapeutic Category as described herein, such as but not limited to, sleeping disorders, drug abuse, alcohol and/or opiate withdrawal, a reduced level of growth hormone, anxiety, analgesia (including the treatment of mild, moderate and/or severe pain; including acute, chronic, breakthrough, somatic, visceral or neuropathic pain), effects in certain neurological disorders, such as Parkinson's Disease, depression, certain endocrine disturbances and tissue protection following hypoxia/anoxia such as in stroke or myocardial infarction, or an increased level of intracranial pressure. Another embodiment of the invention is a method of treating and/or preventing a symptom associated with a disease or condition such as for example, a disease or condition treatable with GHB, including but not limited to, excessive daytime sleepiness, cataplexy, sleep paralysis, apnea, narcolepsy sleep time disturbances, hypnagogic hallucinations, sleep arousal, insomnia, essential tremor and nocturnal myoclonus with gamma-hydroxybutyrate (GHB) or a salt thereof, comprising: orally administering to the patient in need of treatment, an alcohol-resistant formulation comprising a therapeutic agent wherein there is reduced release of the therapeutic agent in the presence of ethanol. In specific embodiments, the therapeutic agent is GHB.

One embodiment of the present invention is a method for treating a patient who is suffering from excessive daytime sleepiness, cataplexy, sleep paralysis, apnea, narcolepsy sleep time disturbances, hypnagogic hallucinations, sleep arousal, insomnia, and nocturnal myoclonus with gamma-hydroxybutyrate (GHB) or a salt thereof, comprising: orally administering to the patient in need of treatment, a GHB formulation with reduced GHB release in the presence of ethanol. In certain embodiments, the ethanol concentration is at least about 5%, 10%, 15%, 20%, 25%, 30%, 35%, 40%, or greater than 40%. In certain embodiments, the ethanol concentration is about at least about 10% or more; at least about 20% or more; at least about 30% or more; or at least about 40% or more.

Another embodiment of the invention is a method of safely administering GHB, or a salt thereof, for treatment and/or prevention of a disease, disorder or symptom that is treatable with GHB, such as but not limited to, sleeping disorders, drug abuse, alcohol and/or opiate withdrawal, a reduced level of growth hormone, anxiety, analgesia, effects in certain neurological disorders, such as Parkinson's Disease, depression, fibromyalgia, certain endocrine disturbances and tissue protection following hypoxia/anoxia such as in stroke or myocardial infarction, or an increased level of intracranial pressure, excessive daytime sleepiness, cataplexy, sleep paralysis, apnea, narcolepsy, sleep time disturbances (including, for example, those resulting from stress or trauma such as post-traumatic stress disorder and/or traumatic brain injury), REM sleep behavior disorder (RBD; especially as in Parkinson's), hypnagogic hallucinations, sleep arousal, insomnia (including various types of insomnia such as, for example, idiopathic hypersomnia), and nocturnal myoclonus in a human patient, comprising: orally administering to the patient in need of treatment, a GHB formulation with reduced GHB release in the presence of ethanol. In certain embodiments, the ethanol concentration is at least about 5%, 10%, 15%, 20%, 25%, 30%, 35%, 40%, or greater than 40%. In certain embodiments, the ethanol concentration is about at least about 10% or more; at least about 20% or more; at least about 30% or more; or at least about 40% or more.

In each of the embodiments of the invention the method includes administering GHB at between 1 and 10 grams/day or between 4.5 and 9 grams/day in a 24 hour period. In some of the embodiments of the invention the method includes administering GHB at between 7 and 10 grams/day in a 24 hour period.

In a further embodiment the method can include administering GHB as a single salt or a mixture of salts of GHB selected from the group consisting of a sodium salt of gamma-hydroxybutyrate (Na.GHB), a potassium salt of gamma-hydroxybutyrate (K.GHB), a magnesium salt of gamma-hydroxybutyrate (Mg(GHB)$_2$), and a calcium salt of gamma-hydroxybutyrate (Ca(GHB)$_2$).

Another embodiment of the present invention is a method of administering GHB, paracetamol, an opioid or opiate (e.g. codeine or oxycodone) to a patient in need thereof, comprising administering to the patient a therapeutically effective amount of GHB, paracetamol, an opioid or opiate (e.g. codeine or oxycodone) while avoiding concomitant administration of alcohol. A preferred embodiment is a method of administering GHB to a patient in need thereof, comprising administering to the patient a therapeutically effective amount of GHB while avoiding concomitant administration of alcohol.

The invention may also comprise a method for reducing the side effects of GHB, paracetamol, an opioid or opiate (e.g. codeine or oxycodone) in a patient in need thereof, comprising administering to said patient an effective amount of an alcohol rugged modified release formulation of GHB, paracetamol, an opioid or opiate (e.g. codeine or oxycodone). A preferred embodiment is a method for reducing the side effects of GHB in a patient in need thereof, comprising administering to said patient an effective amount of an alcohol rugged modified release formulation of GHB.

Figure 25:
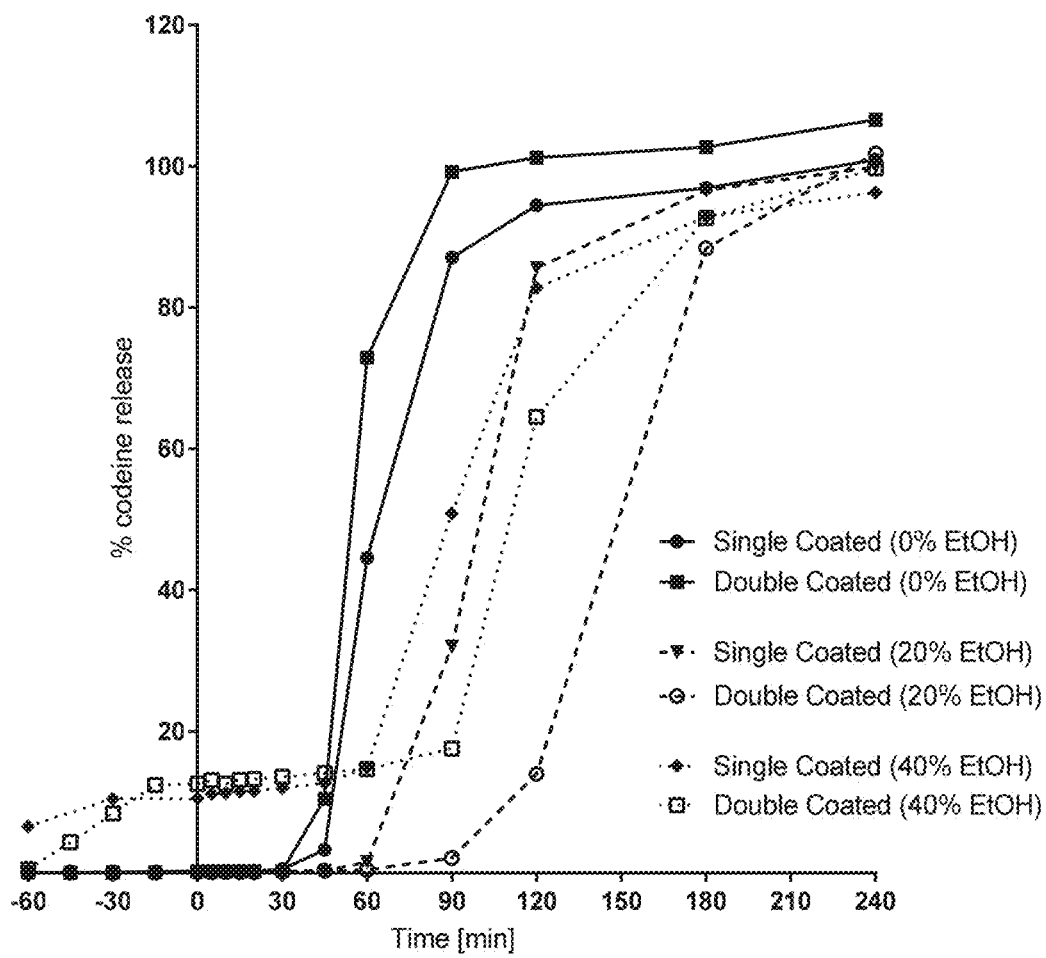

FIG. 25 is a graph showing the two-phase in vitro dissolution profiles of codeine phosphate from a pellet core having a binary polymer film coat of 22% w/w of the uncoated pellet core.

Figure 26:
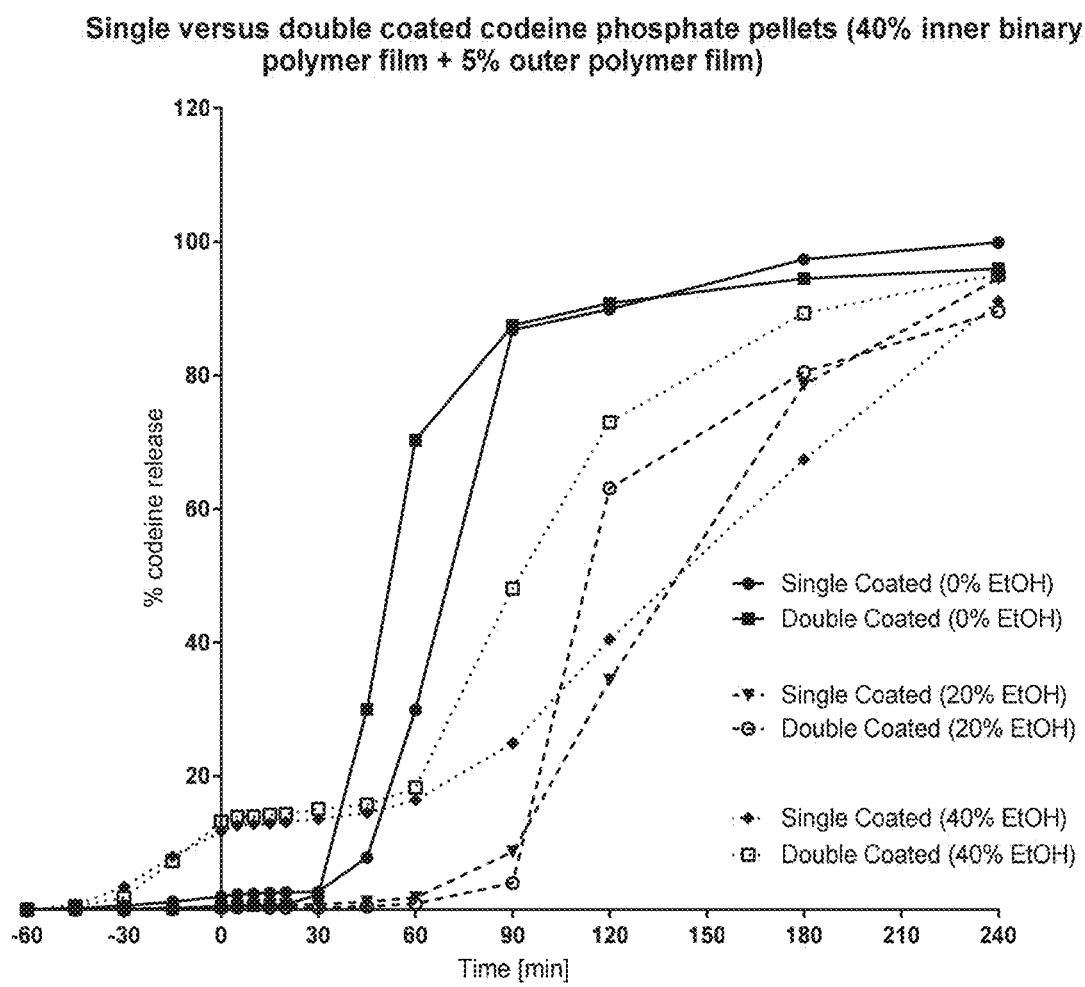

FIG. 26 is a graph showing the two-phase in vitro dissolution profiles of codeine phosphate from a pellet core prepared as per Example 11. The in vitro dissolution characteristics of 'single' and 'double' coated codeine phosphate pellets were determined. The 'single coated' pellets were prepared by applying a polymer film coat consisting of a 1:1 mixture of ethylcellulose and poly(methacrylic acid-ethyl acrylate co-polymer). The binary polymer film coat was applied to a target weight gain of 30% w/w polymer of the uncoated codeine phosphate pellet core. The 'double coated' pellets were prepared by adding an additional outer polymer film coat consisting of a mixture of ethylcellulose, poly (methacrylic acid-ethyl acrylate co-polymer) and guar gum. Both compositions were exposed to 0% v/v, 20% v/v and 40% v/v EtOH for up to 60 minutes during the acid phase dissolution test.

Figure 27:
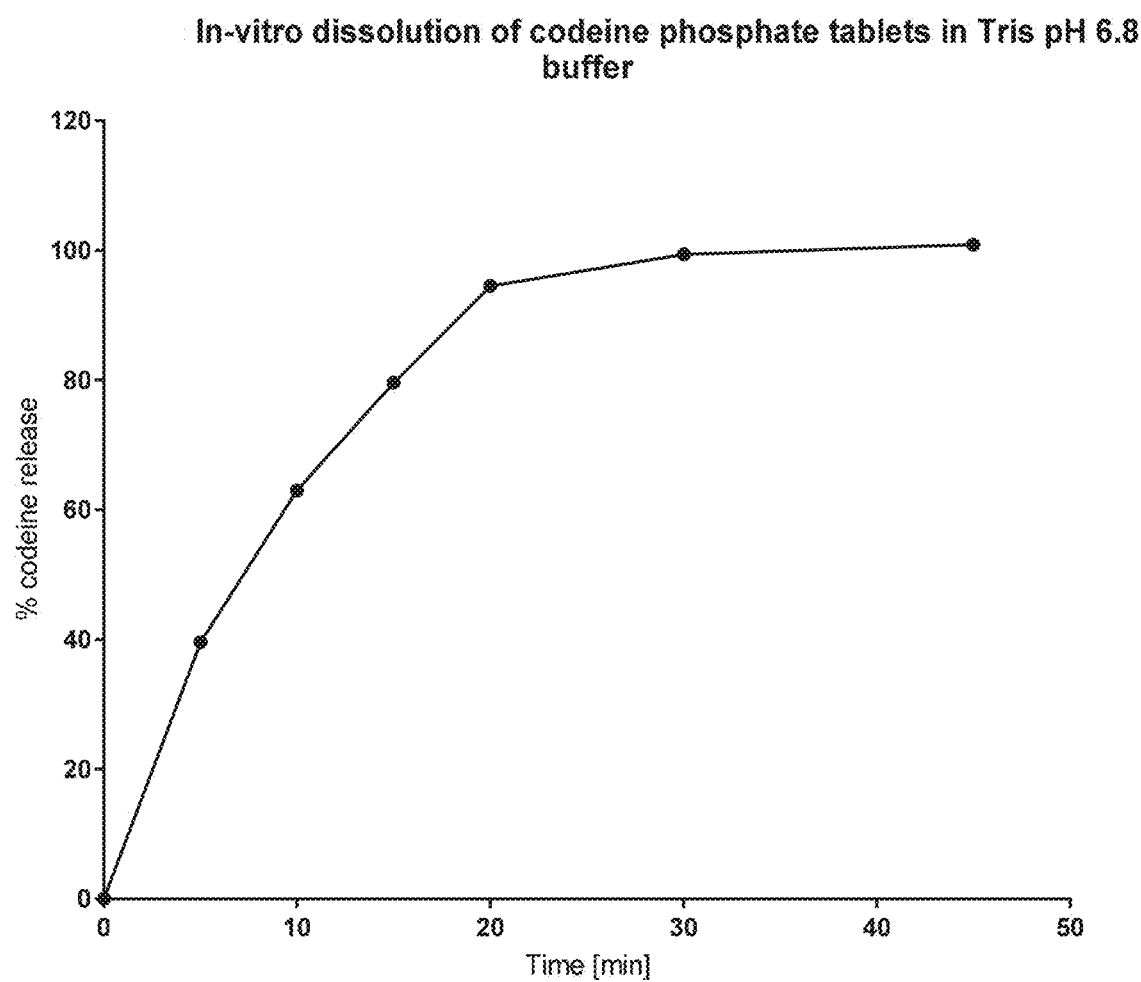

FIG. 27 is a graph showing the in vitro dissolution of codeine phosphate tablets in Tris pH 6.8 buffer.

Figure 28:
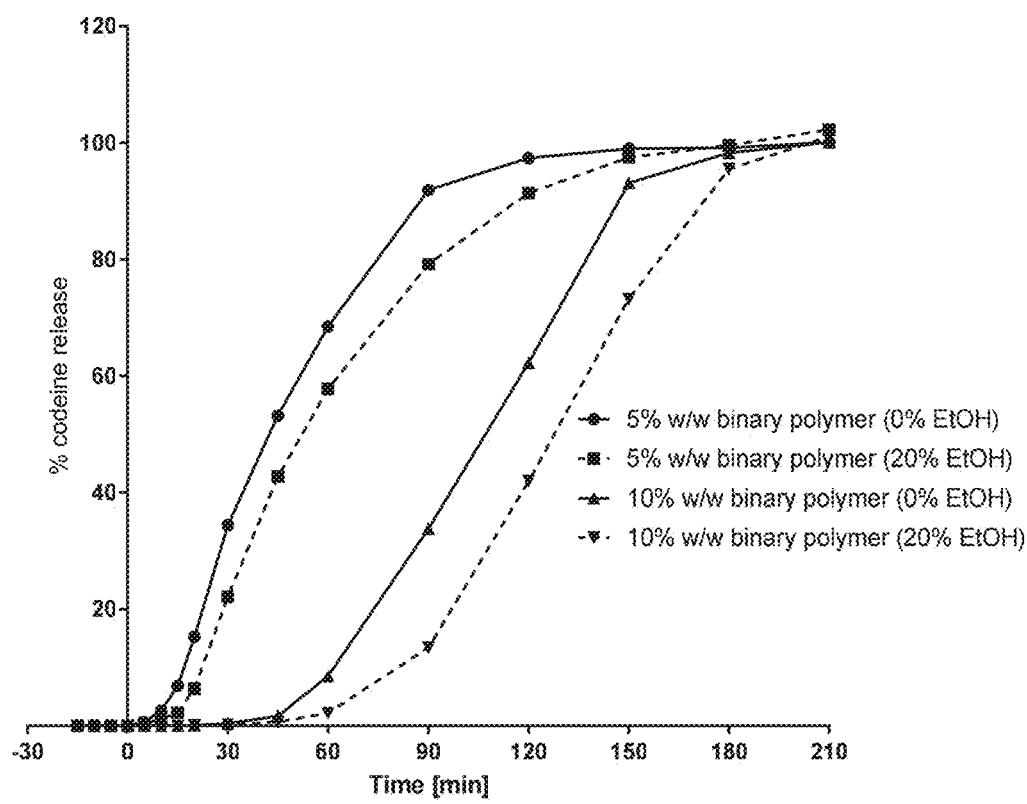

FIG. 28 is a graph showing the impact of the thickness of the binary polymer film coating on the dissolution of codeine phosphate tablets in the presence and absence of ethanol.

Figure 29:
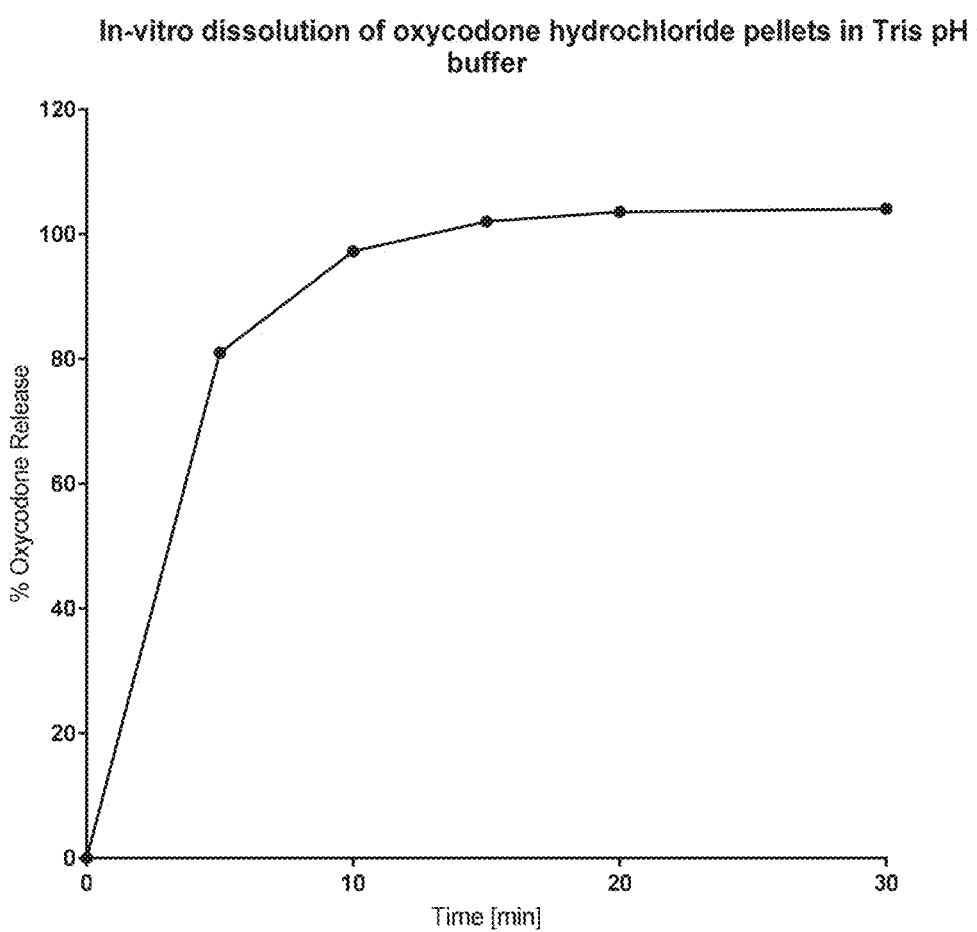

FIG. 29 is a graph showing the in vitro dissolution of oxycodone hydrochloride pellets in Tris pH 6.8 buffer.

Figure 30:
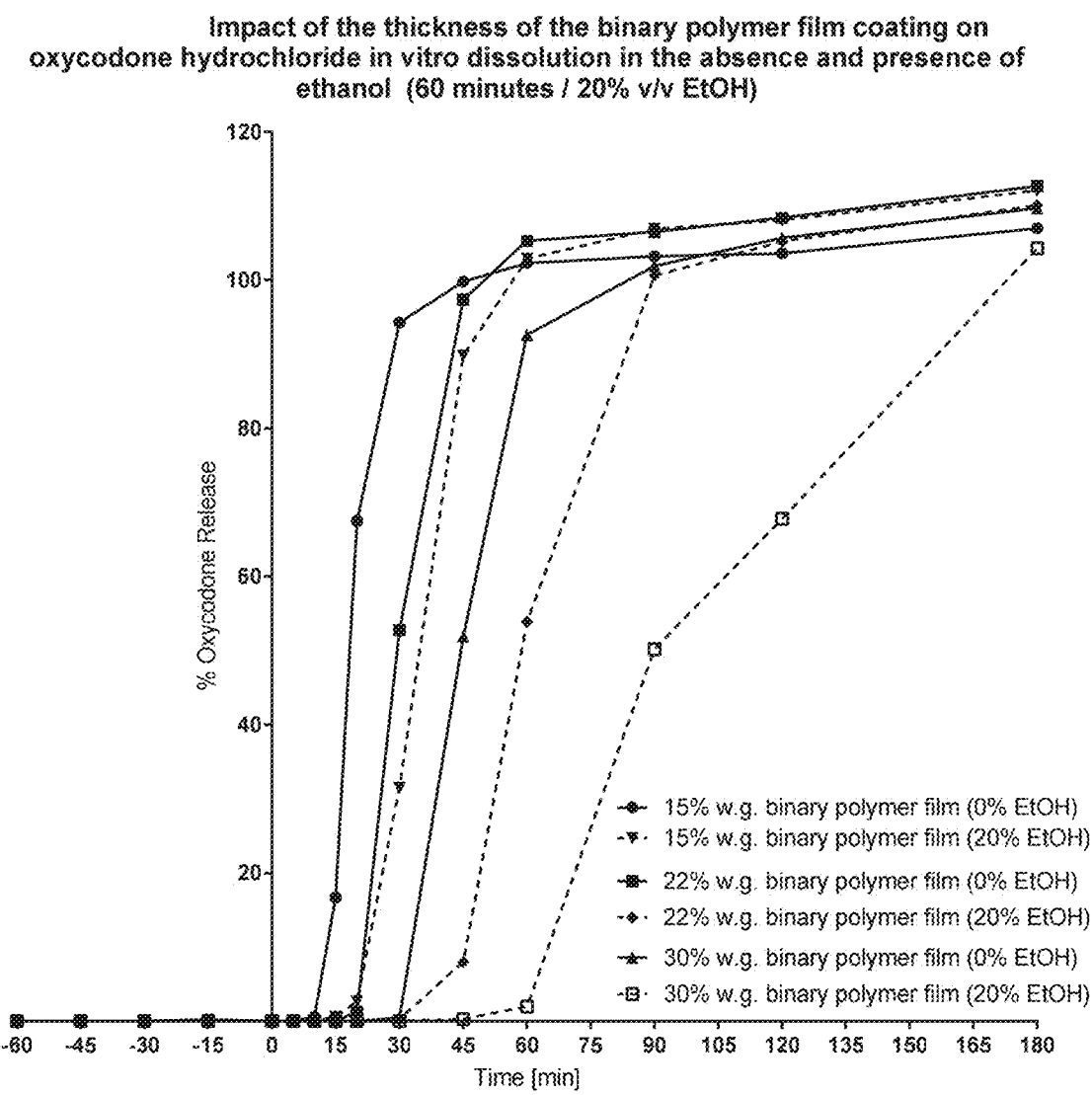

FIG. 30 is a graph showing the impact of the thickness of the binary polymer film coating on the dissolution of oxycodone hydrochloride pellets in the presence and absence of ethanol.

Figure 31:
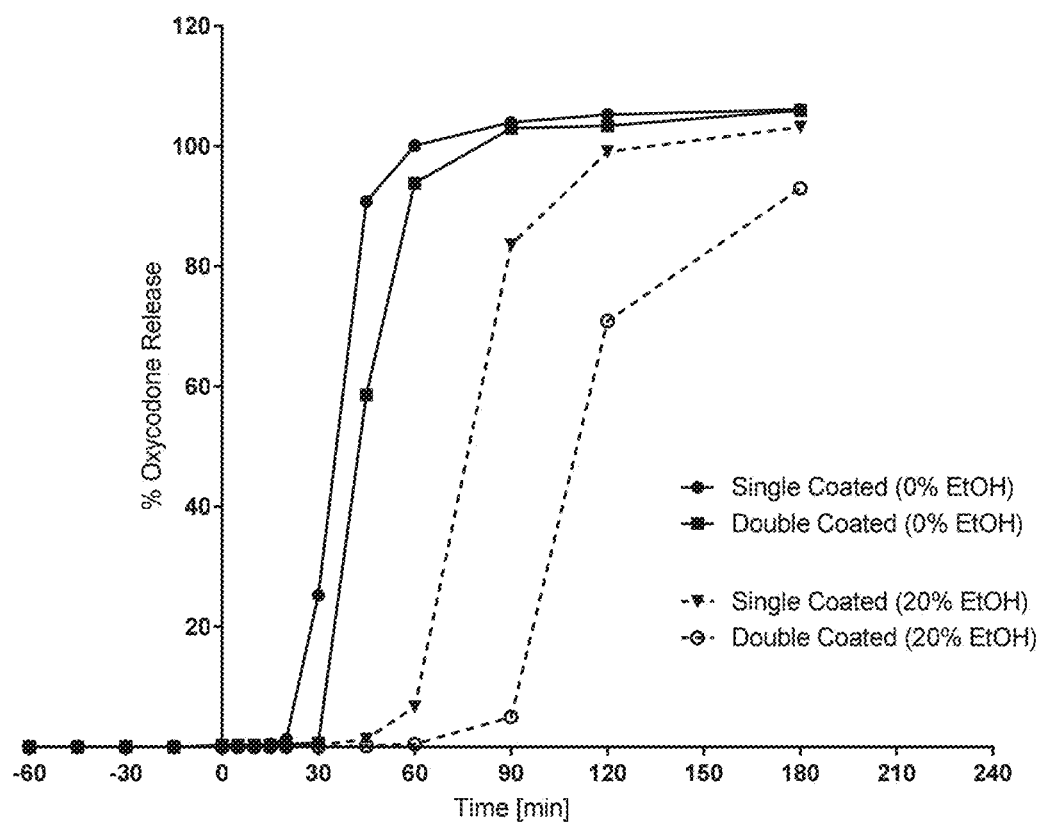

FIG. 31 is a graph showing the in vitro dissolution of oxycodone hydrochloride pellets using either single or double-coated pellets.

Figure 32:
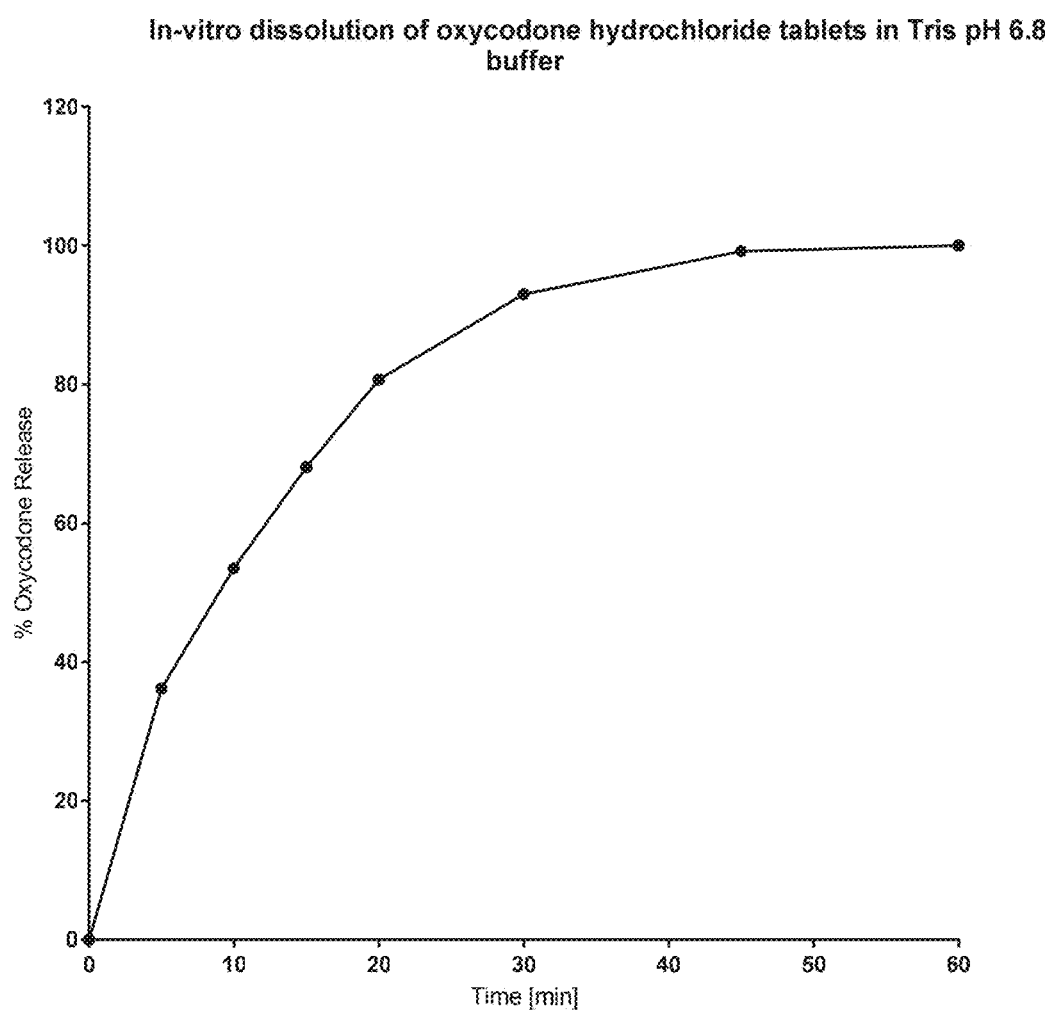

FIG. 32 is a graph showing the in vitro dissolution of oxycodone hydrochloride tablets in Tris pH 6.8 buffer.

Figure 33:
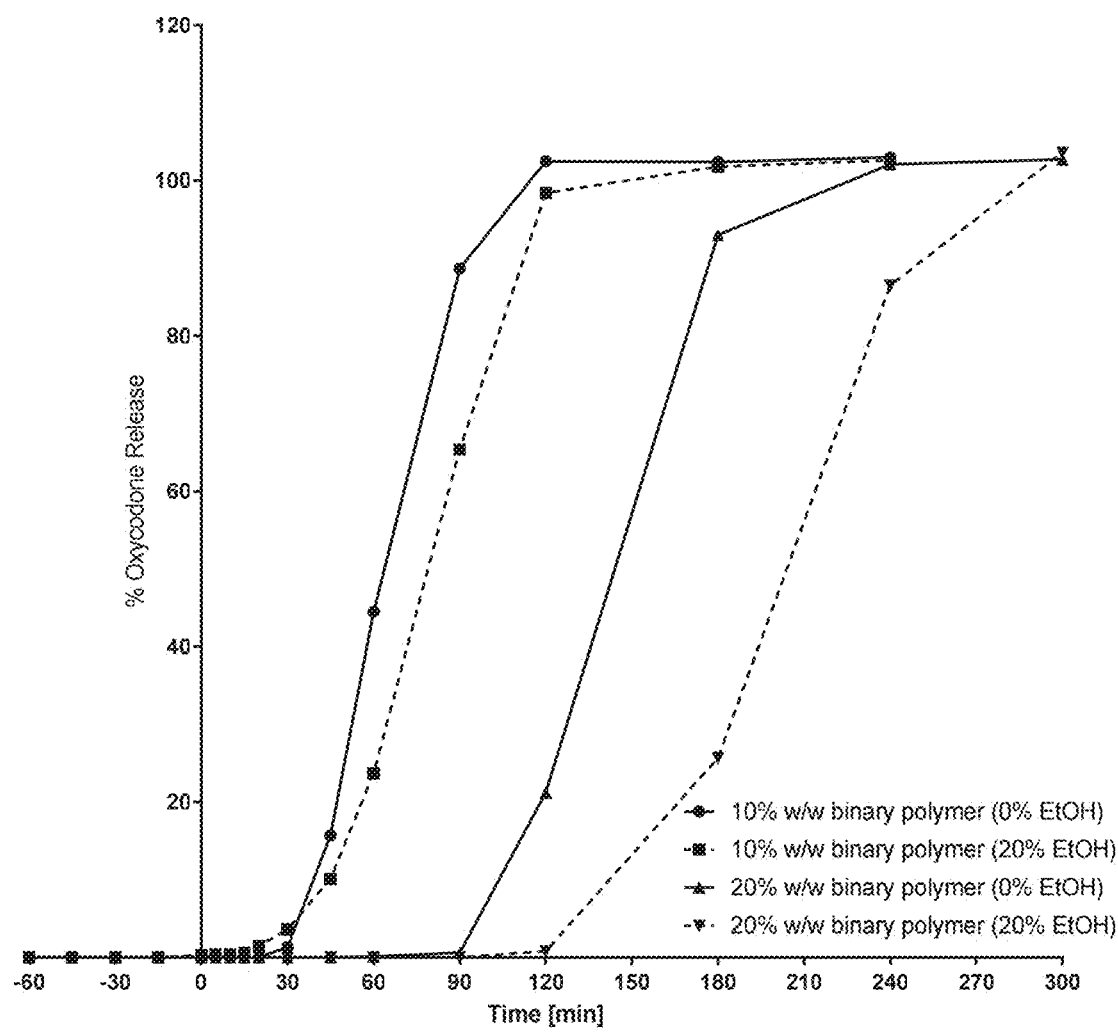

FIG. 33 is a graph showing the impact of the thickness of the binary polymer film coating on the dissolution of oxycodone hydrochloride tablets in the presence and absence of ethanol.

DETAILED DESCRIPTION OF THE INVENTION

Alcohol-induced dose dumping is a critical parameter to consider when designing and developing modified release oral formulations. Oral formulations usually contain high concentrations of drug. Some modified release oral dosage forms can contain drugs or excipients that have altered solubility in ethanol. Ingestion of alcohol, either intentionally or unintentionally, may lead to dangerously high drug exposure if the modified release formulation is sensitive to ethanol concentration. Thus provided herein are alcohol rugged oral formulations that are resistant to dose dumping and which provide improved dissolution properties in increasing concentrations of ethanol.

In the following description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the scope of the present invention. The following description is, therefore, not to be taken in a limited sense, and the scope of the present invention is defined by the appended claims.

The following patents and applications are hereby incorporated by reference in their entireties for all purposes: U.S. Pat. Nos. 6,472,431, 6,780,889, 7,262,219, 7,851,506, 8,263,650, 8,324,275; 8,859,619, 8,952,062, 8,591,922, 8,771,735, 7,895,059; 7,797,171; 7,668,730; 7,765,106; 7,765,107, 8,457,988, 8,589,182, 8,731,963; 8,771,735, 8,772,306, 8,778,398, 9,795,567, U.S. patent application Ser. Nos. 61/317,212, 13/071,369, 14/045,673, 14/172,751, 14/821,384, 15/385,447, PCT/US2010/033572, PCT/US2009/061312, 2009/0137565; and 2012/0076865. The following patents are also incorporated by reference: U.S. Pat. Nos. 5,380,937; 4,393,236 German Patent DD 237,309 A1; and British Pat. Nos. 2295390 and 922,029. In addition, these patents are also incorporated by reference: U.S. Pat. Nos. 4,524,217, 6,316,025, 7,993,673, 8,216,610, 9,271, 974.

The following patents and applications are also incorporated by reference for all purposes: US Publication No. 2006/0193912 describes compositions with a mixture of gums and ionizable gel strength enhancing agent that are expected to exhibit reduced alcohol induced dose dumping; US Publication No. 2007/0264346 provides an oral pharmaceutical form comprising micromultiparticles of the reservoir type for the modified release of at least one active principle, said form being resistant to immediate dumping of the dose of active principle in the presence of alcohol; International (PCT) Publication No. 2007/053698 describes once-a-day controlled release compositions of opioid analgesics that exhibit improved properties with respect to co-administration with aqueous alcohol; International (PCT) Publication No. 2008/086804 describes use of polyglycol, especially, polyethylene glycol for the preparation of a pharmaceutical composition, wherein the composition is without ethanol induced dose dumping. According to the application, the oral solid dosage forms are prepared by heating in order to melt or soften the polymer followed by solidification; US Publication No. 2008/0085304 describes ethanol-resistant controlled release pharmaceutical compositions comprising a hydrophilic gum, a homopolysaccharide gum, and a pharmaceutical diluent; and, US Publication No. 2009/0155357 discloses a modified release oral dosage form comprising alcohol insoluble coating, which is preferably water insoluble. Other patent or non-patent references cited throughout are also incorporated by reference in their entireties.

Definitions

In the specification and claims that follow, references will be made to a number of terms which shall be defined to have the following meaning.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

"Alcohol induced dose dumping" means the increased release of a drug from a dosage form in the presence of alcohol.

"Acidic aqueous buffer" or "acid buffer" means a buffer with pH<5.

"Alcohol rugged" or "alcohol resistant" means a formulation that is resistant to alcohol induced dose dumping, such that the rate of drug release from the formulation does not significantly increase, or is lowered, in the presence of alcohol.

"Alcohol" as used herein refers to ethanol, any ethanol containing product, or an ethanol-containing ("alcoholic") beverage such as beer, wine, and hard liquors such as vodka, rum, or whiskey; ethanol-containing beverage is commonly referred to as an alcoholic beverage, liquor, or simply alcohol all of which are included herein as referring to "alcohol" or "ethanol". It is meant to include any ethanol containing product or excipient such as liquid media or solid dosage forms (tablets, capsules for example), including those listed by the FDA Inactive Ingredient Database (IID) as alcohol-containing excipients such as, for example, alcohol used in oral therapeutic solutions, benzyl alcohol (used in capsule and soft gelatin caps and DR or SR tablets), butyl alcohol, cetyl alcohol, cetostearyl alcohol, isopropyl alcohol and stearyl alcohol.

"Co-ingested" or "co-ingestion" means the presence of both a drug (e.g. GHB) and alcohol in the body (e.g. stomach) which occurred through either simultaneous or subsequent ingestion of each and includes co-ingestion that occurs either intentionally or accidentally.

"Controlled release" or "CR" dosage forms or formulations as used herein are meant to include any dosage form or formulation maintains drug release over a sustained period at a nearly constant rate.

"Daily dose" means the total dose or dosage that is taken within a 24 hour period.

"Drug carrier core" or "drug containing core" or "core" means the inner material which contains the drug as well as any suitable excipients, if necessary, used to prepare or maintain the drug inside the core such as binders or lubricants. The drug carrier core can be prepared in the form of numerous shapes and/or sizes including, for example, granules, tablets, spheres, pellets, minitablets, microtablets, microparticles, microspheres, microcapsules, micropellets, beads, multi-particulates as well as particles having diameters up to about 5 mm; the drug carrier cores may be any suitable particle size or shape. For example, the drug carrier cores can be in the form of a "micropellets" having a particle size range of about 50-5,000 μm, or can be in the form of "minitablets" which have a nominal (e.g., mean) particle diameter in the range of about 2-5 mm. The drug carrier cores can be "microtablets" which have nominal (e.g., mean) particle diameters of less than about 2 mm, for example about 1-2 mm. The drug carrier cores can also be microspheres, having a particle size range of about 50-500 p.m. The drug carrier cores can be sized prior to coating, or after coating with one or more sub-coats, coatings, or top-coats. For example the drug carrier cores can be sized by screening or sieving prior to coating. Exemplary size ranges include, but are not limited to about 0.5 mm to 0.8 mm, 0.5 mm to 1.0 mm, 0.5 mm to 1.25 mm, 0.5 to 1.5 mm, 0.5 to 1.75 mm, 0.5 to 2.0 mm, 0.8 mm to 1.0 mm, 0.8 mm to 1.25 mm, 0.8 to 1.5 mm, 0.8 to 1.75 mm, 0.8 to 2.0 mm, 1.0 mm to 1.25 mm, 1.0 to 1.5 mm, 1.0 to 1.75 mm, 1.0 to 2.0 mm, 1.25 to 1.5 mm, 1.25 to 1.75 mm, 1.25 to 2.0 mm, 1.5 to 1.75 mm, 1.5 to 2.0 mm, or 1.75 to 2.0 mm Further, the drug carrier core can also be referred to a core relating to its size and/or shape; for example, a "drug carrier core" can be referred to as a "pellet core" when the drug carrier core is the size and/or shape of a pellet, or the drug carrier core can also be referred to as a "bead core" when the drug carrier core is the size and/or shape of a bead. For example, a "calcium oxybate pellet core" is meant to be a "drug carrier core" which comprises calcium oxybate and which is the size and/or shape of a pellet; similarly; a "calcium 3-hydroybutyrate (Ca-3HB) pellet core" or "Ca3HB pellet core" is meant to is meant to be a "drug carrier core" which comprises calcium 3-hydroybutyrate and which is the size and/or shape of a pellet.

"Ethanol rugged" "ethanol resistant", "alcohol rugged", or "alcohol resistant" means a formulation that is resistant to alcohol induced dose dumping, such that the rate of drug release from the formulation does not significantly increase, or is lowered, in the presence of ethanol; comparison of the drug release rate can be measured using the F2 similarity test as described in Shah, V P et al., In vitro Dissolution Profile Comparison—Statistics and Analysis of the Similarity Factor, f2. Pharm. Research, (1998) 15 (6).

"EtOH" means ethanol.

"Nightly dose" means the total dose or dosage that is taken within a 24 hour period but usually taken before or during someone's sleep cycle.

"Dosage amount" means an amount of a drug suitable to be taken during a fixed period, usually during one day (i.e., daily or nightly or within a 24 hour period).

"Dosage amount adapted for oral administration" means a dosage amount that is of an amount deemed safe and effective for the particular patient under the conditions specified. As used herein and in the claims, this dosage amount is determined by following the recommendations of the drug manufacturer's Prescribing Information as approved by the US Food and Drug Administration.

"Dosage form" means a drug formulation which may be prescribed and/or administered to a subject and is meant to include any solid, semi-solid, liquid, suspension, frozen or freeze-dried preparation of a drug, including but not limited to, tablets, minitablets, soft or hard capsules, gel capsules, caplets, granules, pellets, micropellets, beads, powders, sachets, liquids, suspensions and the like.

"Dosing regimen" means the dose of a drug taken at a first time by a patient and the interval (time or symptomatic) and dosage amounts at which any subsequent doses of the drug are taken by the patient. Each dose may be of the same or a different dosage amount.

A "dose" means the measured quantity of a drug to be taken at one time by a patient.

"Delayed release" or "DR" refers to dosage forms that delay the release of the active agent until the dosage form has passed through the stomach after oral administration; such as for example, delaying release of the agent such that not more than about 0% to 40% is released within about 1 hour to about 2 hours of being in an acidic aqueous environment (pH<5).

"Immediate release" or "IR" refers to dosage forms that are formulated to release an active drug immediately after oral administration; no deliberate effort is made to modify the drug release rate in immediate release dosage forms or formulations. Immediate-release products generally result in relatively rapid drug absorption and onset of accompanying pharmacodynamic effects. Immediate release dosage forms comprising a therapeutic agent include those, for example, that release about 70% to about 100% of the therapeutic agent after about 5 minutes to about 60 minutes of being ingested, or in an aqueous buffer.

"Methacrylates" refers to derivatives of methacrylic acid.

"Modified release" or "MR" dosage forms refers to a mechanism that (in contrast to immediate-release dosage forms) delivers a drug with a delay after its administration (delayed-release dosage or "DR") or for a prolonged period of time including suspended release ("SR") as outlined below and extended-release ("ER", "XR", "XL") dosages or to a specific target in the body (targeted-release dosage); it is meant to include any dosage form or formulation which is not an immediate release dosage form or formulation including those described in Chapter 17 of "Applied Biopharmaceutics and Pharmacokinetics", Sixth Edition; Shargel et al., which is incorporated herein by reference; thus for the purposes herein, MR also includes "sustained release" or "SR" dosage forms and "extended release" or "ER" dosage forms and "delayed release" or "DR" dosage forms.

"Non-acidic aqueous solution" or "non-acidic aqueous buffer" means a solution or buffer with pH>5.

A "patient" means a human in need of medical treatment. In one embodiment medical treatment can include treatment of an existing condition, such as a disease or disorder, prophylactic or preventative treatment, or diagnostic treatment. In another embodiment, medical treatment also includes administration to treat therapeutic categories, including excessive daytime sleepiness, cataplexy, sleep paralysis, apnea, narcolepsy, sleep time disturbances, hypnagogic hallucinations, sleep arousal, insomnia, and nocturnal myoclonus.

"Paracetamol" also known as "N-acetyl-p-aminophenol", "acetaminophen" and/or "APAP" is an analgesic and antipyretic agent and is widely used in prescription and non-prescription medicines.

"Polymethacrylate" or "Poly(methacrylic acid)" or "PMAA" means a polymer made from methacrylic acid.

"Providing" means giving, administering, selling, distributing, transferring (for profit or not), manufacturing, compounding, or dispensing.

"Side effect" means a secondary effect resulting from taking a drug. The secondary effect can be a negative (unfavorable) effect (i.e., an adverse side effect) or a positive (favorable) effect.

"Sustained release" or "SR" refers to dosage forms designed to release (liberate) a drug at a predetermined rate in order to maintain a constant drug concentration for a specific period of time with minimum side effects.

Pharmacokinetic parameters referred to herein describe the in vivo characteristics of drug (or a metabolite or a surrogate marker for the drug) over time. These include plasma concentration (C), as well as $C_{max}$, $C_n$, $C_{24}$, $T_{max}$, $AUC_{0-t}$ and $AUC_{0-inf}$.

The term "$T_{max}$" refers to the time from drug administration until $C_{max}$ is reached. "AUC" is the area under the curve of a graph of the measured plasma concentration of an active agent vs. time, measured from one time point to another time point. For example AUC.sub.0-t is the area under the curve of plasma concentration versus time from time 0 to time t, where time 0 is the time of initial administration of the drug. Time t can be the last time point with measurable plasma concentration for an individual formulation. The $AUC_{0-\infty}$, or $AUC_{0-INF}$ is the calculated area under the curve of plasma concentration versus time from time 0 to time infinity. In steady-state studies, $AUC_{0-t}$ is the area under the curve of plasma concentration over the dosing interval (i.e., from time 0 to time τ (tau), where tau is the length of the dosing interval.

It may be advantageous to incorporate a pharmacy management system into the method of the present invention. "Pharmacy management systems" are computer-based systems that are used by commercial pharmacies to manage prescriptions and to provide pharmacy and medical personnel with warnings and guidance regarding drugs being administered to patients. Such systems typically provide alerts warning either or both of health care providers and patients when a drug that may be harmful to the particular patient is prescribed. For example, such systems can provide alerts warning that a patient has an allergy to a prescribed drug, or is receiving concomitant administration of a drug that can have a dangerous interaction with a prescribed drug. In some cases it may provide a warning to a patient who is known or suspected of abusing alcohol when administration of the drug with alcohol is potentially dangerous. U.S. Pat. Nos. 7,895,059; 7,797,171; 7,668,730; 7,765,106; 7,765,107; 5,758,095, 5,833,599, 5,845,255, 6,014,631, 6,067,524, 6,112,182, 6,317,719, 6,356,873, 7,072,840, and 8,731,963 each of which is incorporated herein by reference, disclose various pharmacy management systems and aspects thereof. Example pharmacy management systems are now commercially available, e.g., CENTRICITY Pharmacy from BDM Information Systems Ltd., General Electric Healthcare, Waukesha, Wis., Rx30 Pharmacy Systems from Transaction Data Systems, Inc., Ocoee, Fla., SPEED SCRIPT from Digital Simplistics, Inc., Lenexa, Kans., and various pharmacy management systems from OPUS-ISM, Hauppauge, N.Y.

In some embodiments, a pharmacy management system may be required or preferred as part of a drug distribution program. For example, the present invention includes a method for distributing a drug containing GHB or a salt thereof to an approved pharmacy, the method comprising: (1) Identifying an approved pharmacy that has an established management system to dispense information concerning the risks associated with ingesting alcohol concomitantly to said drug to patients that are prescribed said drug; (2) Providing said pharmacy with said information related to the risks; and (3) Authorizing distribution of said drug to said pharmacy, wherein said pharmacy dispenses the drug with said information when filling a prescription for said drug. The established management system may include an electronic alert to employees to dispense said information with said drug when prescriptions are filled. Such information may be dispensed in written form, for example in a brochure explaining the risks of concomitant ingestion of GHB and alcohol. For example, the information dispensed with GHB may advise a patient of the potential for enhanced potency of GHB if the patient also co-ingests alcohol. Alternatively, or in addition thereto, the information dispensed with GHB may advise a patient of the potential for decreased potency of GHB if the patient also co-ingests alcohol. Such information may also be dispensed in verbal form. Distributors may maintain a directory of approved pharmacies, for example in a computer readable storage medium, to further ensure that GHB is dispensed only to patients who are advised of the additive effects.

In addition, the system can prevent the dispensing of GHB or salt thereof until proper testing or confirmation is obtained that the patient is not taking or going to take large amounts of alcohol concomitantly with GHB, as may be expected with some who suffers from alcoholism. Alternatively, the patient can be warned of the adverse effect and instructed to modify or skip the dose of GHB to accommodate the increased or reduced effects of GHB due to alcohol use. 1001271A pharmacy management system of the present invention can be a REMS system as shown in U.S. Pat. Nos. 7,895,059; 7,797,171; 7,668,730 and 8,731,963. Warnings may be administered through the existing pharmacy management system as described in the patents above.

Therapeutic Agents

There are a number of therapeutic agents that can be used with alcohol-resistant formulations of the invention, including those approved drugs already cited by the FDA as requiring a test for alcohol induced dose dumping. In addition, products which are part of an ANDA application and requiring a test for alcohol induced dose dumping are also included. In response to the FDA's concerns about the safety issue of alcohol induced dose dumping, the Division of Bioequivalence (DBE), in the Office of Generic Drugs, Center for Drug Evaluation and Research, US-FDA adopted a policy of requesting information on in vitro dose dumping in the presence of alcohol in its review of ANDA applications for certain classes of modified release (MR) or modified release drug products, for example all MR opioid products. The DBE's current policy is to request that ANDA applicants perform an in vitro dose dumping in alcohol test on a particular generic product if the approval package for the corresponding RLD shows that in vitro dose dumping in alcohol test results were requested by the agency for the New Drug Application (NDA) for the product. The drug products for which the DBE requests the in vitro dose dumping in alcohol test can be located in FDA's Guidance for Industry, Individual Products Bioequivalence Recommendations Guidances, and all of which may be considered for use in alcohol resistant formulations of the invention. In addition, the National Institute of Health (NIH) Publication No. 13-5329 (Published 2003; Revised 2014 and incorporated herein by reference) from the National Institute on Alcohol and Alcoholism discusses "Harmful Interactions Mixing Alcohol with Medicines" and lists a number of drugs which are contraindicated with alcohol and all of which may be considered for use with alcohol resistant formulations of the invention.

In some embodiments the therapeutic agent is present as a prodrug or drug conjugate. In one embodiment, a drug for use in the invention is an opioid or an opiate. In some embodiments, a drug for use in the invention is selected from morphine, hydrocodone, oxycodone, fentanyl, sufentanyl, codeine, tapentadol, tramadol, meperidine, 3,4-Methylenedioxymethamphetamine, paracetamol, codeine, oxycodone and GHB. In specific embodiments, a drug for use in the invention is GHB.

Gamma Hydroxybutyrate (GHB)

GHB (also called oxysorbate or oxybate) is approved in the United States (US) for the treatment of excessive daytime sleepiness (EDS) and for the treatment of cataplexy, both in patients with narcolepsy. GHB is commercially sold as Xyrem® sodium oxybate by Jazz Pharmaceuticals. "GHB", oxybate, a GHB salt or Xyrem® will be used to refer to these active forms. In some embodiments, GHB can exist as individual sodium, calcium, potassium, or magnesium salts and can also exist as a mixture of two or more of these salts. See U.S. Pat. No. 8,591,922 which is incorporated herein by reference in its entirety.

In certain embodiments, the mixed salt oxybate comprises varying percentages of oxybate, expressed as % molar equivalents (% mol. equiv.) of Na.GHB, K.GHB, Mg.(GHB)$_2$, and/or Ca.(GHB)$_2$. The terms "% molar equivalents" and "% mol. equiv.," as used herein, refer to molar composition of salts expressed as a percent of GHB equivalents. Those skilled in the art will understand that as each GHB unit is considered to be one molar equivalent, the monovalent cations, Na$^+$ and K$^+$, have one molar equivalent per salt, and the divalent cations, Mg$^{+2}$ and Ca$^{+2}$, have two molar equivalents per salt. See U.S. Pat. Nos. 8,591,922; 8,901,173; 9,132,107; 9,555,017; 10,195,168 for amounts of % mol. equiv. useful in the present disclosure.

In some embodiments, any of the salts, such as the Na. GHB salt, the K.GHB salt, the Mg.(GHB)$_2$ salt or the Ca.(GHB)$_2$, is present in about 1%-5%, about 5%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, about 90%-95%, or about 95%-100% (% mol. equiv.). In some embodiments, the Na. GHB salt is present in a % mol. equiv. of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (% mol. equiv.). In some embodiments, the Na. GHB salt is absent.

In some embodiments, where the mixed salt oxybate comprises a mixture of Na.GHB, K.GHB, Mg.(GHB)$_2$, and Ca.(GHB)$_2$, the Na.GHB salt is present in a % mol. equiv. of about 1%-15%, 5%-10%, or about 8%; the K.GHB salt is present in a % mol. equiv. of about 10%-30%, 15%-25%, or about 23%; the Mg.(GHB)$_2$ salt is present in a % mol. equiv. of about 10%-30%, 15%-25%, or about 21%; and the Ca.(GHB)$_2$ salt is present in a % mol. equiv. of about 30%-60%, 40%-50, or about 48% (% mol. equiv.).

In some embodiments, the mixed salt oxybate comprises about 8% mol. equiv. of sodium oxybate, about 23% mol. equiv. of potassium oxybate, about 21% mol. equiv. of magnesium oxybate and about 48% mol. equiv. of calcium oxybate. In some embodiments, where the mixed salt oxybate comprises a mixture of Na. GHB, K.GHB, Mg.(GHB)$_2$, and Ca. (GHB)$_2$, wherein the mixture comprises Na. GHB, K.GHB, Mg. (GHB)$_2$, and Ca. (GHB)$_2$ salts are present in a % mol. equiv. ratio of about 8:23:21:48, respectively.

In some embodiments, where the pharmaceutical composition comprises a mixture of Na. GHB, K.GHB, and Ca.(GHB)$_2$, the Na. GHB salt is present in a % mol. equiv. of about 5%-40%, the K.GHB salt is present in a % mol. equiv. of about 10%-40%, and the Ca.(GHB)$_2$ salt is present in a % mol. equiv. of about 20%-80%.

Methods of making individual and mixed GHB salts are described, for example, in U.S. Pat. Nos 4,393,236, and 8,591,922 which are incorporated herein by reference.

GHB treatment substantially reduces the signs and symptoms of narcolepsy, i.e. excessive daytime sleepiness, cataplexy, sleep paralysis, apnea, narcolepsy, sleep time disturbances, hypnagogic hallucinations, sleep arousal, insomnia, and nocturnal myoclonus. In addition, GHB increases total sleep time and REM sleep, and it decreases REM latency (Mamelak et al, 1973; Yamada et al., 1967; Bedard et al., 1989), reduces sleep apnea (Scrima et al., 1987), and improves general anesthesia (Hasenbos and Gielen, 1985).

GHB has several clinical applications other than narcolepsy and sleep disorders. GHB has been reported to reduce alcohol craving, the number of daily drinks consumed, and the symptoms of alcohol withdrawal in patients (Gallimberti et al., 1989; Gallimberti et al., 1992; Gessa et al., 1992). GHB has been used to decrease the symptoms of opiate withdrawal, including both heroin and methadone withdrawal (Gallimberti et al., 1994; Gallimberti et al., 1993). It has analgesic effects that make it suitable as a pain reliever (U.S. Pat. No. 4,393,236). Intravenous administration of GHB has been reported to reduce intracranial pressure in patients (Strong, A. 1984). Also, administration of GHB was reported to increase growth hormone levels in patients (Gessa et al, 1994).

A good safety profile for GHB consumption, when used long term for treatment of narcolepsy has been reported. Patients have been safely treated for many years with GHB without development of tolerance (Scharf, 1985). Clinical laboratory tests carried out periodically on many patients have not indicated organ or other toxicities (Lammers, 1993; Scrima, 1990; Scharf, 1985; Mamelack, 1977; Mamelak, 1979; Gessa, 1992). The side effects of GHB treatment have been minimal in incidence and degree of severity, though they include sleepwalking, enuresis, headache, nausea and dizziness (Broughton and Mamelak, 1979; Mamelak et al., 1981; Mamelak et al., 1977; Scrima et al., 1989; Scrima et al., 1990; Scharf et al., 1985). Therefore, it is critical to identify GHB formulations that are resistant to alcohol to avoid accidental GHB dose dumping and the potential side effects that may come along with that and to maintain the positive safety profile for GHB.

GHB and Alcohol

GHB is a central nervous system (CNS) depressant. Alcohol and sedative hypnotics are contraindicated in patients who are using GHB. The concurrent use of GHB with other CNS depressants, including but not limited to opioid analgesics, benzodiazepines, sedating antidepressants or antipsychotics, general anesthetics, muscle relaxants, and/or illicit CNS depressants, may increase the risk of respiratory depression, hypotension, profound sedation, syncope, and death. If use of these CNS depressants in combination with GHB is required, dose reduction or discontinuation of one or more CNS depressants (including GHB) should be considered. In addition, if short-term use of an opioid (e.g. post- or perioperative) is required, interruption of treatment with GHB should be considered. See the package insert for Xyrem™.

GHB may impair respiratory drive, especially with overdoses associated with interactions with other drugs and alcohol. Prior to taking Xyrem, patients are educated on the risks of concomitant use of alcohol and a warning is also included on the label. GHB formulations such as Xyrem are most often taken just before sleep and if a patient has intentionally or unexpectedly ingested a large amount of alcohol, such as can occur on a 'binge night' of drinking, they ideally will skip their dose of GHB that night. However, alcohol is known to impair judgement and there may be instances where a patient is intoxicated to the point that they choose to take their GHB dose after drinking rather than skip it for that evening. It is therefore important to identify formulations that are resistant to alcohol induced dose dumping and/or that inhibit GHB release in increasing concentrations of alcohol. Understanding that moderate and even daily alcohol consumption may occur in patients taking GHB formulations, it is important to still allow modified release of GHB if the amount of alcohol co-ingested is minimal but then to rapidly inhibit release if the amount of alcohol increases.

In order to evaluate the alcohol resistance of pharmaceutical compositions, the United States Food and Drug Administration (FDA) suggests performing in vitro dissolution tests to compare the kinetics obtained in 0.1 N HCl medium (representative of gastric pH) with the kinetics obtained in the same medium substituted with 5%, 20% and 40% (v/v) ethanol. According to Walden et al. (The Effect of Ethanol on the Release of Opioids 30 from Oral Sustained-Release Preparations, Drug Development and Industrial Pharmacy, 33:10, 1101-1111, 2007; which is incorporated herein by reference in its entirety), the fact of exposing in vitro a pharmaceutical form over a period of 2 hours is regarded as representative of the exposure time of these pharmaceutical forms in vivo.

In addition, healthcare providers should caution patients about operating hazardous machinery, including automobiles or airplanes, until they are reasonably certain that GHB does not affect them adversely (e.g., impair judgment, thinking, or motor skills). Patients should not engage in hazardous occupations or activities requiring complete mental alertness or motor coordination, such as operating machinery or a motor vehicle or flying an airplane, for at least 6, 7, 8 or 9 hours after taking the last dose of GHB. Patients should be queried about potential adverse events, such as excessive daytime sleepiness, CNS depression related events, etc. upon initiation of GHB therapy and periodically thereafter. These queries should include info regarding additional complications, alcohol for example. See the Xyrem package insert which is incorporated by reference for all purposes.

In one embodiment described herein, patients are warned that combination of GHB with alcohol can exacerbate all the effects and adverse events associated with GHB. These effects include the intended effects of drowsiness, sedation, and sleep and typically unintended events such as depressed respiration, CNS depression, excessive drowsiness, hepatic impairment, and depression, among other things.

Another embodiment of the present invention is a method for treating a patient who is suffering from a disease or condition, or a symptom thereof, treatable with GHB, comprising: administering a salt of GHB or a salt thereof to a patient or determining whether the patient is currently on a GHB drug regimen; determining if the patient may also ingest alcohol; and advising a patient to cease ingestion of alcohol. In some embodiments, patients benefit from this directive when the patient has/will have renal impairment.

An essential objective of the present invention is thus to provide an alcohol rugged oral pharmaceutical form of at least one active ingredient, preferably GHB, making it possible to avoid or limit increased release of the active ingredient induced by the consumption of alcohol, either intentionally or accidentally, during the administration of this pharmaceutical form. It is also an object of the invention that the drug has a modified release profile. Preferably the modified release profile of the drug allows for once nightly, or once daily, administration of the drug.

Alcohol Resistant Dosage Forms

Formulations and dosage forms for the modified release of a drug in the presence or absence of alcohol are described herein. Formulations described herein are suited to the sustained, extended, delayed or controlled release of drugs, often at high doses, that are contraindicated with alcohol. In some embodiments, the formulations and dosage forms of the present invention can also include an immediate release component. The immediate release component can form part of a modified release unit dosage form or may be a separate immediate release composition. Multi-component dosage forms can comprise a mixture of modified release and immediate release components or a mixture of different modified release components with different release profiles. This mix-and-match system can be used to target unique PK profiles for different drugs as needed.

Immediate and modified release formulations for use in the invention, including materials and methods are shown for example in U.S. patent application number 2012/0076865, and U.S. Pat. Nos. 8,771,735, and 9,795,567, which are incorporated by reference in their entireties herein.

Modified release profiles are also described in (USP XXV, CDER, FDA, Rockville, Md.), extended release profiles are referenced by FDA Guidelines ("Extended Release Oral Dosage Forms: Development, Evaluation, and Application of In Vitro/In Vivo Correlations", Food and Drug Administration, CDER, Sep. 1997, Page 17), and immediate release profile are referenced by FDA guidelines ("Dissolution Testing of Immediate Release Solid Oral Dosage Forms", issued August 1997, Section IV-A), all of which are incorporated herein by reference in their entireties as well as the following patents, patent applications and other cited references.

Modified release dosage forms permit the release of the active ingredient over an extended period of time in an effort to maintain therapeutically effective plasma levels over similarly extended time intervals, improve dosing compliance, and/or to modify other pharmacokinetic properties of the active ingredient, such as delay onset of release or change conditions under which release occurs. Modified release formulations of the invention may provide a sustained release profile of the therapeutic agent in the absence of alcohol. Preferably, a sustained release profile provides not more than about 10% to about 50% release of the therapeutic agent within about 1 hour of being in an aqueous buffer, between about 20% to about 70% release within about 2 hours to about 4 hours of being in an aqueous buffer, and between about 50% to about greater than about 80% release within about 4 hours to about 10 hours of being in an aqueous buffer.

Modified release formulations of the invention may provide a delayed release profile of the therapeutic agent in the absence of alcohol. Preferably, release of the therapeutic agent is delayed during gastric transit following ingestion. In specific embodiments, release of the therapeutic agent is delayed during gastric transit following ingestion and having not more than about 0% to 40% release of the therapeutic agent within about 1 hour to about 2 hours of being in an acidic aqueous buffer (pH<5). In other embodiments, release of the therapeutic agent is delayed during exposure to the acidic aqueous buffer (pH<5), and then release of the therapeutic agent increases after the formulation is subsequently exposed to a non-acidic (pH>5) aqueous solution such that release of the therapeutic agent increases to between about 50% to about 100% release within about 1 hour of being in said non-acidic aqueous solution; or to between about 10% to about 70% release within about 1 hour to about 4 hours of being in said non-acidic aqueous solution. In the dissolution testing guideline for modified release profiles, such as those used in the present invention, material dissolves over a period of time, and its dissolution is measured at given intervals during this period. A minimum of three time points is recommended and generally cover early, middle and late stages of the dissolution profile (see Guidance for Industry, SUPAC-MR: Modified Release Solid Oral Dosage Forms," Food and Drug Administration, CDER, September 1997). The preferred dissolution apparatus is USP apparatus I (basket) or II (paddle), used at recognized rotation speeds, e.g., 100 rpm for the basket and 50-75 rpm for the paddle.

Other modified or controlled release dissolution profiles as desirable for use in the invention are described in US 20120076865 incorporated herein.

Immediate release dosage forms are considered those that have not been engineered to modify or control the release of the active ingredient. Immediate release profiles typically provide between about 70% and about 100% release of the therapeutic agent after about 5 minutes to about 60 minutes of being in an aqueous buffer. Immediate release preferably provides dissolution profiles wherein greater than 90% of the drug included in the immediate release component is released from the immediate release component within the first hour after administration. In the dissolution testing guidelines, materials which dissolve at least 80% in the first 30 to 60 minutes in solution qualify as immediate release profiles. ("Dissolution Testing of Immediate Release Solid Oral Dosage Forms", issued August 1997, Section IV-A). Therefore, immediate release solid oral dosage forms permit the release of most, or all, of the active ingredient over a short period of time, such as 60 minutes or less, and make rapid absorption of the drug possible.

A multiphase release profile (i.e., a composition containing an immediate release component and at least one modified release component) may also be employed to attain one or more combinations of release rates to attain more specific therapeutic objectives such as a portion of drug releasing immediately, followed by an extended release of the remainder. In some embodiments, the formulations for use in the invention comprise a drug carrier core selected from irregular granules, regular granules, spheronized granules, nanoparticles, drug-loaded non-pareils, micro-particles, pellets, beads, mini-tablets, tablets and/or capsules (hard and/or soft gelatin). In some embodiments, the drug carrier core for use in the invention comprises drug crystals. Suitable cores are described in Aulton's 'Pharmaceutics—The Design and Manufacture of Medicines', Chapter 32 (Aulton and Taylor; Aulton's Pharmaceutics $4^{th}$ Edition, published Jun. 19, 2013) and Qiu Y., et al. 'Developing Solid Oral Dosage Forms', Chapters 33 and 34 (Qiu Y., et al., Developing Solid Oral Dosage Forms $1^{st}$ Edition; published Dec. 19, 2008), each of which is hereby incorporated by reference in its entity for all purposes.

In some embodiments, the drug carrier core can be the size and/or shape of a pellet, bead, mini-tablet or tablet.

In particular embodiments, the formulations for use in the invention comprise at least two drug carrier cores each comprising a core selected from granules, nanoparticles, micro-particles, pellets, mini-tablets, tablets and/or capsules (hard and/or soft gelatin). In certain embodiments, the formulations for use in the invention comprise at least two drug carrier cores wherein at least one core comprises drug crystals.

In certain embodiments, the formulations for use in the invention are provided as a unit dosage form selected from tablets, mini-tablets, capsules, caplets, beads, pellets, granules, sachets, crystals or powders. In some embodiments, the unit dosage form may be a liquid or suspension. It is generally understood that "tablets" are meant to be those of tablet dosage forms of the art which generally are in the range of 50 mg up to 2.0 gram. Tablets can include matrix tablets, osmotic tablets, bi-layer tablets, orally disintegrating tablets, effervescent tablets and lozenges. Minitablets or mini-tablets are known in the art to be around 5 to 50 mg and typically 1 to 5 mm or preferably 1.5 to 3 mm. It is understood that drug carrier cores of the invention may comprise particles which are less than 5 mg. It is also understood that in certain embodiments, drug carrier cores of the invention comprise particles that are from 10 to 5000 microns in diameter. Pellets are multiparticulate forms that typically range from 300 to 3000 microns, from 600 to 3000 microns or preferably from 800 to 1500 microns. Granules are smaller and typically made up of small, fine particles.

Solid dosage forms or drug carrier cores for use in the invention may be made by a number of techniques known in the art including, but not limited to, compression and granulation. In addition, smaller forms, such as for example, pellets (either coated or uncoated) can be compressed into a larger form, such as for example a tablet or pill of any size or shape using methods such as, for example, those described in U.S. Pat. No. 4,684,516 and Bodmeier, R.

(1997) European Journal of Pharmaceutics and Biopharmaceutics, 43(1), 1-8) which are incorporated herein by reference. Processes often used for making dosage forms of the invention also include wet granulation, dry granulation, extrusion and spheronization, hot melt extrusion, milling, sieving and blending.

An outer or external functional coating is typically applied to oral dosage forms in order to mask taste, odor or color; provide physical or chemical protection for the active ingredient/drug; control the release of the active ingredient from the formulation; protect the active ingredient from the harsh environment of the stomach (i.e. enteric coating); or protect the subject from unwanted gastrointestinal side effects. Prior to applying an external coating, a seal-coating (also referred to as a sub-coating) may first be applied. Sub-coatings can act to smooth the product surfaces, enhance the adherence of the final, outer coat, prevent migration of the drug from the core to the functional coat, and/or to protect the active ingredient from premature degradation. The present invention also shows that the outer functional coating can act to prevent or decrease alcohol-induced dose dumping. The type and/or thickness of the seal coat or the final coating(s) may be varied in order to alter product characteristics, such as dissolution. The external or functional coatings are targeted to be about 5-60% by weight (of the drug carrier core) and seal coats are targeted to be about 1-5%, preferably about 2%, by weight. Sub-coats are generally thought of as "non-functional" in that they are not utilized to control timing or placement of release of the active ingredient; however, it is considered that certain sub-coatings may act as such "functional" coatings. For the purpose of the present invention, "functional coatings" are intended to include enteric coatings, time-release coatings, pH-dependent coatings, ethanol rugged coatings, or other which control the timing or placement of release of the active ingredient. In some exemplified embodiments of the invention, the one or more separate coatings or layers of the functional coating together constitute about 40% or less, 30% or less, 20% or less, or 15% or less of the total dosage form targeted by weight. In preferred embodiments, the first functional coating is about 10-20% of the total dosage form targeted by weight. In other preferred embodiments, a second or outer functional coating is about 1-10% of the total dosage form targeted by weight.

Unless stated otherwise, the amount of coatings or layers described herein (the "coating weight") is expressed as the percentage weight gain provided by the coating, relative to the initial weight of the drug carrier core prior to the application of said coating. Thus, a 10% (w/w) coating weight refers to a coating which increases the weight of a drug carrier core by 10%. Further, if the drug carrier core already has one or more coatings, the weight of the next coating is based on the weight of the core and the first coating. Thus, for a drug carrier core comprising a 20% w/w functional coating disposed over a 5% (w/w) sub-coating which is disposed over a drug carrier core, the 5% (w/w) sub-coating on the drug carrier core would increase the weight of said core by 5% and the 20% (w/w) functional coating would increase the weight of the sub-coated drug carrier core by 20%.

Methods for coating any component of a solid dosage form including the core, matrix and/or final form include, for example, spray coating and pan coating; however, any known method in the art may be used. Such polymer coating methods are described in Remington, *The Science and Practice of Pharmacy*, 22$^{nd}$ Ed. 2013.

Coating materials for use in the invention, including ethylcellulose materials, may be readily commercially available, such as for example, ETHOCEL ethylcellulose polymers. Where ethylcellulose is used to form the functional coating, the physical characteristics of the coating composition and residual shell may be modified by adjusting the molecular weight of the ethylcellulose. For example, different grades of ethylcellulose, including, but not limited to, 4 cP, 7 cP, 10 cP, and 20 cP grades, may be used to achieve a coating composition having desired physical characteristics. Polymethacrylate polymers for use in coatings of the invention are readily commercially available, and include, for example, Eudragit RS and RL.

In certain embodiments of the invention, the formulation comprises a coated drug carrier core comprising a core comprising an active agent, a first coating disposed over the core, and an optional second coating disposed over the first coating. In certain embodiments, the first coating is present at about 5%-60% w/w, inclusive of all values and subranges therebetween, including, but not limited to, 5-10%, 5-15%, 5-20%, 5-25%, 5-30%, 5-35%, 5-40%, 5-45%, 5-50%, 5-55%, 10-15%, 10-20%, 10-25%, 10-30%, 10-35%, 10-40%, 10-45%, 10-50%, 10-55%, 10-55%, 10-60, 15-20%, 15-25%, 15-30%, 15-35%, 15-40%, 15-45%, 15-50%, 15-55%, 15-60%, 20-25%, 20-30%, 20-35%, 20-40%, 20-45%, 20-50%, 20-55%, 20-60%, 25-30%, 25-35%, 25-40%, 25-45%, 25-50%, 25-55%, 25-60%, 30-35%, 30-40%, 30-45%, 30-50%, 30-55%, 30-60%, 35-40%, 35-45%, 35-50%, 35-55%, 35-60%, 40-45%, 40-50%, 40-55%, 40-60%, 45-50%, 45-55%, 45-60%, 50-55%, 50-60%, 55-60% w/w; 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55% and 60%.

In certain embodiments of the invention, the formulation comprises a coated drug carrier core comprising a core comprising an active agent, a first coating disposed over the core, and a second coating, or "top coating" disposed over the first coating. In certain embodiments, the first coating is present at about 5%-40% w/w, inclusive of all values and subranges therebetween, and the second coating is present at about 1%-25% w/w, inclusive of all values and subranges therebetween.

In particular embodiments, the first coating is present at about 5-10%, 5-15%, 5-20%, 5-25%, 5-30%, 5-35%, 5-40%, to10-15%, 10-20%, 10-25%, 10-30%, 10-35%, 10-40%,15-20%, 15-25%, 15-30%, 15-35%, 15-40%,20-25%, 20-30%, 20-35%, 20-40%, 25-30%, 25-35%, 25-40%, 30-35%, 30-40%, or 35-40% w/w and the second coating is present at about 1%-5%, 1-7%, 1-10%, 1-15%, 1-20%, 1-25%, 2%-5%, 2-8%, 2-10%, 3%-5%, 3-8%, 3-10%, 3-12%, 4%-6%, 4-8%, 4-10%, 4-12%, 5-15%, 5-20%, 5-25%, 10-15%, 10-20%, 10-25%, 15-20%, 15-25%, or 20-25% w/w.

In other embodiments the first coating is present at about 5-10%, 5-12%, 5-15%, 5-20%, 5-25%, 7-12%, 7-15%, 7-20%, 7-25%, 10-15%, 10-17%, 10-20%, 10-25%, 12-15%, 12-17%, 12-20%, 12-25%, 15-17%, 15-20%, or 15-25%, w/w and the second coating is present at about 1%-5%, 1-7%, 1-10%, 2%-5%, 2-8%, 2-10%, 3%-5%, 3-8%, 3-10%, 4%-6%, 4-8%, 4-10%, 5-10%, 5-12%, 5-15%, 7-10%, 7-12%, 7-15%, 10-12% or 10-15% w/w.

In certain embodiments the first coating is present at about 5-15%, 5-20%, 7-15%, 7-17%, 7-20%, 10-15%, 10-17%, 10-20%, 12-15%, 12-17%, 12-20%, 15-17%, or 15-20% w/w, and the second coating is present at about 1-5%, 1-7%, 1-10%, 2-5%, 2-8%, 2-10%, 3-5%, 3-8%, 3-10%, 4-6%, 4-8%, 4-10%, or 5-10% w/w.

In particular embodiments the first coating is present at about 5-20%, 7-17%, 7-20%, 10-17%, 10-20%, 12-15%, 12-17%, 12-20%, 15-17%, or 15-20% w/w, and the second coating is present at about 1-5%, 1-7%, 2-5%, 2-8%, 3-5%, 3-8%, 4-6%, or 4-8% w/w. In certain embodiments, the first coating is present at about 5%, 6%, 7%, 8%, 9%, 10%, 11%, 12%, 13%, 14%, 15%, 16%, 17%, 18%, 19%, 20%, 21%, 22%, 23%, 24%, or 25% w/w, and the second coating is present at about 1%, 2%, 3%, 4%, 5%, 6%, 7%, 8%, 9%, 10%, 11%, 12%, 13%, 14% or 15% w/w.

In certain embodiments, the first coating is present at about 5-30% w/w and the second coating is present at about 1-15% w/w. In particular embodiments, the first coating is present at about 5-25% w/w and the second coating is present at about 1-10% w/w. In other embodiments, the first coating is present at about 10-30% w/w and the second coating is present at about 3-15% w/w. In yet other embodiments, the first coating is present at about 10-25% w/w and the second coating is present at about 3-10% w/w. In still other embodiments, the first coating is present at about 10-20% w/w and the second coating is present at about 3-8% w/w.

In other embodiments, the first coating is present at about 10% w/w and the second coating is present at about 3% w/w. In yet other embodiments, the first coating is present at about 12% w/w and the second coating is present at about 3% w/w. In still other embodiments, the first coating is present at about 15% w/w and the second coating is present at about 3% w/w. In certain embodiments, the first coating is present at about 17% w/w and the second coating is present at about 3% w/w. In particular embodiments, the first coating is present at about 20% w/w and the second coating is present at about 3% w/w. In other embodiments, the first coating is present at about 25% w/w and the second coating is present at about 3% w/w. In yet other embodiments, the first coating is present at about 10% w/w and the second coating is present at about 5% w/w. In still other embodiments, the first coating is present at about 12% w/w and the second coating is present at about 5% w/w. In certain embodiments, the first coating is present at about 15% w/w and the second coating is present at about 5% w/w. In particular embodiments, the first coating is present at about 17% w/w and the second coating is present at about 5% w/w. In other embodiments, the first coating is present at about 20% w/w and the second coating is present at about 5% w/w. In yet other embodiments, the first coating is present at about 25% w/w and the second coating is present at about 5% w/w. In still other embodiments, the first coating is present at about 10% w/w and the second coating is present at about 8% w/w. In particular embodiments, the first coating is present at about 12% w/w and the second coating is present at about 8% w/w. In certain embodiments, the first coating is present at about 15% w/w and the second coating is present at about 8% w/w. In other embodiments, the first coating is present at about 17% w/w and the second coating is present at about 8% w/w. In yet other embodiments, the first coating is present at about 20% w/w and the second coating is present at about 8% w/w. In still other embodiments, the first coating is present at about 25% w/w and the second coating is present at about 8% w/w. In particular embodiments, the first coating is present at about 10% w/w and the second coating is present at about 10% w/w. In certain embodiments, the first coating is present at about 12% w/w and the second coating is present at about 10% w/w. In other embodiments, the first coating is present at about 15% w/w and the second coating is present at about 10% w/w. In yet other embodiments, the first coating is present at about 17% w/w and the second coating is present at about 10% w/w. In still other embodiments, the first coating is present at about 20% w/w and the second coating is present at about 10% w/w. In certain embodiments, the first coating is present at about 25% w/w and the second coating is present at about 10% w/w.

In certain embodiments, the first coating comprises a blend of cellulose and polymethacrylate polymers at a ratio of about 1:3 to 3:1 and is present at about 5-30% w/w and the second coating comprises a blend of cellulose and polymethacrylate polymers at a ratio of about 1:3 to 3:1 and guar gum (guar gum added at 1-10% w/w of the cellulose polymer) and the second coating is present at about 1-15% w/w. In particular embodiments, this first coating is present at about 5-25% w/w and this second coating is present at about 1-10% w/w. In other embodiments, this first coating is present at about 10-30% w/w and this second coating is present at about 3-15% w/w. In yet other embodiments, this first coating is present at about 10-25% w/w and this second coating is present at about 3-10% w/w. In still other embodiments, this first coating is present at about 10-20% w/w and this second coating is present at about 3-8% w/w. In further embodiments, the cellulose polymer is ethylcellulose and the polymethacrylate polymer is methacrylic acid-ethyl acrylate co-polymer 1:1. In further embodiments the ethylcellulose and the methacrylic acid-ethyl acrylate co-polymer are present at a weight ratio of 3:1 to 1:3. In further embodiments, the ethylcellulose and the methacrylic acid-ethyl acrylate co-polymer are present at a weight ratio of 1:2. In other further embodiments, the ethylcellulose and the methacrylic acid-ethyl acrylate co-polymer are present at a weight ratio of 1:1. In still other further embodiments, the ethylcellulose and the methacrylic acid-ethyl acrylate co-polymer are present at a weight ratio of 2:1. In particular embodiments, both the first and second coating comprise a blend of ethylcellulose and the methacrylic acid-ethyl acrylate co-polymer at a weight ratio of 1:1, and the second coating comprises guar gum at 2-8% w/w of ethylcellulose. In other embodiments, the first coating comprises a blend of ethylcellulose and the methacrylic acid-ethyl acrylate co-polymer at a weight ratio of 1:2, and the second coating comprise a blend of ethylcellulose and the methacrylic acid-ethyl acrylate co-polymer at a weight ratio of 1:1 and guar gum at 2-8% w/w of ethylcellulose. In other embodiments, the first coating comprises a blend of ethylcellulose and the methacrylic acid-ethyl acrylate co-polymer at a weight ratio of 1:1, and the second coating comprise a blend of ethylcellulose and the methacrylic acid-ethyl acrylate co-polymer at a weight ratio of 1:2 and guar gum at 2-8% w/w of ethylcellulose. In other embodiments, the first coating comprises a blend of ethylcellulose and the methacrylic acid-ethyl acrylate co-polymer at a weight ratio of 2:1, and the second coating comprise a blend of ethylcellulose and the methacrylic acid-ethyl acrylate co-polymer at a weight ratio of 1:1 and guar gum at 2-8% w/w of ethylcellulose. In other embodiments, the first coating comprises a blend of ethylcellulose and the methacrylic acid-ethyl acrylate co-polymer at a weight ratio of 1:1, and the second coating comprise a blend of ethylcellulose and the methacrylic acid-ethyl acrylate co-polymer at a weight ratio of 2:1 and guar gum at 2-8% w/w of ethylcellulose.

In other embodiments, the first coating comprises a blend of cellulose and polymethacrylate polymers at a ratio of about 1:3 to 3:1 and is present at about 10-25% w/w and the second coating comprises a blend of cellulose and polymethacrylate polymers at a ratio of about 1:3 to 3:1 and guar gum at 1-10% w/w of the cellulose polymer and is present at about 3-10% w/w. In other embodiments, this first coating is present at about 10% w/w and this second coating is present at about 3% w/w. In yet other embodiments, this first coating is present at about 12% w/w and this second coating is present at about 3% w/w. In still other embodiments, this first coating is present at about 15% w/w and this second coating is present at about 3% w/w. In certain embodiments, this first coating is present at about 17% w/w and this second coating is present at about 3% w/w. In particular embodiments, this first coating is present at about 20% w/w and this second coating is present at about 3% w/w. In other embodiments, this first coating is present at about 25% w/w and this second coating is present at about 3% w/w. In yet other embodiments, this first coating is present at about 10% w/w and this second coating is present at about 5% w/w. In still other embodiments, this first coating is present at about 12% w/w and this second coating is present at about 5% w/w. In certain embodiments, this first coating is present at about 15% w/w and this second coating is present at about 5% w/w. In particular embodiments, this first coating is present at about 17% w/w and this second coating is present at about 5% w/w. In other embodiments, this first coating is present at about 20% w/w and this second coating is present at about 5% w/w. In yet other embodiments, this first coating is present at about 25% w/w and this second coating is present at about 5% w/w. In still other embodiments, this first coating is present at about 10% w/w and this second coating is present at about 8% w/w. In particular embodiments, this first coating is present at about 12% w/w and this second coating is present at about 8% w/w. In certain embodiments, this first coating is present at about 15% w/w and this second coating is present at about 8% w/w. In other embodiments, this first coating is present at about 17% w/w and this second coating is present at about 8% w/w. In yet other embodiments, this first coating is present at about 20% w/w and this second coating is present at about 8% w/w. In still other embodiments, this first coating is present at about 25% w/w and this second coating is present at about 8% w/w. In particular embodiments, this first coating is present at about 10% w/w and this second coating is present at about 10% w/w. In certain embodiments, this first coating is present at about 12% w/w and this second coating is present at about 10% w/w. In other embodiments, this first coating is present at about 15% w/w and this second coating is present at about 10% w/w. In yet other embodiments, this first coating is present at about 17% w/w and this second coating is present at about 10% w/w. In still other embodiments, this first coating is present at about 20% w/w and this second coating is present at about 10% w/w. In certain embodiments, this first coating is present at about 25% w/w and this second coating is present at about 10% w/w. In further embodiments, the cellulose polymer is ethylcellulose and the polymethacrylate polymer is methacrylic acid-ethyl acrylate co-polymer 1:1. In yet further embodiments the ethylcellulose and the methacrylic acid-ethyl acrylate co-polymer are present at a weight ratio of 3:1 to 1:3. In further embodiments, the ethylcellulose and the methacrylic acid-ethyl acrylate co-polymer are present at a weight ratio of 1:2. In other further embodiments, the ethylcellulose and the methacrylic acid-ethyl acrylate co-polymer are present at a weight ratio of 1:1. In still other further embodiments, the ethylcellulose and the methacrylic acid-ethyl acrylate co-polymer are present at a weight ratio of 2:1. In particular embodiments, both the first and second coating comprise a blend of ethylcellulose and the methacrylic acid-ethyl acrylate co-polymer at a weight ratio of 1:1, and the second coating comprises guar gum at 2-8% w/w of ethylcellulose. In other embodiments, the first coating comprises a blend of ethylcellulose and the methacrylic acid-ethyl acrylate co-polymer at a weight ratio of 1:2, and the second coating comprise a blend of ethylcellulose and the methacrylic acid-ethyl acrylate co-polymer at a weight ratio of 1:1 and guar gum at 2-8% w/w of ethylcellulose. In other embodiments, the first coating comprises a blend of ethylcellulose and the methacrylic acid-ethyl acrylate co-polymer at a weight ratio of 1:1, and the second coating comprise a blend of ethylcellulose and the methacrylic acid-ethyl acrylate co-polymer at a weight ratio of 1:2 and guar gum at 2-8% w/w of ethylcellulose. In other embodiments, the first coating comprises a blend of ethylcellulose and the methacrylic acid-ethyl acrylate co-polymer at a weight ratio of 2:1, and the second coating comprise a blend of ethylcellulose and the methacrylic acid-ethyl acrylate co-polymer at a weight ratio of 1:1 and guar gum at 2-8% w/w of ethylcellulose. In other embodiments, the first coating comprises a blend of ethylcellulose and the methacrylic acid-ethyl acrylate co-polymer at a weight ratio of 1:1, and the second coating comprise a blend of ethylcellulose and the methacrylic acid-ethyl acrylate co-polymer at a weight ratio of 2:1 and guar gum at 2-8% w/w of ethylcellulose.

In certain embodiments, the first coating comprises a blend of two or more polymers. In some embodiments, the polymer blend comprises at least two polymers which are ethanol-soluble. In further embodiments, the first coating comprises a blend of least one polymer with pH-dependent dissolution and at least one polymer with pH-independent dissolution properties.

In some embodiments, the polymer blend comprises at least two polymers with pH-independent dissolution properties or at least two polymers with pH-dependent dissolution properties.

In some embodiments, the polymer with pH-independent dissolution properties is selected from ethyl cellulose and/or ethyl acrylate-methyl methacrylate co-polymer and/or ethyl acrylate-methyl methacrylate-trimethylammonioethyl methacrylate chloride co-polymer. In specific embodiments, the ethyl acrylate-methyl methacrylate-trimethylammonioethyl methacrylate chloride co-polymer is present at a ratio from about 1:2:0.1 to 1:2:0.2.

In some embodiments, the polymer with pH-dependent dissolution properties is selected from methacrylic acid ethyl acrylate co-polymer and/or butyl methacrylate-(2-dimethylaminoethyl) methacrylate-methyl methacrylate co-polymer and/or methacrylic acid methyl methacrylate co-polymer and/or methyl acrylate-methyl methacrylate-methacrylic acid co-polymer. In specific embodiments, the methacrylic acid-ethyl acrylate co-polymer is methacrylic acid-ethyl acrylate co-polymer 1:1.

In particular embodiments, the first coating comprises a blend of cellulose and polymethacrylate polymers. In further embodiments, the cellulose and polymethacrylate polymers are present at a ratio of about 50:1 to1:50, 25:1 to 1:25, 10:1 to 1:10, 5:1 to 1:5 3:1 to 1:3 or 2:1 to 1:2. In still further embodiments, the cellulose and polymethacrylate polymers are present at a weight ratio of about 3:1 to 2:3. In yet further embodiments, the cellulose and polymethacrylate polymers are present at a weight ratio of about 1:1.

In particular embodiments, the second coating comprises a single polymer (such as ethylcellulose) or a blend of at least two polymers (such as ethylcellulose and a polymethacrylate). In some embodiments, the second coating further comprises a polysaccharide gum such as acacia gum, guar gum, tragacanth gum or xanthan gum. In certain embodiments, the second coating is present at about 1%-50% w/w, inclusive of all values and subranges therebetween, e.g., about 1%-5%, 1-10%, 1-15%, 1-20%, 1-25%, 1-30%, 1-35%, 1-40%, 1-45%, 5-10%, 5-15%, 5-20%, 5-25%, 5-30%, 5-35%, 5-40%, 5-45%, 5-50%, 10-15%, 10-20%, 10-25%, 10-30%, 10-35%, 10-40%, 10-45%, 10-50%, 15-20%, 15-25%, 15-30%, 15-35%, 15-40%, 15-45%, 15-50%, 20-25%, 20-30%, 20-35%, 20-40%, 20-45%, 20-50%, 25-30%, 25-35%, 25-40%, 25-45%, 25-50%, 30-35%, 30-40%, 30-45%, 30-50%, 35-40%, 35-45%, 35-50%, 40-45%, 40-50%, 45-50%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45% and 50%.

In some embodiments, the drug carrier core further comprises a sub-coat or seal-coat which is applied prior to applying the first coating material as described above. In certain embodiments, the sub-coat or seal-coat comprises hydroxypropyl cellulose polymer. In specific embodiments, the sub-coat or seal-coat is applied, from an aqueous solution, to the drug carrier core to a target level of about 2-15% w/w, inclusive of all values and subranges therebetween, e.g., about 2-3%, 3-4%, 4-5%, 5-6%, 5-8%, 5-10%, 5-12%, 6-8%, 6-10%, 6-12%, 6-15%, 8-10%, 8-12%, 8-15%, 10-12%, and 10-15% w/w.

Additional excipients for use in dosage forms or drug carrier cores of the invention include, but are not limited to, binders, lubricants, glidants, disintegrants, diluents, coloring agents, suspension agents or flavoring agents, and the same excipient may be used for more than one function in a given formulation. Such excipients are described in Remington, *The Science and Practice of Pharmacy*, 22$^{nd}$ Ed. 2013, which is incorporated herein by reference in its entirety.

Other commonly used pharmaceutically acceptable excipients which may be suitable for use in the present invention include, but are not limited to, water, magnesium stearate, starch, lactose, microcrystalline cellulose, stearic acid, sucrose, talc, silicon dioxide, gelatin, acacia and dibasic calcium phosphate (Baldrick, P. (2000) Regul. Toxicol. Pharmacol. October 32(2):210; incorporated herein by reference.) Excipients are combined with active ingredients for example to enhance appearance, improve stability, aid processing or aid disintegration after administration, but many other excipient functions are known in the art that can be applied to oral dosage forms of the present invention. Classes of excipients which are often used and suitable for use in the present invention include but are not limited to, natural, modified-natural or synthetic mono-, oligo- or polysaccharides where oligo- and polysaccharides may or may not be physically or chemically crosslinked; natural, modified-natural or synthetic mono-, oligo- and polypeptides or proteins where oligo- and polypeptides and proteins may or may not be physically or chemically crosslinked; synthetic oligomers and polymers that may or may not be physically or chemically crosslinked; monomeric, hydrophobic, hydrophilic or amphoteric organic molecules; inorganic salts or metals; and combinations thereof. Accordingly, therapeutic agents used herein such as, for example, GHB, paracetamol, codeine or oxycodone may be combined with any excipient(s) known in the art that allows tailoring its performance during manufacturing, administration and/or its in vitro and in vivo performance.

Material which helps to hold the bulk of a product together and/or helps to maintain the product in a desired shape is known as a "binder" or "granulator". Binders suitable for use in the present invention are exemplified by, but are not limited to, sugars, gelatin, gums, microcrystalline cellulose and other modified celluloses, waxes or synthetic polymers like polyethylene glycol or polyvinyl pyrrolidone. Additional excipients often utilized in product formulations are lubricants. These are substances which aid in the manufacturing process as they help minimize clumping of the products and also help release them from the manufacturing machinery. A common "lubricant" used for pharmaceutical formulations is magnesium stearate; however, other commonly used product lubricants include talc, calcium stearate, stearic acid (stearin), hydrogenated vegetable oils, sodium benzoate, leucine, carbowax 4000 and sodium stearyl fumarate all of which may be suitable for use in the present invention. Glidants also referred to as "flow-aids", help to keep the powder or dry material of the products flowing as the products are being made, stopping them from forming lumps. Examples of commonly used glidants which may be suitable for use in the invention include colloidal silicon dioxide, talc, calcium silicate and magnesium silicate. Disintegrants are often added to pharmaceutical formulations to induce breakup of the product or dosage form (i.e. pellet or tablet) when it comes in contact with aqueous fluid in order to help release the drug. The objectives behind addition of disintegrants are to increase surface area of the product fragments and to overcome cohesive forces that keep these particles together in a formulation. They do this by promoting wetting and swelling of the dosage form so that it breaks up in the gastrointestinal tract. Some binders such as starch and cellulose also act as disintegrants. Other disintegrants are clays, cellulose derivatives, algins, gums and crosslinked polymers. Another group of disintegrants called "super-disintegrants" may be utilized. These materials are effective at low (2-5%) concentrations. "Super-disintegrants" which may be suitable for use in the present invention include, but are not limited to, sodium starch glycolate (SSG), croscarmellose sodium or crosprovidone.

It could be envisaged that a material or materials which help suspend a composition of the invention in a liquid, for example water, for administration could be used. Suspension agents (or viscosity modifying agents) suitable for use in the present invention are exemplified by, but are not limited to, acacia, agar, alginic acid, bentonite, calcium stearate, carbomers, carboxymethylcellulose calcium, carboxymethylcellulose sodium, carrageenan, cellulose (powdered), ceratonia, colloidal silicon dioxide, dextrin, gelatin, guar gum, hectorite, hydrophobic colloidal silica, hydroxyethyl cellulose, hydroxyethylmethyl cellulose, hydroxypropyl cellulose, hypromellose, kaolin, magnesium aluminium silicate, maltitol solution, medium-chain triglycerides, methylcellulose, microcrystalline cellulose, phospholipids, polycarbophil, polyethylene glycol, polyoxyethylene sorbitan fatty acid esters, potassium alginate, povidone, propylene glycol alginate, saponite, sesame oil, sodium alginate, sodium starch glycolate, sorbitan esters, sucrose, tragacanth, vitamin E polyethylene glycol succinate or xanthan gum.

pH adjusting agents may be used in the invention and can include acids, bases and many of the compounds/salts found in U.S. Pat. No. 8,263,650. In some embodiments the pH adjusting agent is an acid selected from the group of: acetic, acetylsalicylic, barbital, barbituric, benzoic, benzyl penicillin, boric, caffeine, carbonic, citric, dichloroacetic, ethylenediaminetetra-acetic acid (EDTA), formic, glycerophosphoric, glycine, lactic, malic, mandelic, monochloroacetic, oxalic, phenobarbital, phenol, picric, propionic, saccharin, salicylic, sodium dihydrogen phosphate, succinic, sulfadiazine, sulfamerazine, sulfapyridine, sulfathiazole, tartaric, trichloroacetic, and the like, or inorganic acids such as hydrochloric, nitric, phosphoric or sulfuric, and the like.

Preferably the pH adjusting agent should be a pharmaceutically acceptable acid as listed in the "Handbook of Pharmaceutical Salts: Properties, Selection and Use" (P. Stahl; John Wiley & Sons, Aug. 4, 2008; included herein by reference).

GHB is the preferred therapeutic agent for use in formulations of the invention. Typical concentrations of solid and liquid GHB formulations are shown in U.S. Pat. Nos. 8,263,650 and 8,324,275.

EXAMPLES

Example 1

Demonstrating Enteric Dissolution Behavior Using Ethylcellulose: methacrylic acid-ethyl acrylate copolymer at a ratio of 1:1 (% w/w)

Multi-particulate (pellet) drug carrier cores of calcium oxybate (monohydrate) were made by the process of extrusion-spheronisation. 17 g calcium oxybate (monohydrate), 1.4 g Avicel PH101, 0.6 g LH-31 and 0.6 g Klucel EF were weighed and added into the mixing bowl in Caleva Multi-lab for pre-blending for 1015 minutes at 100 RPM. The Klucel EF aqueous solution (9.6% or 8.3% w/w) was added slowly to the blend. The wet mass was well mixed for 15 minutes, during which time the mixer was stopped three to four times for visual checking and manual mixing. The wet mass was then moved to extruder and extruded through die plate with 1.0 mm or 0.8 mm pore size; the subsequent extrudate was rested at room temperature for 10 minutes before transferring into the spheronizer to be processed for 3-5 minutes at approximately 3000 RPM. The drug carrier cores (shaped like pellets) were collected and dried in the oven for 2 hours at 60° C. Final drug carrier core composition is given in Table 1 below.

TABLE 1

Composition of the calcium oxybate drug carrier (pellet) core

| Component | Quantity % |
|---|---|
| Ca Oxybate | 85.0 |
| Avicel PH101 | 7.0 |
| LH-31 | 3.0 |
| Klucel EF | 5.0 |
| Water* | q.s |

*removed during the pellet drying process

A binary polymer film coat consisting of a 1:1 (based on % w/w of polymer) mix of ethyl cellulose (EC) and Eudragit® L100-55 was applied to the drug carrier core described. The EC was used as the aqueous polymer dispersion, Aquacoat® ECD. The mixed polymer film was applied directly to the calcium oxybate pellet core.

Figure 1:
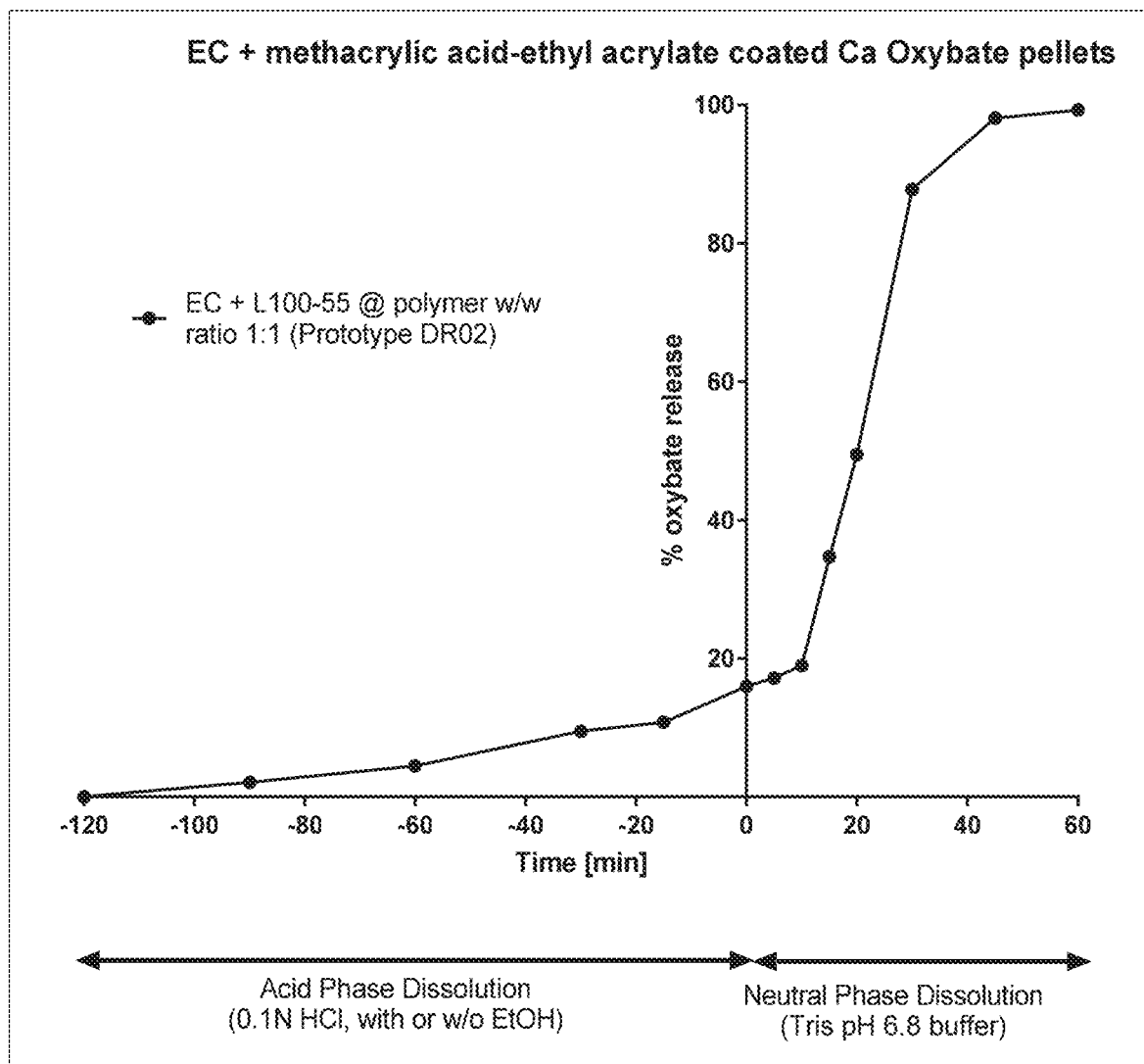
FIG. 1 is a graph showing the in vitro dissolution profile of calcium oxybate from a delayed release ("DR") pellet core having a polymer film of 30% w/w of the pellet core consisting of a mixture of ethylcellulose and poly(methacrylic acid-ethyl acrylate co-polymer). Dissolution was tested for 2 hours in acid (0.1N HCl) followed by 1 hour in Tris pH 6.8 buffer.

FIG. 1 shows the in vitro dissolution profile of calcium oxybate from a pellet having a polymer film of 30% w/w of the drug carrier core ("DR02"). Dissolution was tested for 2 hours in acid (0.1N HCl) followed by 1 hour in Tris pH 6.8 buffer. The data demonstrates the effectiveness of the polymer mix in suppressing dissolution in acid with rapid release at pH 6.8.

Example 2

Demonstrating Enteric Dissolution Behavior Using Ethylcellulose and an Alternate Preparation of methacrylic acid-ethyl acrylate Copolymer at a Polymer Blend Ratio of 1:1 (% w/w)

An alternative method of binary polymer film preparation to that presented in Example 1 was examined whereby the L-100-55 powder was replaced with the aqueous polymer dispersion, L30D-55 (i.e. mixing two colloidal polymer dispersions, Aquacoat® ECD+Eudragit® L30D-55). As per Example 1, the calcium oxybate pellet core was coated to a total polymer weight gain of 30% w/w (of the starter core eight). The coated-cores were tested for 2 hours in acid (0.1N HCl) followed by 1 hour in Tris pH 6.8 buffer.

Figure 2:
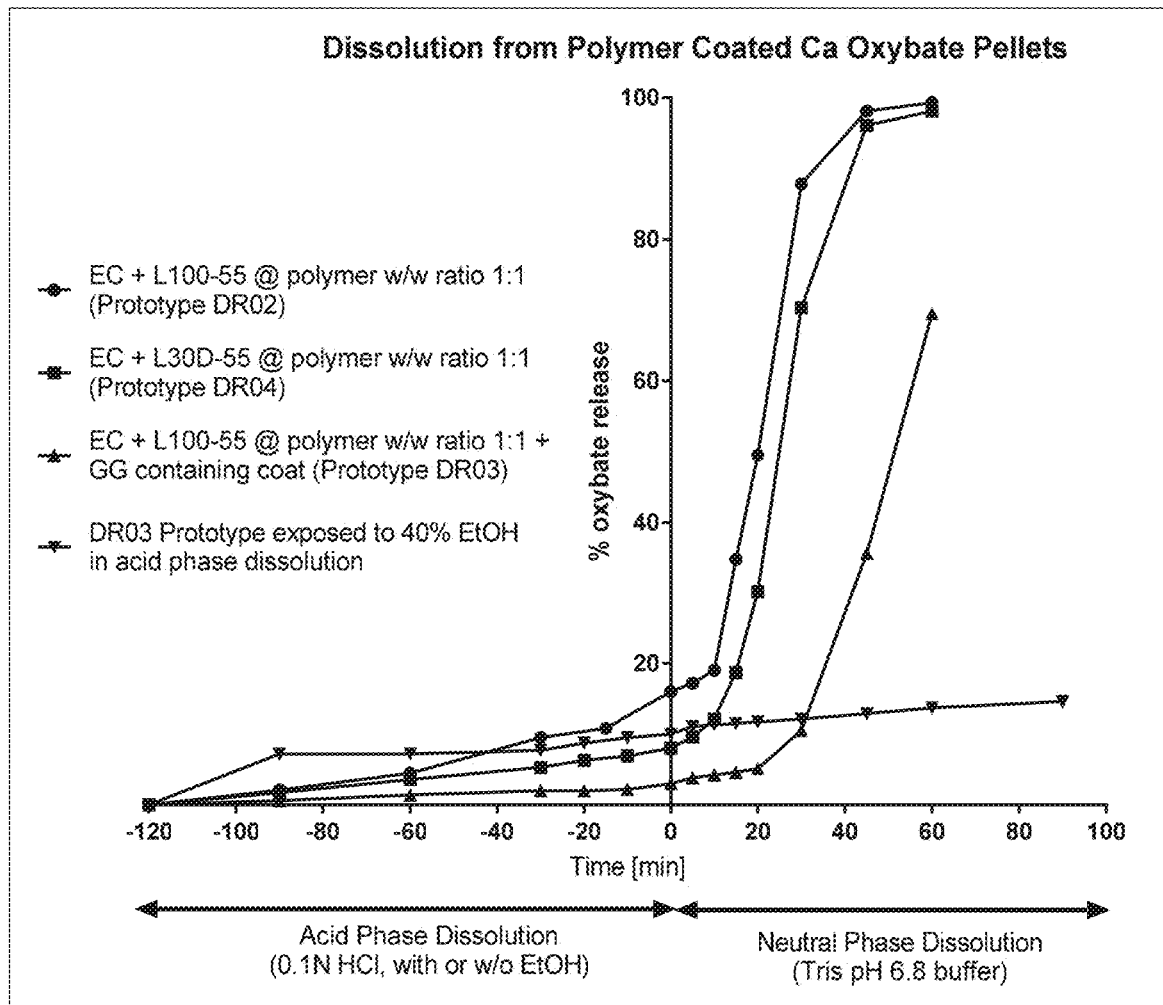
FIG. 2 is a graph showing the dissolution rate of calcium oxybate single-coated pellet cores coated using two different poly(methacrylic acid-ethyl acrylate co-polymer) sources (circles and squares). The polymethacrylate was mixed with ethylcellulose. Also shown is the dissolution rate of calcium oxybate from a double-coated formulation whereby the inner coat contains a mixture of ethylcellulose and methacrylic acid-ethyl acrylate co-polymer and guar gum is incorporated in the outer (surface) polymer coat. Calcium oxybate dissolution for the double-coated formulation was tested in the presence (inverted triangles) and absence (upright triangles) of 40% ethanol in the acid phase.

FIG. 2 shows the dissolution rate of pellet-shaped calcium oxybate drug carrier cores coated using the two different Eudragit® preparations. Comparing the powder form ("DR02"; circles) to the aqueous form ("DR04"; squares), it can be seen that similar dissolution profiles were obtained using either Eudragit L100-55 source.

Example 2A

Demonstrating Shut Down of Oxybate Release Following Exposure to Ethanol Via Gel Layer Formation. Bi-Layer Coating of EC:L100+EC:L100:GG (Guar Gum)

An additional polymer film layer incorporating the polysaccharide guar gum ("GG") was applied to the formulation of DR02 (described in Examples 1 and 2). This outer polymer film top coat consisted of EC:L100-55 at a 1:1 ratio and guar gum at a level of 5% w/w of the EC polymer content. The outer polymer film coat was applied to a level of 10% w/w of the pellet having the first polymer coating. The resulting pellets were tested for 2 hours in 0.1N HCl followed by 1 hour in Tris pH 6.8 buffer (USP 2, 37 C, 100 rpm, 300 mL). The dissolution profile of these bi-layer coated formulation is also shown in FIG. 2 (DR03, triangles) and is compared to that of the single layer coated formulations (DR02 (circles) and DR04 (squares)).

It can be seen that the additional polymer film on DR03 slows the dissolution rate in both acid and pH 6.8 buffers. Formulation DR03 was also tested for resistance to dissolution in the presence of ethanol as shown on the graph (inverted triangles). The most rigorous in vitro ethanol challenge as described in the FDA recommendations on evaluating formulation susceptibility to alcohol-induced dose dumping was applied, i.e. 2 hours exposure to 0.1N HCl containing 40% v/v ethanol. Surprisingly, as shown in FIG. 2, the rate of oxybate release following exposure to ethanol dramatically decreased.

Figure 3A:
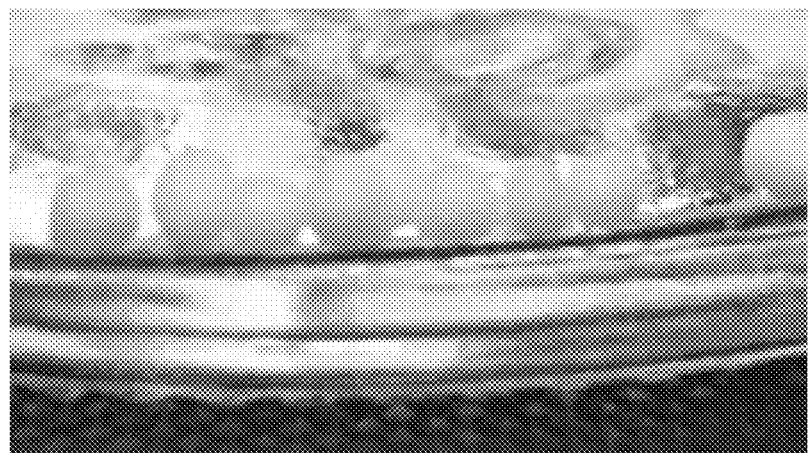
FIGS. 3A and 3B are images showing the presence and absence of a transparent gel layer around the calcium oxybate pellets "DR03" in the presence (3B) and absence (3A) of ethanol, respectively. The gel layer formation shown in the presence of ethanol is for calcium oxybate pellets having a double polymer film coat, whereby the inner coat contains a mixture of ethylcellulose and methacrylic acid-ethyl acrylate co-polymer and guar gum is incorporated in the outer (surface) polymer coat.
Figure 3B:
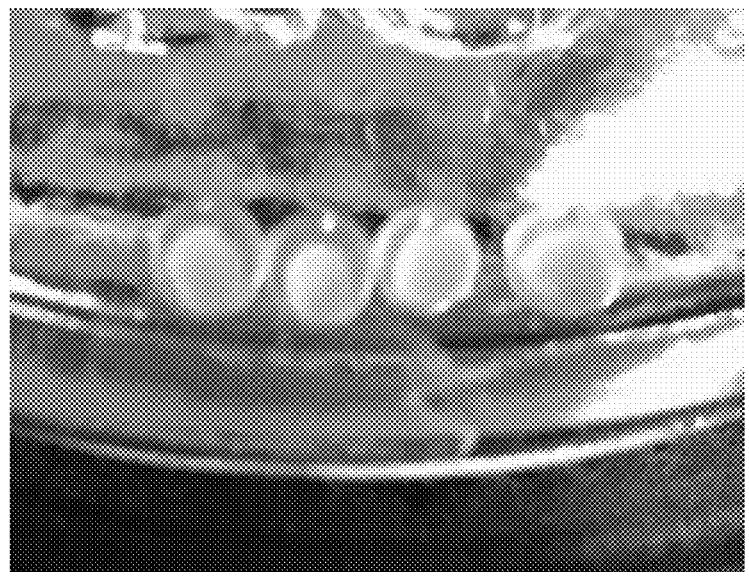

In addition, a transparent gel layer was observed to surround those pellets exposed to ethanol. As shown in FIGS. 3A and 3B, a gel layer surrounds the DR03 polymer coated pellets exposed to ethanol (FIG. 3B) whereas it is not present in those exposed only to 0.1N HCl (FIG. 3A). Such gel layer formation in the presence of ethanol has also been observed for GHB pellets having a single polymer coat containing ethylcellulose and methacrylic acid-ethyl acrylate co-polymer. Thus together this shows that upon inclusion of 40% v/v EtOH in the first acid phase dissolution test it is observed that the rate of oxybate release is suppressed following an initial release of approximately 10% oxybate, representing release during the period for the hydrogel to form around the pellet (as shown in FIG. 3), after which, oxybate release is suppressed.

Example 3

Demonstrating an Ethanol Concentration-Dependent Effect on Gel Layer Formation. Bi-Layer Coating of Calcium Oxybate Pellet Cores Using Binary EC+L30D-55 Polymers Guar Gum Incorporated in the Outer Polymer Film Coat (as Per Example 2A, DR03)

Pellet formulations were prepared as described above for DR03 with a binary EC:L30D-55 (1:1) polymer film coat, applied to a target 30% polymer weight gain (% w/w of the drug carrier core). An outer polymer film was then applied consisting of EC:L30D-55 (1:1) polymer mix plus guar gum (GG was used at a concentration of 5% w/w of the EC polymer content). This top coat was applied to a target 10% weight gain (% w/w of the drug carrier core pellet having the first polymer coat applied). Table 2 below contains a list of materials and equipment used to manufacture the formulations as described herein. The composition of the coating suspensions used for the inner layer and the outer guar gum layer is given in Table 3 also below:

TABLE 2

List of materials and equipment used for manufacture of prototypes

| Material/Equipment | Supplier/Manufacturer |
|---|---|
| Ethylcellulose (EC20) Aquacoat ECD (component I of II) | Colorcon Limited FMC |
| Aquacoat Guar gum (component II of II) | FMC |
| Eudragit L30D-55 | Evonik |
| Polyvinylpyrrolidone (PVP K30) | BASF |
| Dibutyl sebacate (DBS) | Sigma Aldrich |
| Deionised water | Elga water systems |
| 2-Propanol (IPA) | VWR |
| Mini-coater/Drier 2 with antistatic attachment | Caleva | without 10%, 20% or 40% ethanol as indicated, followed by testing in Tris pH 6.8 buffer as outlined below. The shorter 15 min exposure to 0.1N HCl/ethanol was used to better mimic in vivo conditions for co-ingestion of GHB and alcohol.

Figure 4:
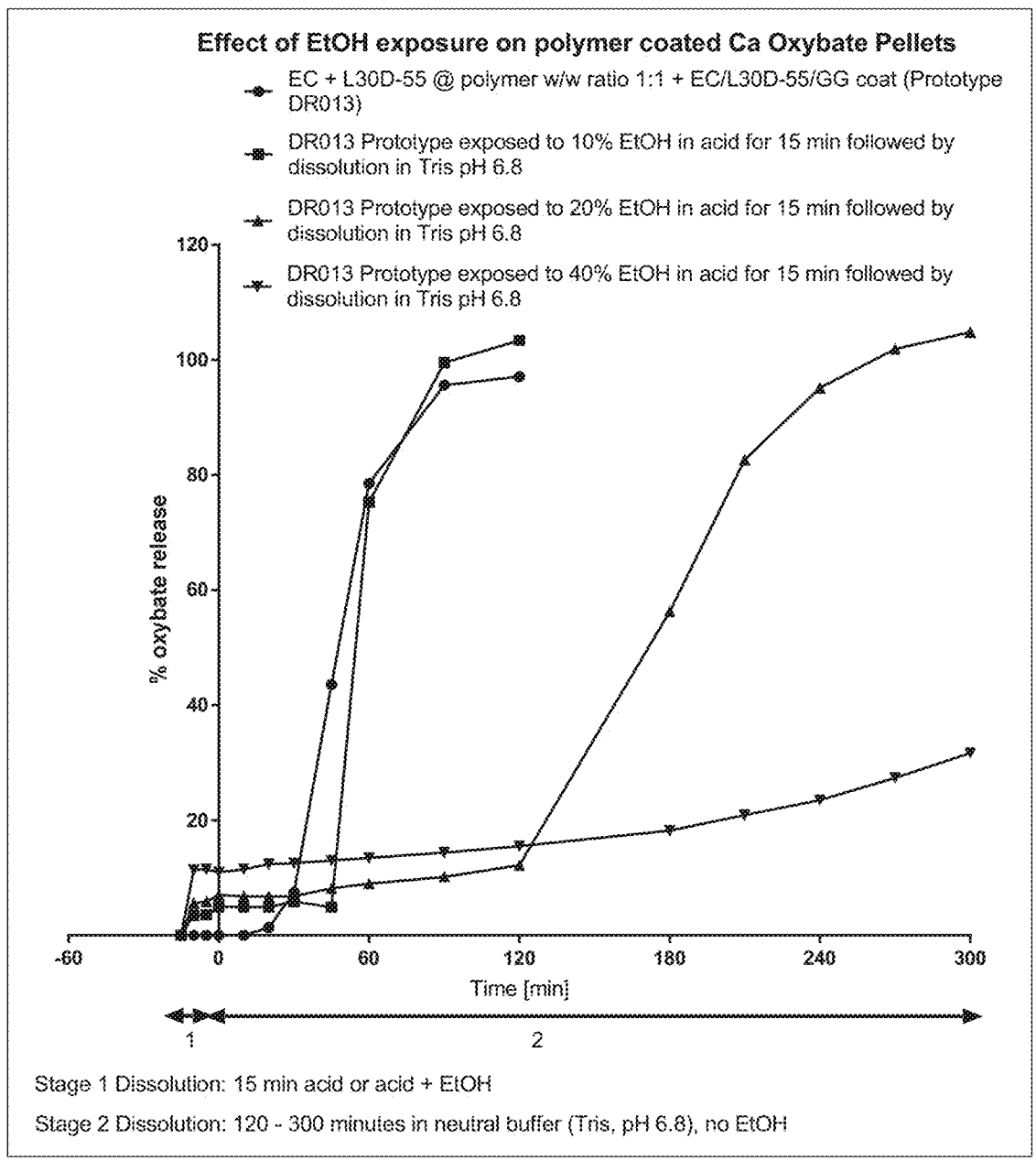
FIG. 4 is a graph showing the in vitro dissolution release profile of coated Calcium oxybate (GHB) pellets in Tris (pH 6.8) buffer following 15 minute pre-exposure to 0.1N HCl containing 0%, 10%, 20% or 40% v/v ethanol.

Thus the dissolution data in FIG. 4 generated over 15 minutes in 0.1N HCl (circles) represents more bio-relevant EtOH exposure time in stomach under fasted conditions with subsequent dissolution over 2 hours in Tris pH 6.8 buffer, representing passage through the small intestine. As shown, upon inclusion of 10% v/v EtOH in the 15 minute acid phase of the dissolution test (squares), it is observed that there is no impact to subsequent dissolution rate in the Tris pH 6.8 buffer. Upon inclusion of 20% v/v EtOH in the 15 minute acid phase of the dissolution test (triangles), it is observed that, following an initial 'burst' release of about 10% oxybate in 5 minutes, the subsequent dissolution rate in the Tris pH 6.8 buffer is repressed over a 2 hour period. Upon inclusion of 40% v/v EtOH in the 15 minute acid phase of the dissolution test (inverted triangles), it is observed that, following an initial 'burst' release of approximately 5% oxybate in 5 minutes, the rate of oxybate release is suppressed in the Tris pH 6.8 buffer. Importantly, the pellets begin to clump after 10-15 minutes in 0.1N HCl containing 20% v/v and 40% v/v ethanol (but not with 0% or 10% ethanol) and this clumping reflects the formation of the 'sticky' hydrogel layer. This accounts for the initial 10% oxybate burst release before the gel layer formation shuts down oxybate release.

To ascertain the strength of the gel layer formed following exposure to 20% and 40% ethanol, dissolution studies were extended for up to at least 5 hours (300 minutes) in Tris pH 6.8 as shown in FIG. 4. As seen, extending the Tris pH 6.8 buffer dissolution time beyond 2 hours demonstrates that the polymer coated drug carrier cores exposed to 20% v/v EtOH show a sharp inflection in the oxybate release rate after 2 hours, suggesting that the hydrogel has disintegrated, allowing oxybate dissolution, with 100% released within 4.5 hours. Surprisingly, for the polymer coated drug carrier cores exposed to 40% v/v EtOH, oxybate dissolution rate is significantly supressed even out to 6 hours, with only about 30% oxybate released. The dissolution data indicates that the rate and extent of hydrogel formation is EtOH concentration dependent.

TABLE 3

Composition of the coating solutions for Example 3a

| Coating | Function | Ingredient | Quantity based on dry polymer (%) | Quantity to be weighed (g) | Dry quantity (g) |
|---|---|---|---|---|---|
| EC + L30D-55 coating solution | Polymer | Aquacoat ECD | — | 41.67 | 12.501 |
| | Diluent | Water | — | 41.67 | — |
| | Polymer | Eudragit L30D-55 | — | 41.67 | 12.501 |
| | Diluent | Water | — | 50.83 | — |
| | | (14% polymer content) Total: 178.34 g | | | |
| Guar gum coating solution | Polymer | EC + L30D-55 coating solution | — | 100 | 15.422 |
| | Polymer | Guar gum | 0.0526* | 0.3689 | 0.3689 |
| | Diluent | Water | — | 40 | — |
| | | (<0.5% guar gum content**) Total: 140.3689 g | | | |

Figure 5A:
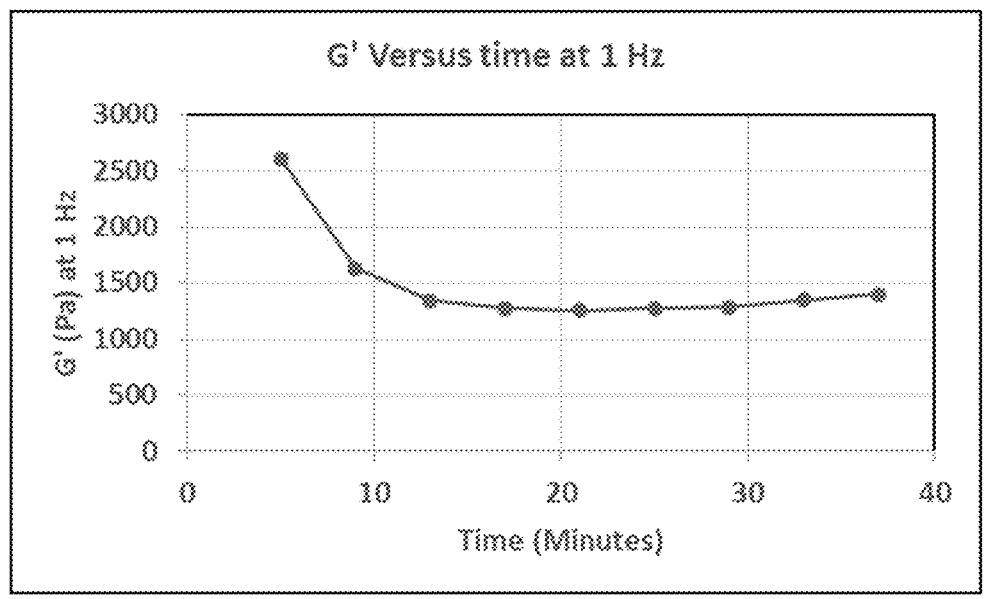
FIG. 5A is an image showing the variation in the shear storage modulus (elastic response, G') measured at a probe frequency sweep of 1 Hz over time following exposure of polymer coated placebo (sucrose) pellet cores (coated with a binary polymer mix of ethylcellulose & methacrylic acid-ethyl acrylate co-polymer (at a ratio (% w/w dry polymer) of 1:2) to 40% v/v EtOH in 0.1N HCl buffer.
Figure 5B:
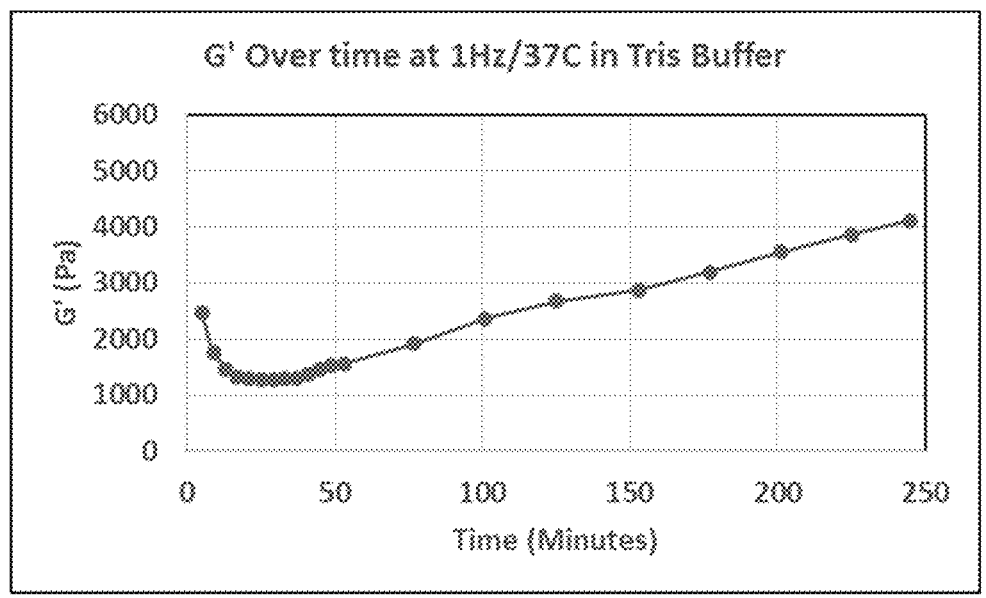
FIG. 5B shows the variation in the shear storage modulus (elastic response, G') measured at a probe frequency sweep of 1 Hz over time following transfer of polymer coated placebo (sucrose) pellet cores (coated with a binary polymer mix of ethylcellulose & methacrylic acid-ethyl acrylate co-polymer (at a ratio (% w/w dry polymer) of 1:2) from 0.1N HCl buffer containing 40% v/v EtOH to Tris pH 6.8 buffer (no EtOH).

*Corresponds to EC/gg = 95/5
**0.5% is the maximum recommended guar gum concentration The graph in FIG. 4 shows the dissolution data generated for the ethanol resilient polymer film system applied to calcium oxybate drug carrier cores (Prototype DR013), wherein the coated drug carrier cores, present as pellets, were tested for 15 minutes in 0.1N HCl, either with or Rheology studies on binary EC:L30D-55 polymer films applied to placebo (sucrose) pellet-shaped drug carrier cores support the dissolution findings. FIG. 5 presents the results of a study measuring the change in surface rheology of the binary polymer film coat following exposure to ethanol (40% v/v in 0.1N HCl buffer). The study indicates that an elastic gel, indicative of a hydrogel, is formed upon exposure to ethanol. The gel takes approximately 10-20 minutes to form and upon removal of the ethanol medium and transfer to non-ethanol containing medium (Tris pH 6.8 buffer), the hydrogel continues to form, increasing in gel strength over a 3 hour period. FIG. 5A shows the variation in the shear storage modulus (elastic response, G') measured at a probe frequency sweep of 1 Hz over time following exposure of polymer coated placebo (sucrose) pellet cores to 40% v/v EtOH in 0.1N HCl buffer. The curve shows that G' gives highest response during the first measurement, as expected as the gel coating is in it's infancy in terms of formation. This is followed by a drop in G', i.e. softening of the surface, over time for successive probe sweeps as the gel develop. A constant G' value is reached after approximately 20 minutes, indicating complete gel formation. FIG. 5B shows the variation in the shear storage modulus (elastic response, G') measured at a probe frequency sweep of 1 Hz over time following transfer of polymer coated placebo (sucrose) pellet cores from 0.1N HCl buffer containing 40% v/v EtOH to Tris pH 6.8 buffer (no EtOH). The graph shows that the initial G' value increases significantly following transfer from the EtOH containing buffer to the EtOH-free Tris buffer, from approximately 1,400 Pa at the end of the EtOH exposure phase to 2,500 Pa upon transfer to the Tris buffer. This indicates a rapid increase in gel mechanical strength. The gel then softens over the next 40 minutes to a minimum value of approximately 1200 Pa before increasing linearly over the next 3 hours to a final maximum measured value of approximately 4000 Pa, a significant increase in gel mechanical strength over time.

Example 4

The Effect on Release Rate of Altering the Composition of the Outer Polymer Film in Bi-Layer Coated Pellets The Examples above show that the addition of an outer polymer film coat consisting of EC/L100-55/GG helps to slow the rate of oxybate dissolution from the drug carrier core (here shaped as a pellet and thus also referred to as a "pellet core").

In an attempt to further reduce the effect of the outer polymer film on oxybate dissolution, the permeability of the outer coating was altered by adding the water soluble excipient, polyvinylpyrrolidone ("PVP"). Dissolution studies were performed as above both in the presence and absence of ethanol.

Figure 6:
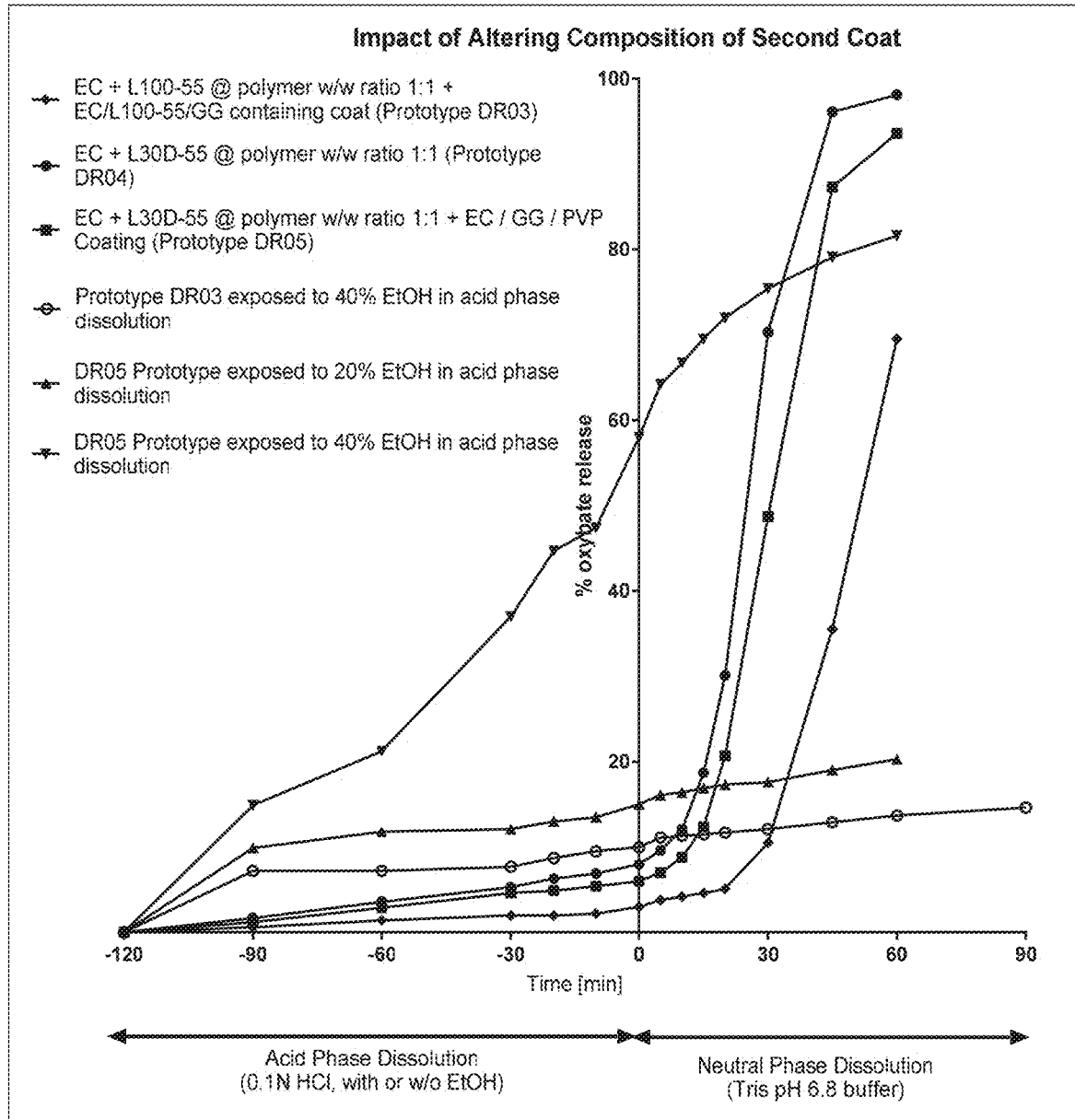
FIG. 6 is a graph showing the in vitro dissolution profile for GHB formulations both with (squares) and without (closed circles) an additional outer polymer film coat consisting of EC/L100-55/GG/polyvinylpyrrolidone ("PVP") when tested for 2 hours in acid (0.1N HCl) followed by 1 hour in Tris pH 6.8 buffer. Also shown is the dissolution of the double-coated GHB formulation when exposed to 40% v/v EtOH/acid buffer for 2 hours followed by 1 hour exposure to Tris pH 6.8 buffer without EtOH.

FIG. 6 is a graph showing the in vitro dissolution profile for GHB formulations both with and without the additional outer polymer film coat consisting of EC/L100-55/GG/polyvinylpyrrolidone ("PVP") when tested for 2 hours in acid (0.1N HCl), followed by 60-90 minutes in Tris pH 6.8 buffer. Also shown is the dissolution of the double-coated GHB formulation (DR05) when exposed to 20% and 40% EtOH/acid buffer for 2 hours followed by 1 hour exposure to Tris pH 6.8 buffer without EtOH. Comparison is made to DR03 and DR04, demonstrating the effect of outer film coat composition on the in vitro dissolution rate both in the absence and presence of EtOH. As shown in the graph, the PVP-containing formulation, DR05 (squares), produced pellets (coated drug carrier cores) with a similar dissolution rate as the single coated formulation (DR04; containing no top coat or PVP (closed circles)) and did not clump following exposure to 40% v/v ethanol (inverted triangles)). While DR05 prevented rapid oxybate release in HCL (squares), oxybate release increased upon ethanol exposure, but with only 14-18% oxybate released over 2 hours in 0.1N HCl/20% v/v ethanol and 55-60% oxybate released over 2 hours in 0.1N HCl/40% v/v ethanol.

Together the above results show that going from DR04 to DR03 (where a topcoat of EC/L100-55/GG was added) resulted in a reduced rate of drug release and the pellets clumped upon gel formation in the presence of ethanol. Further, when the outer topcoat composition was altered to increase permeability (through the addition of the water soluble polyvinylpyrrolidone) as with DR05 there was reduced clumping. The outer polymer film has limited impact on oxybate release rate in Tris pH 6.8 and also the pellets do not clump when exposed to 40% v/v ethanol. Rapid dose dumping is prevented in the presence of ethanol, with approximately 55-60% oxybate release over 2 hours in 0.1N HCl/40% v/v ethanol.

Example 5

Effect of Buffer Composition on Rate of GHB

Dissolution testing on the DR05 formulation described above was repeated using different post-HCL (i.e. non-acidic) buffers. Coated drug carrier cores, present as pellets, were tested for 2 hours in 0.1N HCl or EtOH/HCL followed by 1 hour in Tris pH 6.8 buffer ("TRIS"; USP 2, 37 C, 100 rpm, 300 mL) or 1 hour in pH 6.8 bicarbonate buffer.

Figure 7:
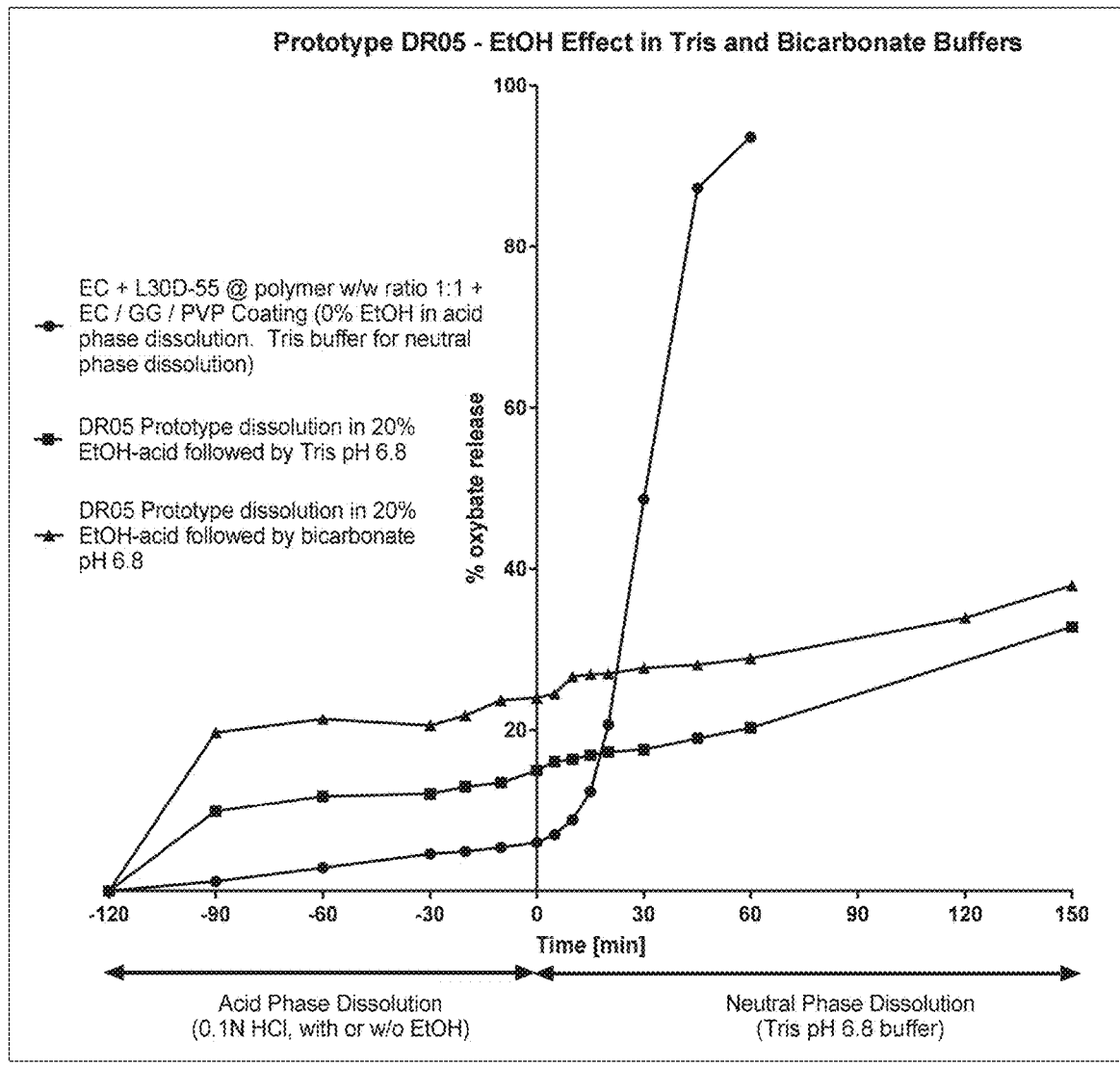
FIG. 7 is a graph comparing the in vitro dissolution profile for GHB formulations in either Tris or bicarbonate buffer post exposure to HCL buffers and in either the presence or absence of 20% v/v ethanol.

As shown in the graph in FIG. 7, the rate of GHB release after exposure to 20% ethanol was reduced in both the Tris-treated or bicarbonate-treated samples.

Example 6

Use of a Sub-Coat with Drug Carrier Cores Containing a Highly Water Soluble Drug Substance In order to analyze the impact of the use of a polymer sub-coat on the resultant dissolution profile of binary polymer film coated drug carrier cores, calcium oxybate pellet cores ("pellet cores") were prepared by extrusion-spheronisation to the same composition described in Table 1. A hydroxypropyl cellulose (HPC) polymer sub-coating was applied, from an aqueous solution, to the pellet cores to a target level of 8% w/w of the pellet core. A functional binary polymer film coat of ethylcellulose and methacrylic acid-ethylacrylate co-polymer (polymer ratio of 1:1) was then applied to a weight gain of 10% w/w of the sub-coated pellet core. The final functional film coat composition is as described for DR04 in Example 2.

Figure 8:
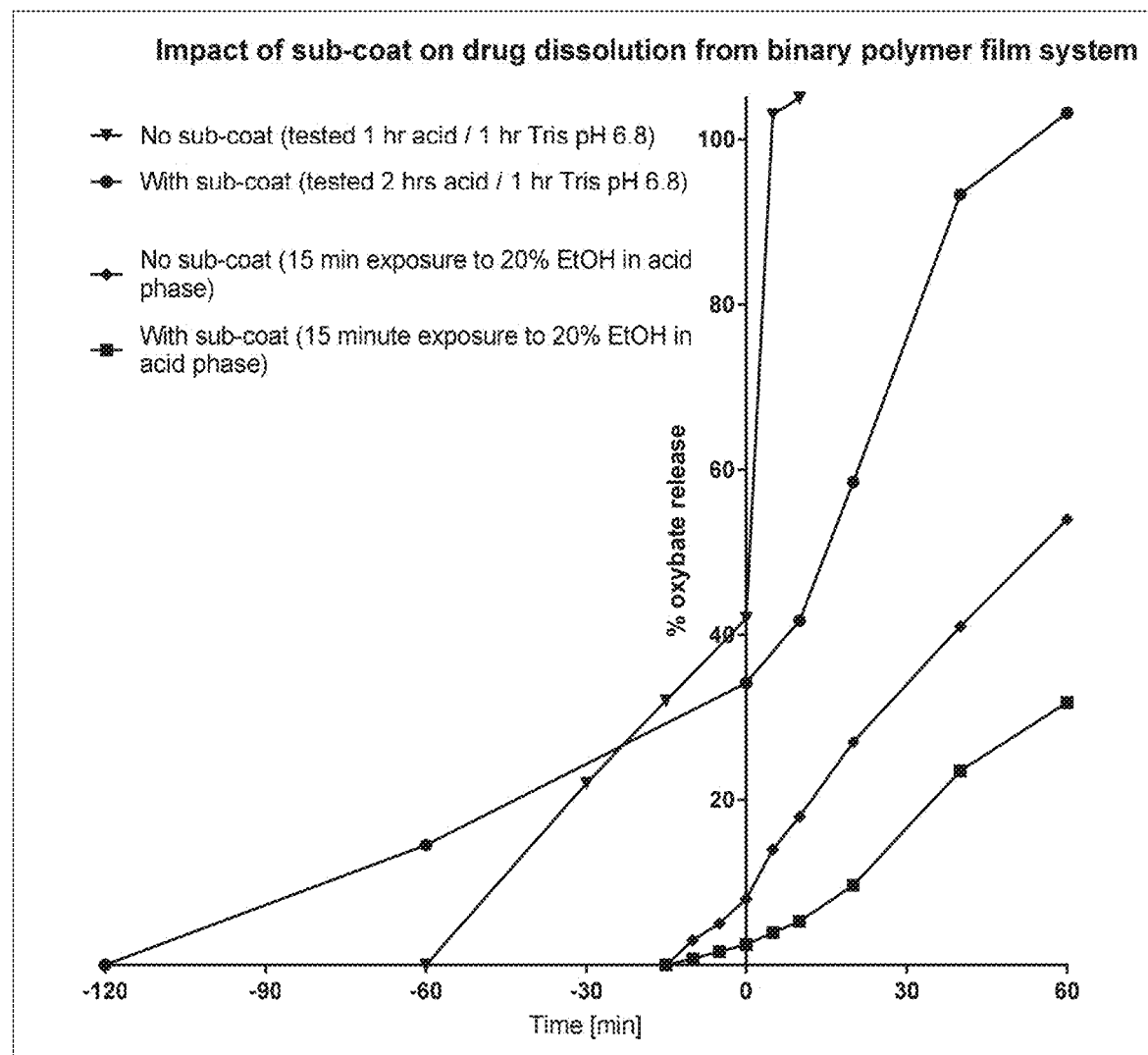
FIG. 8 is a graph showing the impact of the use of a polymer sub-coat on the resultant dissolution profile of binary polymer film coated calcium oxybate pellets exposed for 1-2 hours to 0.1N HCl buffer followed by 1 hour in Tris pH 6.8 buffer both with (circles) and without the sub-coat (inverted triangles) as well as after exposure to 0.1N HCl buffer containing 20% v/v ethanol for 15 minutes followed by 1 hour exposure to Tris pH 6.8 buffer, both with (squares) and without the sub-coat (diamonds).
Figure 9:
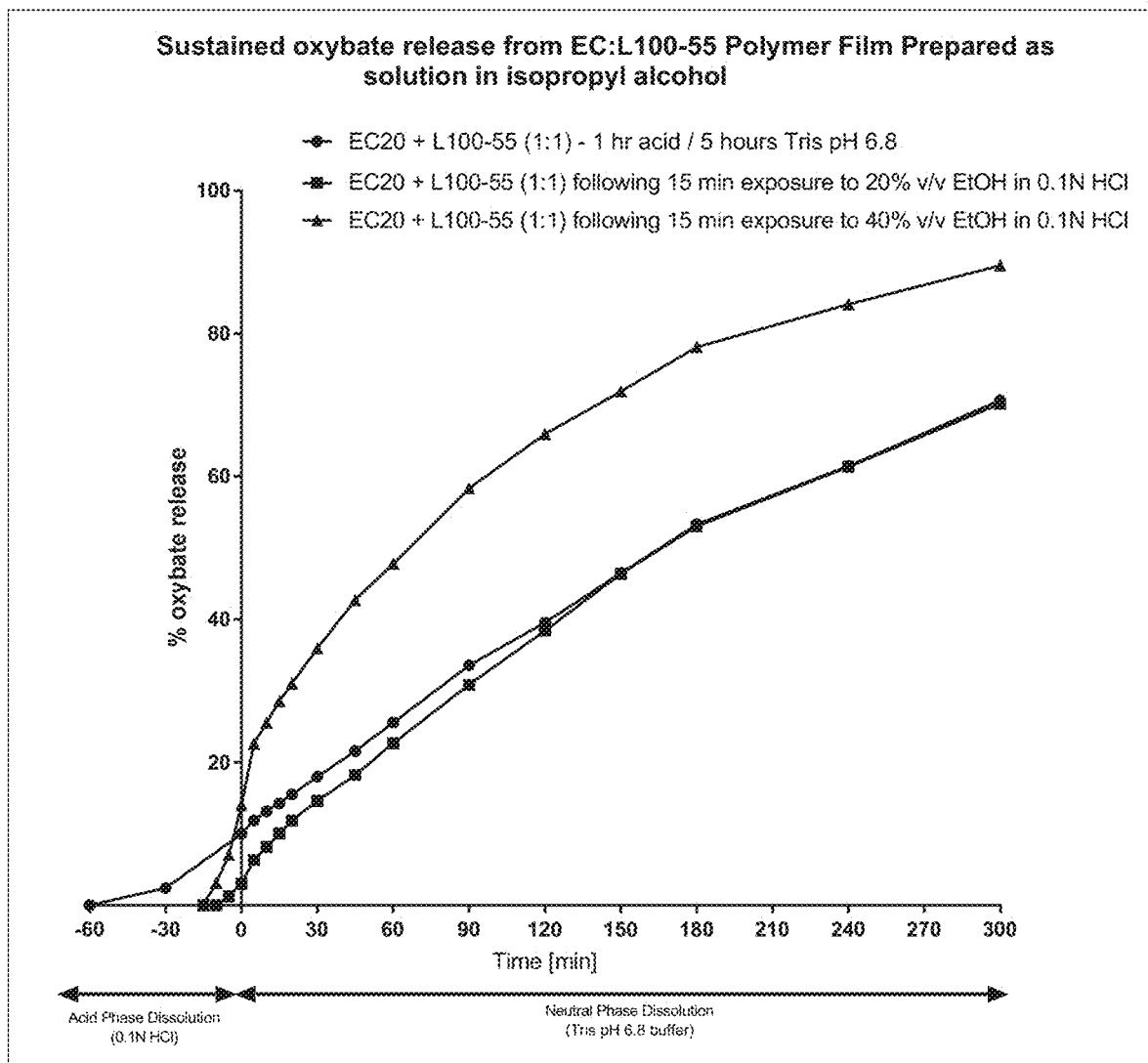
FIG. 9 is a graph showing a sustained release (close to first order) oxybate dissolution profile over a 4 hour period under bi-phasic dissolution test conditions following application of a binary polymer film of ethylcellulose (EC) and methacrylic acid-ethylacrylate co-polymer 1:1 (as Eudragit® L100-55) to calcium oxybate pellets. The binary polymer film was prepared as a solution in organic solvent.

The graph in FIG. 8 shows the two-stage dissolution data as presented for 1-2 hours exposure to 0.1N HCl buffer followed by 1 hour in Tris pH 6.8 buffer both with (circles) and without the sub-coat (inverted triangles). Two stage dissolution data is also presented for 15 min exposure to 0.1N HCl buffer containing 20% v/v ethanol followed by 1 hour exposure to Tris pH 6.8 buffer both with (squares) and without the sub-coat (diamonds). Comparison is made to FIG. 9 which is a graph showing a sustained release (close to first order) oxybate dissolution profile over a 4 hour period under bi-phasic dissolution test conditions following application of a binary polymer film of ethylcellulose (EC) and methacrylic acid-ethylacrylate co-polymer 1:1 (as Eudragit® L100-55) prepared as a solution in organic solvent to calcium oxybate pellet cores.

Example 7

Incorporation of Alternative Polymethacrylate Polymers

A binary polymer film of ethylcellulose (EC) and methacrylic acid-methyl methacrylate co-polymer 1:1 (as Eudragit® L100) prepared as an aqueous dispersion was applied to calcium 3-hydroxybutyrate (Ca-3HB) pellet cores. The Ca-3HB pellet core was manufactured as per the method described for the manufacture of Ca oxybate pellet cores of Example 1. The cores were of the same % w/w composition, with the replacement of Ca oxybate with Ca-3HB. The Ca-3HB pellets were screened to the same size distribution as the Ca oxybate pellets (i.e. 0.8 mm-1.25 mm).

Figure 10:
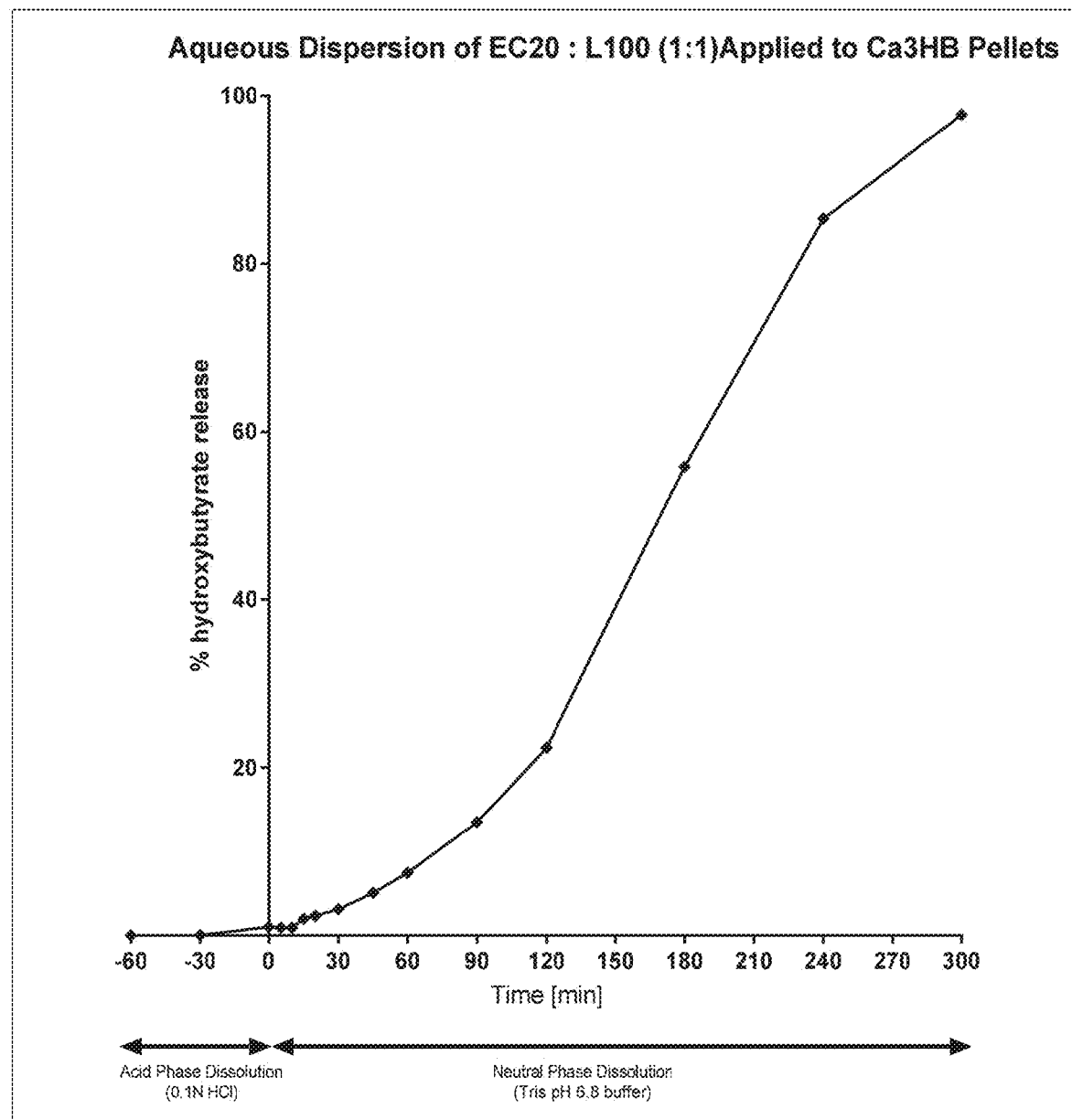
FIG. 10 is a graph showing hydroxybutyrate dissolution profile following application of a binary polymer film of ethylcellulose (EC) and methacrylic acid-methyl methacrylate co-polymer 1:1 (as Eudragit® L100) prepared as an aqueous dispersion and applied to calcium 3-hydroybutyrate (Ca-3HB) pellets. The binary polymer film was applied directly to Ca3HB pellets to a level equivalent to 15% w/w of the pellet core.

The binary polymer film was applied directly to Ca3HB pellet cores to a level equivalent to 15% w/w of the pellet core. As shown in the graph in FIG. 10, the incorporation of the Eudragit® L100 polymer with pH 6 dissolution trigger point results in an enteric release profile as shown with complete suppression of hydroxybutyrate release in acid (60 min).

Figure 11:
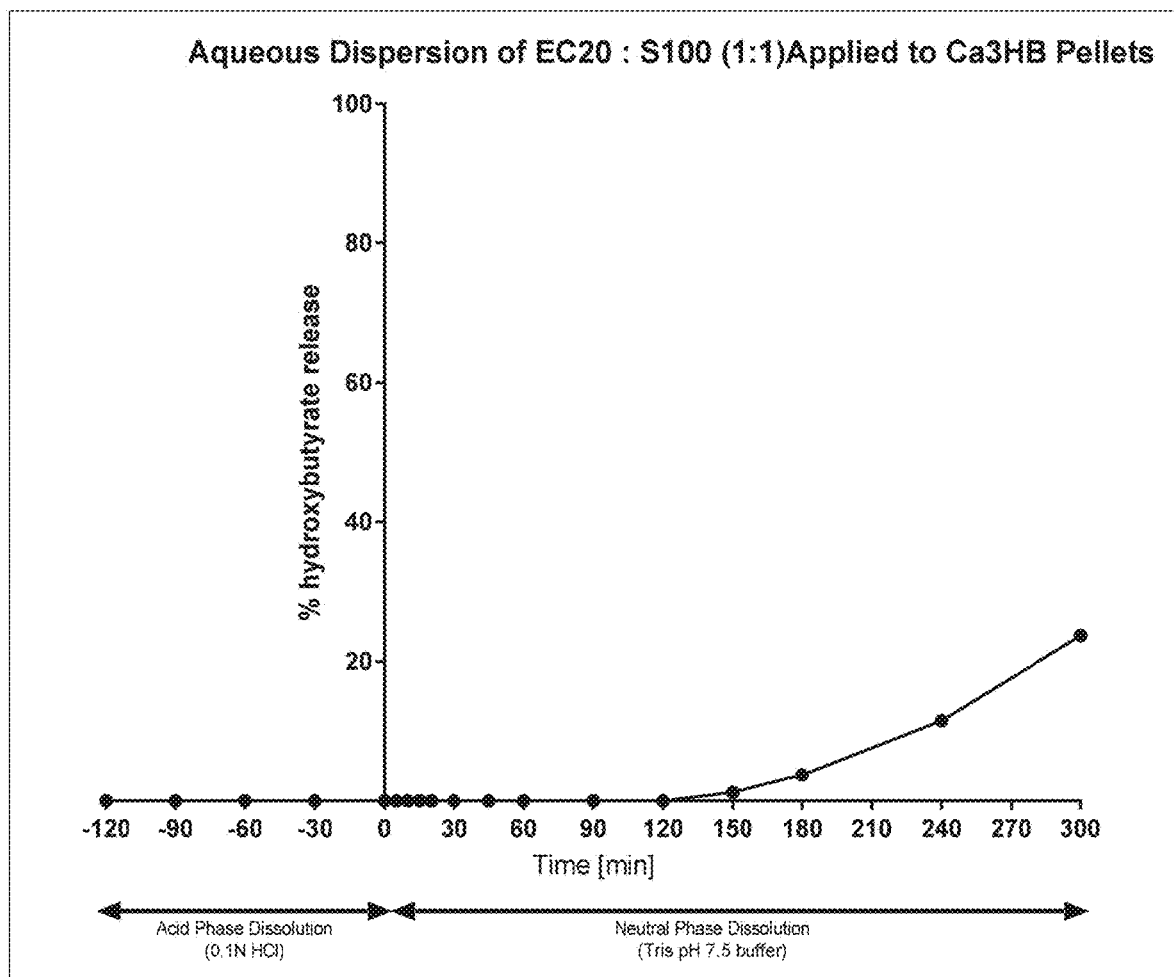
FIG. 11 is a graph showing hydroxybutyrate dissolution profile following application of a binary polymer film of ethylcellulose (EC) and methacrylic acid-methyl methacrylate co-polymer 1:2 (as Eudragit® S100) prepared as an aqueous dispersion and applied to calcium 3-hydroybutyrate (Ca-3HB) pellets. The binary polymer film was applied directly to Ca3HB pellets to a level equivalent to 15% w/w of the pellet core. The incorporation of the Eudragit® S100 polymer with pH 7 dissolution trigger point results in complete suppression of hydroxybutyrate release in acid (120 min), followed by extended suppression of release over 2.5 hours in Tris pH 7.5 buffer, above the pH dissolution trigger of S100 polymer over a 5 hour period. After 5 hours exposure to Tris pH 7.5 buffer only approximately 20% hydroxybutyrate is released from the coated pellet core.

FIG. 11 shows the hydroxybutyrate dissolution profile following application of a binary polymer film of ethylcellulose (EC) and methacrylic acid-methyl methyacrylate co-polymer 1:2 (as Eudragit® S100) prepared as an aqueous dispersion and applied to calcium 3-hydroxybutyrate (Ca-3HB) pellet cores. As above, the binary polymer film was applied directly to Ca3HB pellet cores to a level equivalent to 15% w/w of the pellet core. The incorporation of the Eudragit® S100 polymer with pH 7 dissolution trigger point results in complete suppression of hydroxybutyrate release in acid (120 minutes), followed by extended suppression of release over 2.5 hours in Tris pH 7.5 buffer, above the pH dissolution trigger of S100 buffer over a 5 hour period. After 5 hours exposure to Tris pH 7.5 buffer only approximately 20% hydroxybutyrate is released from the coated pellet core.

Figure 12:
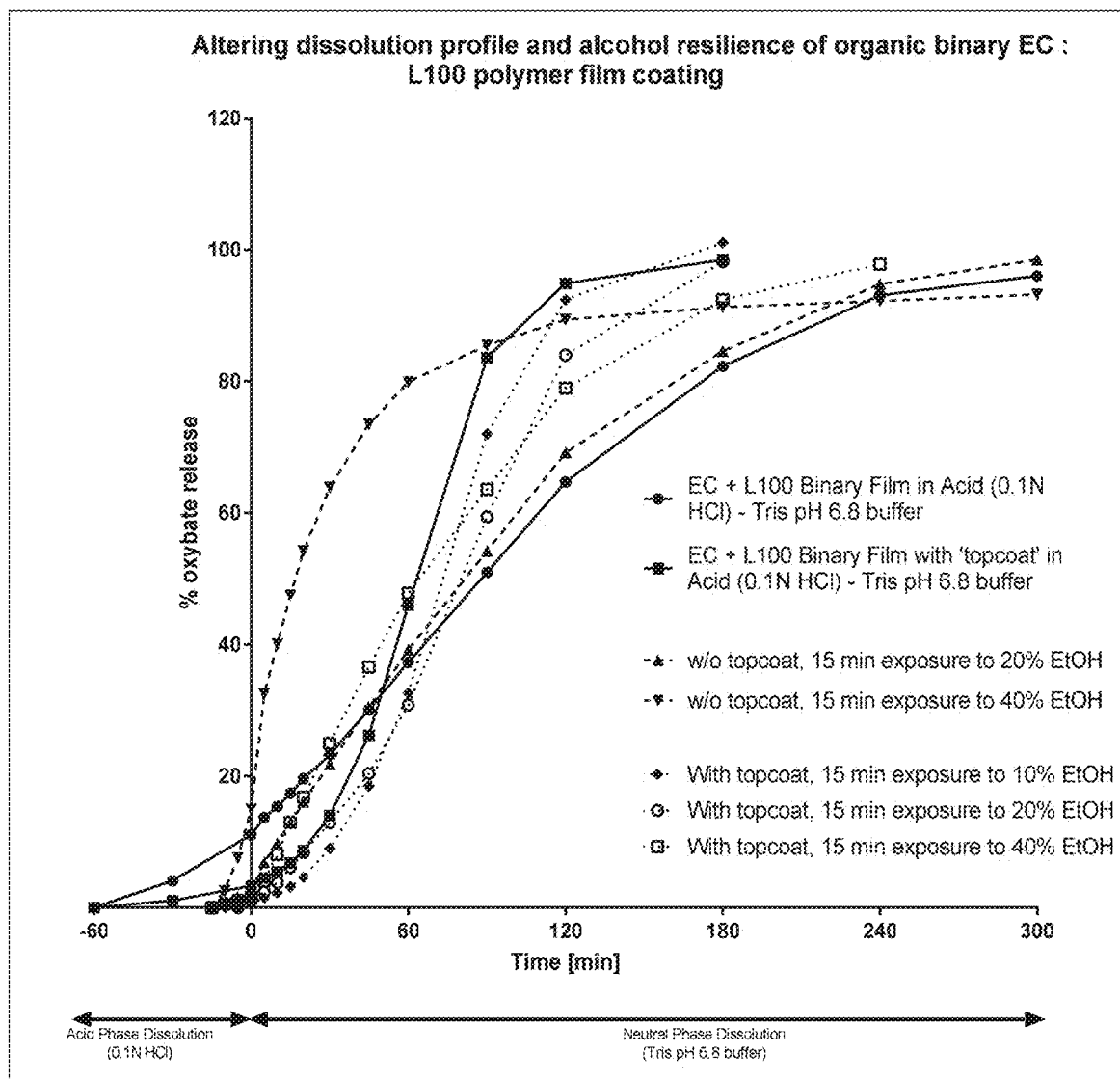
FIG. 12 is a graph showing oxybate dissolution profile from calcium oxybate pellets following application of a binary ethylcellulose (as Ethocel™20) and methacrylic acid-methyl methacrylate co-polymer 1:1 (as Eudragit® L100), at a % w/w dry polymer ratio of 1:2 respectively, (closed circles). The figure also shows oxybate release from the binary film coated pellets following 15 minute exposure to 20% v/v EtOH in 0.1N HCl (dashed line, triangles) and 40% v/v EtOH in 0.1N HCl (dashed line, inverted triangle) followed by release in Tris pH 6.8 buffer. The dissolution profile following the application of a second binary polymer film consisting of ethylcellulose (as the 30% aqueous dispersion) and methacrylic acid-ethylacrylate 1:1 co-polymer (as Eudragit L30D-55) is shown, (closed squares). The oxybate dissolution profile in Tris (pH 6.8) buffer following 15 minute pre-exposure to 0.1N HCl containing 0%, 10%, 20% or 40% v/v ethanol is also shown for the formulation with topcoat applied.

FIG. 12 shows the two stage oxybate dissolution profile following the application of a binary polymer film of ethylcellulose (as Ethocel™ 20) and methacrylic acid-methyl methacrylate 1:1 co-polymer (as Eudragit® L100) to a calcium oxybate pellet core (closed circles). The pellet core was prepared as described in Example 1. The binary polymer film was prepared as a solution in an isopropyl alcohol/water solvent mix at an EC:L100 polymer ratio of 1:2 (based on % w/w dry polymer). The binary polymer film was applied to a level equivalent to 12% w/w of the pellet core. Two-stage dissolution data is also presented for 15 minute pre-exposure to 0.1N HCl buffer containing 20% v/v ethanol and 40% v/v ethanol followed by 5 hour exposure to Tris pH 6.8 buffer (triangles and inverted triangles respectively). The application of the binary film results in a relatively pH-independent extended release of oxybate over 6 hours (closed circles). The film is resilient to dissolution change following 15 min exposure to 20% v/v EtOH in acid, (triangles). Upon 15 minute pre-exposure of the formulation to 40% v/v EtOH in acid, (inverted triangles), the oxybate dissolution rate increases significantly.

Two-stage oxybate dissolution data is also shown following the application of a binary polymer 'topcoat' to the Ethocel™ 20-L100 coated pellet cores, (closed squares). The 'topcoat' consists of an aqueous dispersion of ethylcellulose and methacrylic acid-ethylacrylate 1:1 co-polymer (as Eudragit® L30D-55). The two polymers were used at a ratio of 1:1 (% w/w dry polymer). Guar gum was incorporated at a level of 10% w/w dry polymer content. The 'topcoat' polymer film was applied to a level equivalent to 5% w/w of the coated pellet core. The application of the 'topcoat' polymer film alters the oxybate dissolution profile significantly, with pH-dependent, enteric, in vitro release profile attained-greater suppression of release in acid and greater than 90% oxybate released following 2 hours exposure to Tris pH 6.8 buffer. The oxybate release profile is largely unchanged following 15 min pre-exposure to 10%, 20% and 40% v/v EtOH, (diamonds, open circles and open squares respectively).

Example 8

Application of Ethylcellulose-Methacrylic Acid Ethylacrylate 1:1 Co-Polymer Binary Polymer Film to Paracetamol Pellet Cores Multi-particulate (pellet) drug carrier cores of paracetamol were made by the process of extrusion-spheronisation. The core composition is provided in Table 4. Core components are weighed and then added to the mixing bowl of a Caleva Multi-lab and pre-blended. Water was added to the mixed dry components until a wet mass was formed. The wet mass was mixed for an additional 10 minutes then extruded (die plate diameter of 1.0 mm). The extrudate was then spheronised and dried to form the paracetamol pellet core.

TABLE 4

Composition of the paracetamol pellet core

| Component | Quantity (% w/w) |
| --- | --- |
| Paracetamol | 10.0 |
| Lactose | 40.0 |
| Microcrystalline cellulose | 50.0 |
| Water* | q.s |

A binary polymer film coat consisting ethylcellulose (as the 30% aqueous dispersion, Aquacoat® ECD) and methacrylic acid-ethylacrylate 1:1 co-polymer (as Eudragit® L30D-55) was applied to paracetamol pellet cores at varying film thickness. The polymer film was prepared as an aqueous dispersion with polymer ratio of 1:1 (based on % w/w dry polymer).

Figure 13:
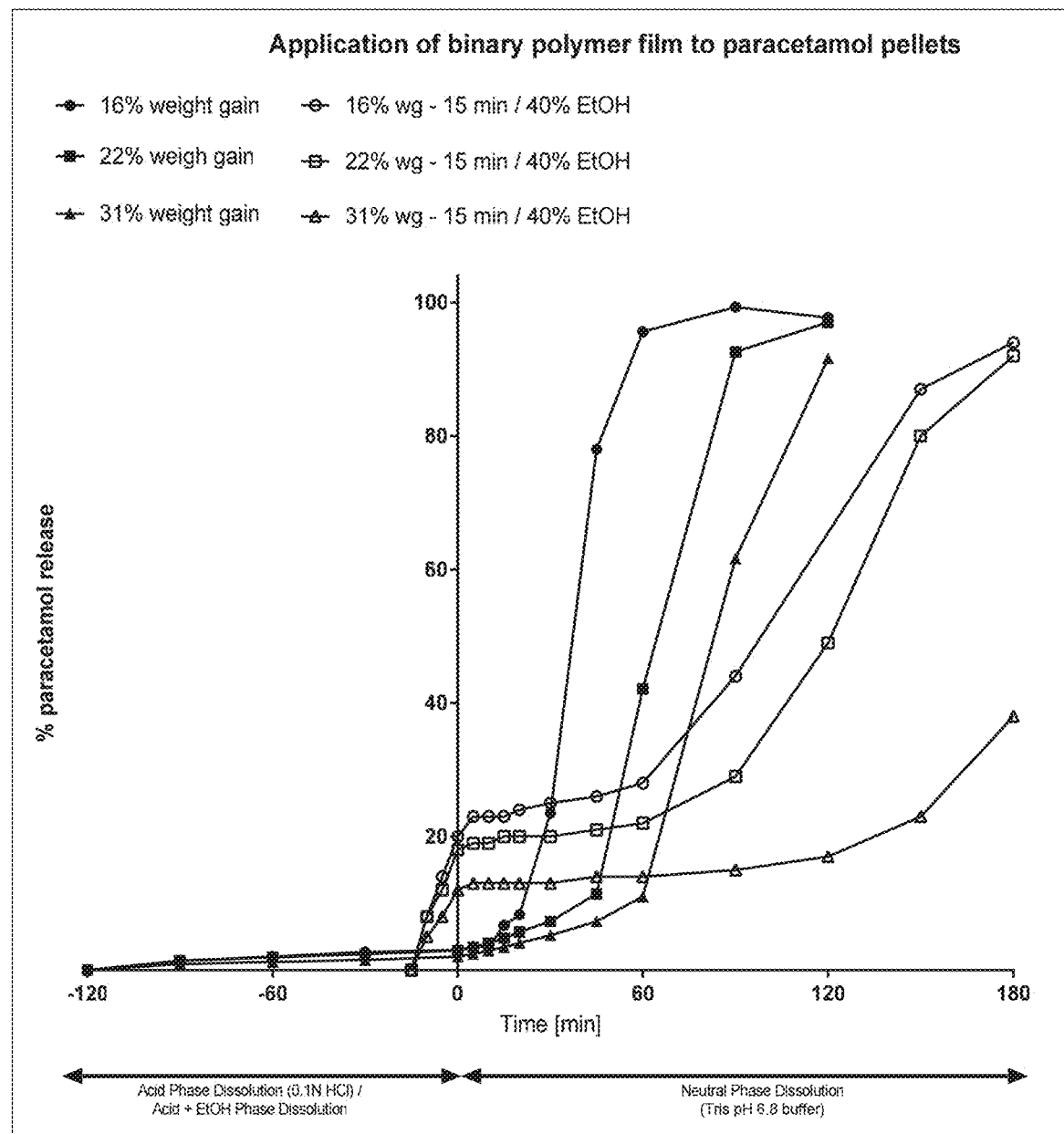
FIG. 13 is a graph showing paracetamol release following application of a binary polymer film coat consisting ethylcellulose (as 30% aqueous dispersion, Aquacoat® ECD) and methacrylic acid-ethylacrylate 1:1 co-polymer (as Eudragit® L30D-55). The effect of increasing polymer film thickness on resultant dissolution rate is demonstrated. The figure also shows the impact of 15 minute pre-exposure to 40% v/v EtOH in 0.1N HCl on subsequent release in Tris pH 6.8 buffer.

FIG. 13 presents data generated for two-stage in-vitro dissolution testing of the binary film coated paracetamol pellets (0.1N HCl-Tris pH 6.8 buffer). At all polymer film thicknesses investigated, paracetamol release is significantly suppressed in acid. The lag in paracetamol release in the Tris pH 6.8 buffer is extended with increasing polymer film thickness. In-vitro dissolution data is also presented following 15 minute pre-exposure of the coated paracetamol pellets to 0.1N HCl containing 40% v/v EtOH. A hydrogel is observed around the paracetamol pellets following exposure to the acid-EtOH mix. Paracetamol dissolution rate following subsequent transfer of the EtOH exposed coated pellets to Tris pH 6.8 buffer is suppressed for between approx. 60-120 minutes, depending on the polymer film thickness.

Example 9

Sustained Release Oxybate Prototypes: In Vitro Dissolution Correlates with In Vivo Pharmacokinetics Prototypes were prepared for pharmacokinetic evaluation in humans. Calcium oxybate (monohydrate) multi-particulate (pellet) cores were prepared by extrusion-spheronisation at a batch scale of approximately 1.8 Kg (batch sizes can vary, with typical batch sizes ranging from 0.5 Kg to 3.0 Kg). The composition of the pellet core is provided in Table 5.

TABLE 5

Composition of the calcium oxybate pellet core prepared for human PK studies

| Component | Quantity per Batch (kg) |
| --- | --- |
| Calcium oxybate (monohydrate) | 1.530 |
| Microcrystalline cellulose | 0.126 |
| Hydroxypropyl Cellulose | 0.090 |
| Hydroxypropyl Cellulose, low-substituted | 0.054 |
| Purified water* | 0.34 |

The drug carrier core is manufactured by high shear blending the drug substance with microcrystalline cellulose, hydroxypropyl cellulose and low-substituted hydroxypropyl cellulose. An aqueous solution of hydroxypropyl cellulose (10% w/w) is added to the dry powder under mixing to produce a plastic wet mass for extrusion. The wet mass is extruded (NICA™ E140, GEA Germany) and the extruded mass spheronized (NICA™ 5450, GEA Germany). The wet pellets are dried using a fluid bed drier and then screened to the desired size range.

Two different sustained release dosage forms were produced for human PK evaluation:

1. Sustained release using ethylcellulose-based polymer film coating ('SR1')
2. Sustained release using ethylcellulose+methacrylic acid-ethylacrylate binary polymer film system ('SR2')

The 'SR1' prototype is produced by directly applying a polymer film comprising ethylcellulose (Ethocel Standard 20 Premium), and polyvinylpyrrolidone (Kollidon K30) to the calcium oxybate (monohydrate) pellet core. The polymer is prepared as a solution in isopropyl alcohol and water and applied to the core via a bottom-spray fluid bed process. The composition of 'SR1' is presented in Table 6.

TABLE 6

Composition of 'SR1' Prototype for Human PK studies

| Component | Function | Composition (% w/w) |
| --- | --- | --- |
| Calcium oxybate monohydrate | Active Ingredient | 79.45 |
| Microcrystalline cellulose | Binder & process aid | 6.54 |
| Hydroxypropyl cellulose | Binder and coating polymer | 4.67 |
| Hydroxypropyl cellulose, low substituted (L-HPC) | Binder | 2.80 |
| Ethylcellulose | Functional (sustained release) polymer film | 4.85 |
| Polyvinylpyrrolidone | Polymer film pore former | 1.21 |
| TEC | Polymer film plasticizer | 0.48 |

The 'SR2' prototype is produced by directly applying a binary polymer film comprising ethylcellulose (as 30% aqueous dispersion) and methacrylic acid-ethyl acrylate (1:1) co-polymer (as 30% aqueous dispersion) to the calcium oxybate (monohydrate) pellet core. The polymer is prepared as an aqueous dispersion and applied to the core via a top-spray fluid bed process. The composition of 'SR2' is presented in Table 7.

TABLE 7

Composition of 'SR2' Prototype for Human PK studies

| Component | Function | Composition (% w/w) |
| --- | --- | --- |
| Calcium oxybate monohydrate | Active Ingredient | 76.58 |
| Microcrystalline cellulose | Binder & process aid | 6.31 |
| Hydroxypropyl cellulose | Binder and coating polymer | 4.50 |
| Hydroxypropyl cellulose, low substituted (LH-31, Shin Etsu) | Binder | 2.70 |
| Ethylcellulose, 30% aqueous dispersion (also comprising sodium lauryl sulphate and cetyl alcohol) | Functional polymer film (pH independent dissolution) | 4.50 |
| Methacrylic acid—ethyl acrylate copolymer (1:1), Type A, 30% aqueous dispersion (also comprising sodium lauryl sulphate and polysorbate 80) | Functional polymer film (pH dependent dissolution, triggered at pH ≥ 5.5) | 4.50 |
| TEC | Polymer film plasticizer | 0.90 |

Figure 14:
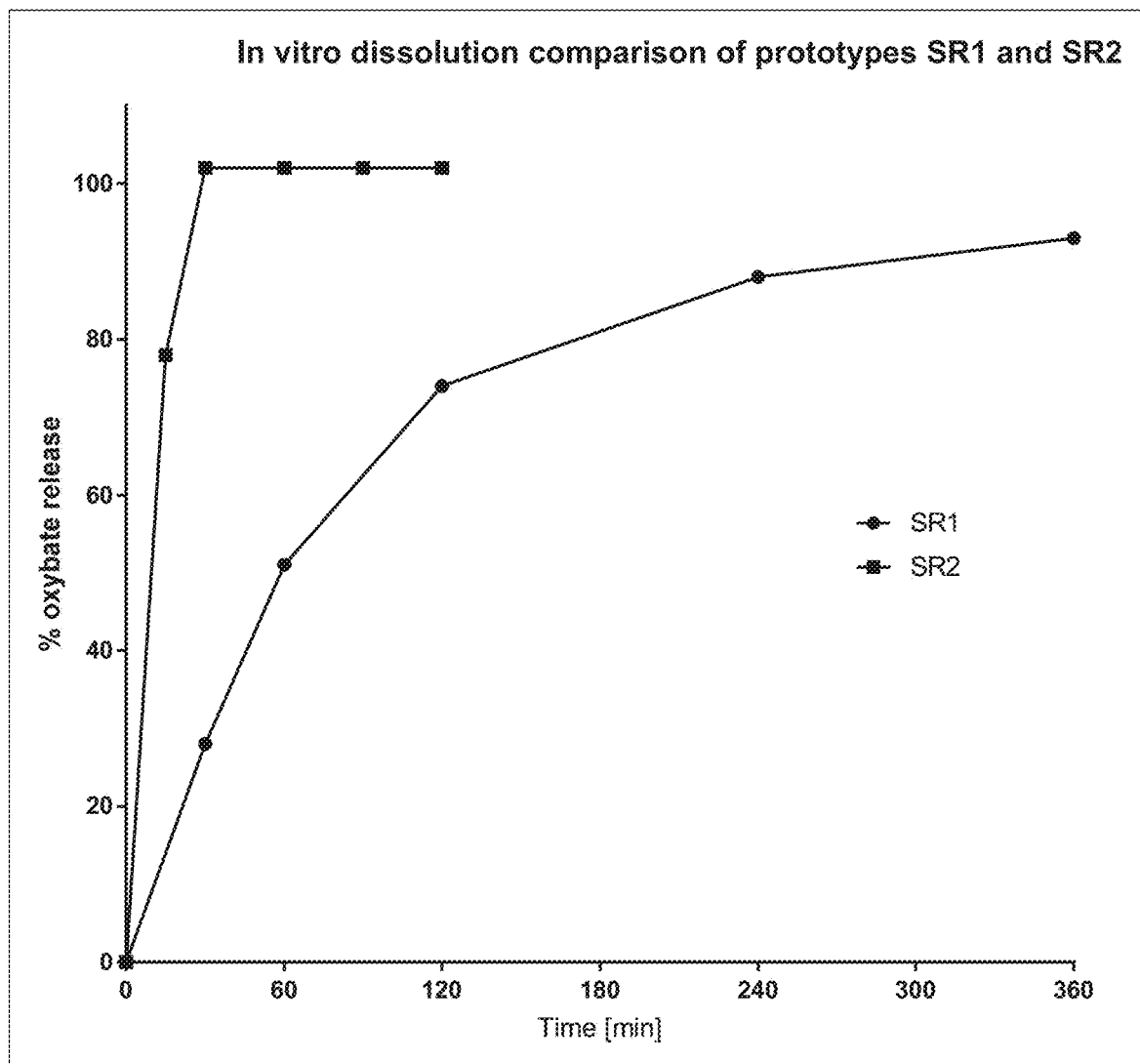
FIG. 14 is a graph comparing the dissolution of two sustained release (SR) oxybate prototypes prepared for human pharmacokinetic studies. The 'SR1' consists of a calcium oxybate (monohydrate) pellet core onto which an ethylcellulose-based functional film coat is applied. The 'SR2' consists of the same pellet core onto which a binary polymer film is applied consisting of a 1:1 mix, based on dry polymer weight, of ethylcellulose and methacrylic acid ethylacrylate (1:1) co-polymer.
Figure 15:
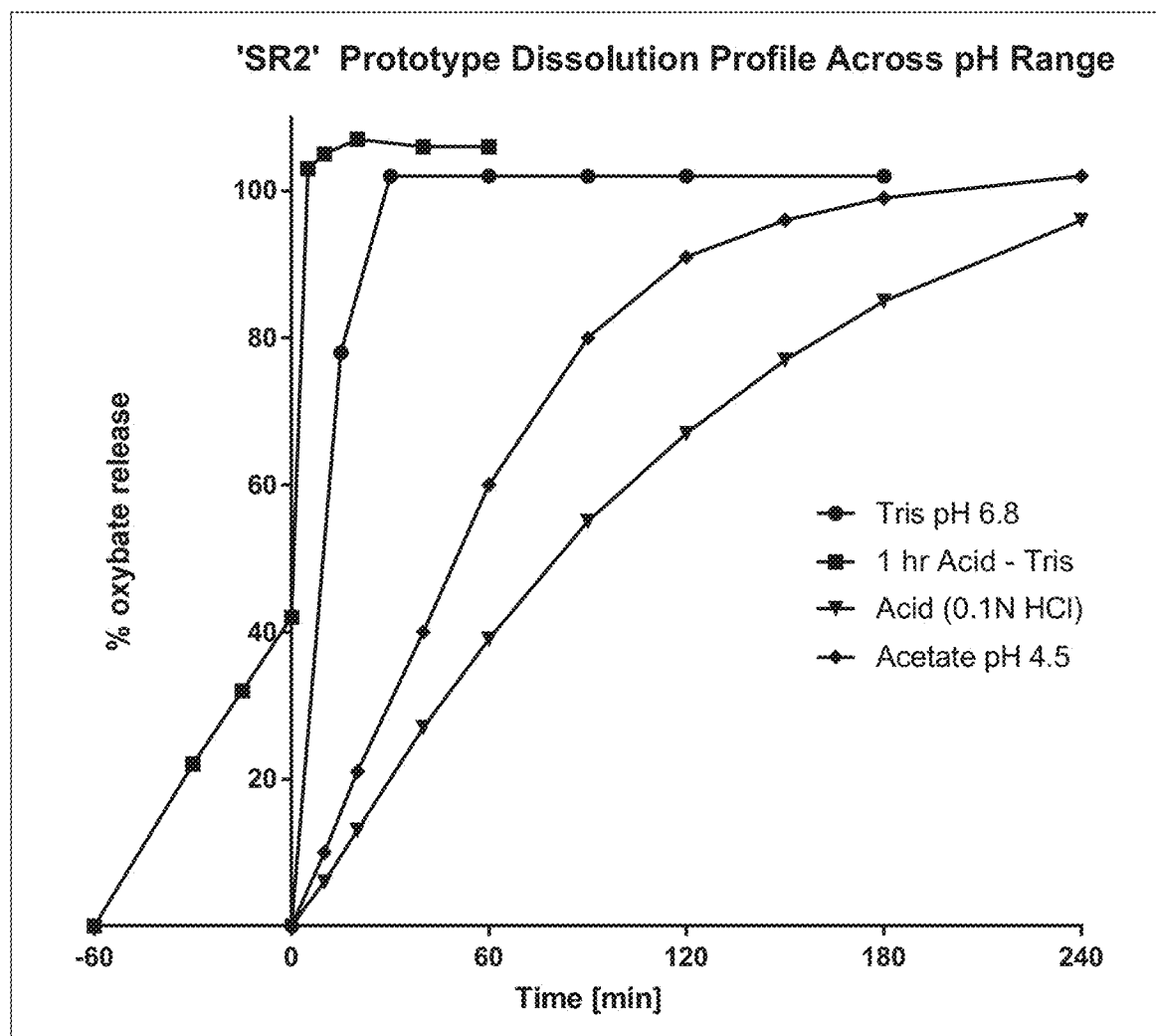
FIG. 15 is a graph comparing the dissolution of a prototype, 'SR2', under different pH conditions. The prototype consists of consists of a calcium oxybate (monohydrate) pellet core onto which a binary polymer film is applied consisting of a 1:1 mix, based on dry polymer weight, of ethylcellulose and methacrylic acid ethylacrylate (1:1) co-polymer.

The in vitro dissolution profiles for the 'SR1' and 'SR2' prototypes are presented in FIG. 14. The dissolution was performed in 900 mL 0.04M Tris buffer pH 6.8 at 37° C. using USP type II (rotating paddle) apparatus with paddle speed of 100 rpm. As the 'SR2' functional polymer film is comprised of a 1:1 mixture of pH-independent ethylcellulose and pH-dependent methacrylic acid-ethyl acrylate co-polymer, its dissolution was tested under alternative pH conditions to elicit pH response upon mixing both polymer types. The dissolution profiles are presented in FIG. 15 and demonstrate pH-dependent release properties of the composition.

Figure 16:
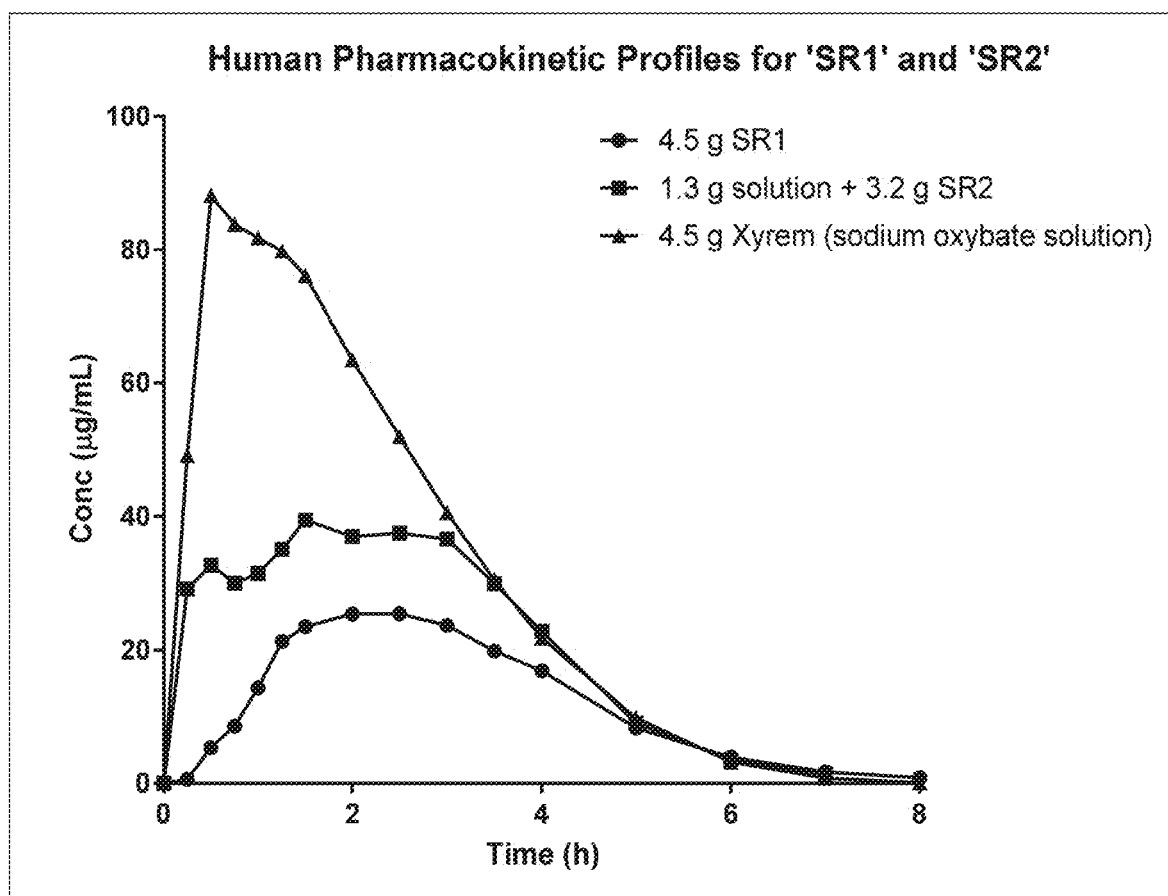
FIG. 16 is a graph comparing the human pharmacokinetic profiles of two SR oxybate prototypes administered to healthy volunteers two hours after the start of a high-fat, high-calorie breakfast. A total dose equivalent to 4.5 g sodium oxybate was administered. The 'SR1' consists of a calcium oxybate (monohydrate) pellet core onto which an ethylcellulose-based functional film coat is applied. The 'SR1' prototype was administered individually. The 'SR2' consists of the same pellet core onto which a binary polymer film is applied consisting of a 1:1 mix, based on dry polymer weight, of ethylcellulose and methacrylic acid ethylacrylate (1:1) co-polymer. The 'SR2' prototype was administered in combination with an aqueous oxybate solution at a dose ratio of 1:2.5 solution to 'SR2' respectively.

The two SR compositions were administered to healthy human volunteers two hours after the start of a high-fat, high-calorie breakfast (dose equivalent to 4.5 g sodium oxybate). The PK data is presented in FIG. 16. The 'SR2' prototype was administered in combination with an aqueous (IR) oxybate solution at a dose ratio of 1:2.5 solution:'SR2' respectively. The 'SR1' prototype was administered individually at 4.5 g equivalent sodium oxybate. The data demonstrates that the faster releasing prototype in vitro, 'SR2', results in higher relative oxybate bioavailability. As shown in the graphs, the 'SR1' prototype demonstrates significantly lower exposure compared to the 'SR2' prototype.

Figure 17:
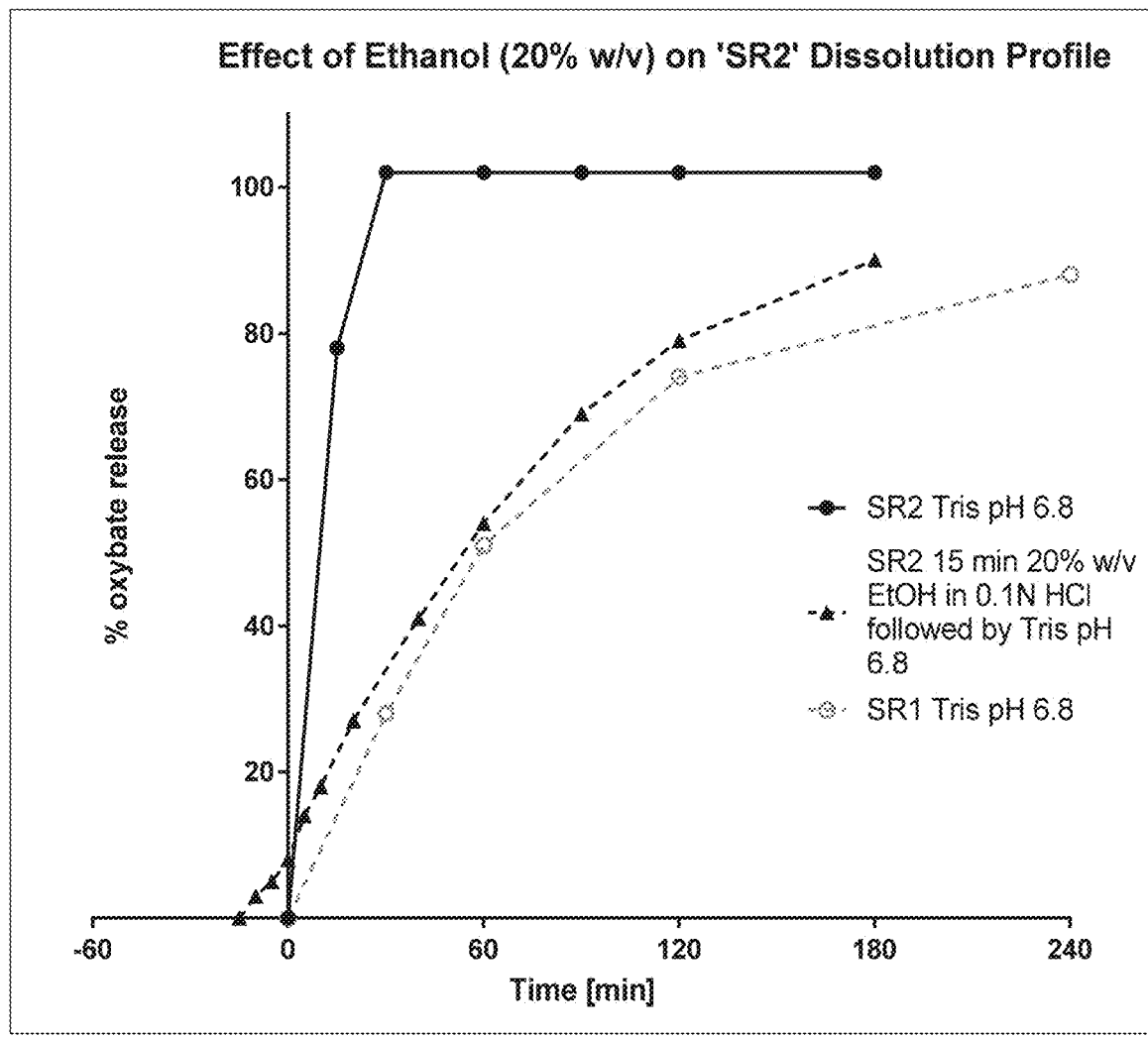
FIG. 17 is a graph comparing the dissolution in Tris pH 6.8 buffer of a binary film prototype of Example 9, 'SR2', in the absence (circles) or presence (triangles) of a 15 minute pre-exposure to 0.1N HCl containing 20% v/v ethanol. Comparison is made to the dissolution of the 'SR1' prototype of Example 9 in Tris pH 6.8 buffer.

The effect of 15 minute exposure to 20% v/v ethanol in acid (0.1N HCl) on the resultant dissolution profile of the binary polymer film 'SR2' prototype in Tris pH 6.8 buffer is presented in FIG. 17. It can be seen that exposure to ethanol results in a subsequent slowing of oxybate dissolution from the coated pellet. Although not wishing to be bound by any one theory, a comparison to the dissolution of the 'SR1' prototype suggests that the slowdown in oxybate dissolution might result in a significant decrease in oxybate bioavailability.

Example 10

Pharmacokinetics of Delayed Release Oxybate Examples

Delayed (enteric) release oxybate prototypes were prepared for pharmacokinetic evaluation in humans. Calcium oxybate (monohydrate) pellet cores were prepared as described in Example 9. Two delayed release dosage forms were produced for human PK evaluation:

1. Delayed release using methacrylic acid-ethyl acrylate based polymer film coating ('DR1')
2. Delayed release using ethylcellulose+methacrylic acid-ethylacrylate binary polymer film system ('DR2')

The 'DR1' prototype is produced by applying a methacrylic acid-ethyl acrylate (1:1) co-polymer based film, (as AcrylEze® II, (Colorcon, USA)) to a hydroxypropyl cellulose sub-coated calcium oxybate (monohydrate) pellet core. The polymer is prepared as an aqueous suspension and applied via a bottom-spray fluid bed process. The composition of 'DR1' is presented in Table 8.

TABLE 8

Composition of 'DR1' Prototype for Human PK studies

| Component | | Function | Composition (% w/w) |
|---|---|---|---|
| Calcium oxybate monohydrate | | Active Ingredient | 60.53 |
| Microcrystalline cellulose | | Binder & process aid | 4.99 |
| Hydroxypropyl cellulose | | Binder and coating polymer | 9.26 |
| Hydroxypropyl cellulose, low substituted (L-HPC) | | Binder | 2.15 |
| AcrylEze ® II | Methacrylic acid and ethyl acrylate copolymer Talc Titanium dioxide Poloxamer 407 Calcium silicate Sodium bicarbonate Sodium lauryl sulphate | Functional (enteric) polymer film | 23.07 |

The 'DR2' prototype (for clarification, this is different from "DR02" listed in the above Examples) is produced by directly applying a binary polymer film comprising ethylcellulose and methacrylic acid-ethyl acrylate (1:1) co-polymer to the calcium oxybate (monohydrate) pellet core. The ethylcellulose and methacrylic acid-ethyl acrylate (1:1) co-polymer are prepared at an ethylcellulose:copolymer ratio of 1:2 based on % w/w of dry polymer content. The ethylcellulose is provided as a 30% aqueous dispersion as defined in Table 9 below. The methacrylic acid-ethyl acrylate (1:1) co-polymer copolymer is also provided as an aqueous dispersion as defined in Table 9 below. The first polymer film coat is applied until a 15% weight gain is achieved (as % w/w of the uncoated pellet core). A 'top-coat' consisting of ethylcellulose, methacrylic acid-ethyl acrylate (1:1) co-polymer at an ethylcellulose:copolymer ratio of 1:1 based on % w/w of dry polymer and guar gum is then applied (guar gum is used at a concentration of 10% w/w of the ethylcellulose polymer content). The polymers are prepared as an aqueous dispersion and applied to the core via a top-spray fluid bed process. The 'top-coat' is applied until a 5% weight gain is achieved (as % w/w of the pellet core having the first polymer film coat). The composition of 'DR2' is presented in Table 9.

TABLE 9

Composition of 'DR2' Prototype for Human PK studies

| Component | Function | Composition (% w/w) |
|---|---|---|
| Calcium oxybate monohydrate | Active Ingredient | 68.99 |
| Microcrystalline cellulose | Binder & process aid | 5.68 |
| Hydroxypropyl cellulose | Binder and coating polymer | 4.06 |
| Hydroxypropyl cellulose, low substituted (LH-31, Shin Etsu) | Binder | 2.44 |
| Ethylcellulose, 30% aqueous dispersion (also comprising sodium lauryl sulphate and cetyl alcohol) | Functional polymer film (pH independent dissolution) | 6.75 |
| Methacrylic acid—ethyl acrylate copolymer (1:1), Type A, 30% aqueous dispersion (also comprising sodium lauryl sulphate and polysorbate 80) | Functional polymer film (pH dependent dissolution, triggered at pH ≥ 5.5) | 10.15 |
| Guar gum | | 0.24  0.24 |
| TEC | | 1.69  1.69 |

Figure 18:
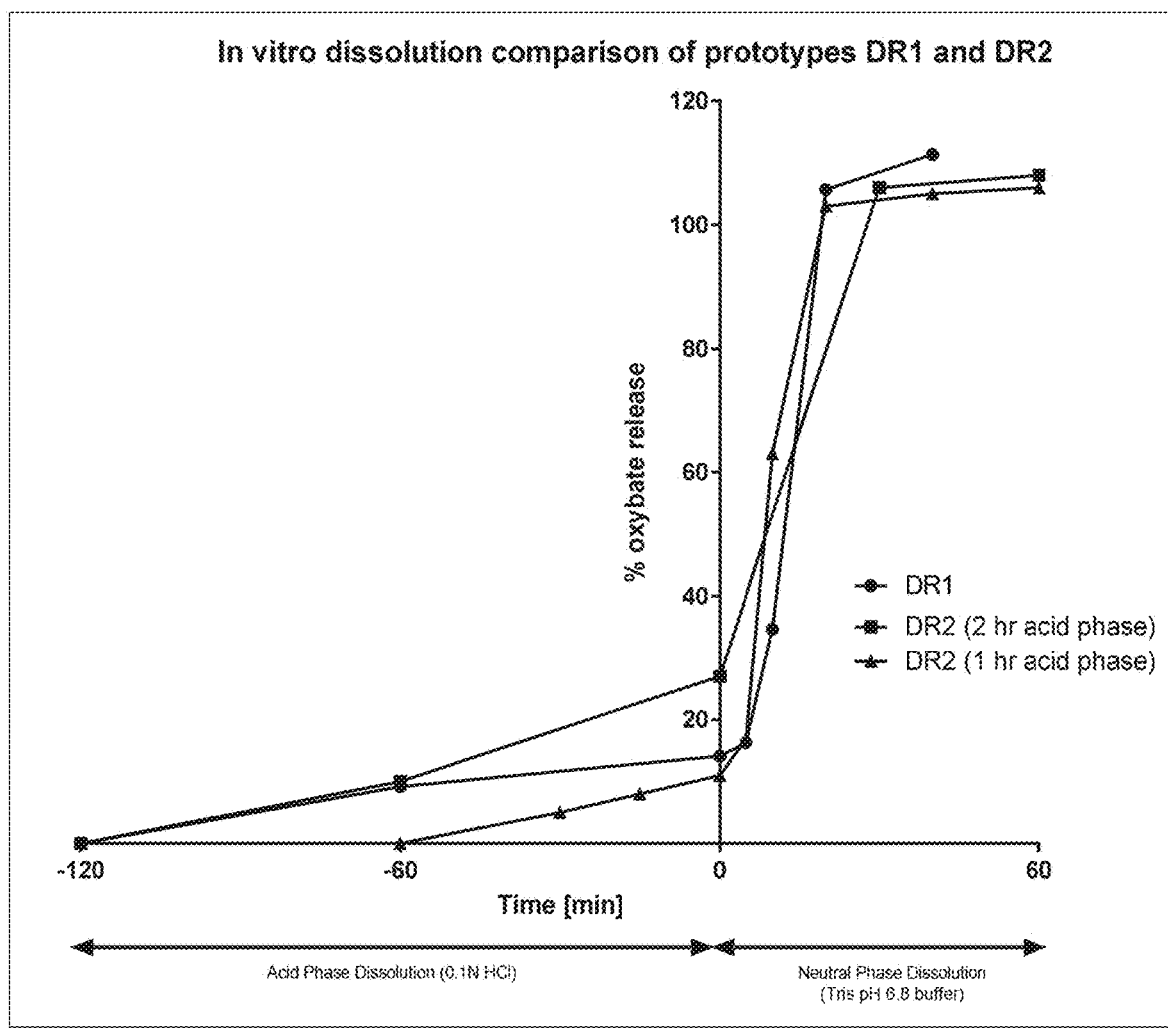
FIG. 18 is a graph comparing the dissolution of two delayed release (DR) oxybate prototypes prepared for human pharmacokinetic studies. The 'DR1' consists of a calcium oxybate (monohydrate) pellet core onto which a methacrylic acid-ethyl acrylate based functional film coat is applied. The 'SR2' consists of the same pellet core onto which a binary polymer film is applied consisting of a mix of ethylcellulose and methacrylic acid ethylacrylate (1:1) co-polymer. A guar gum containing 'top-coat' is also applied to 'DR2'.
Figure 19:
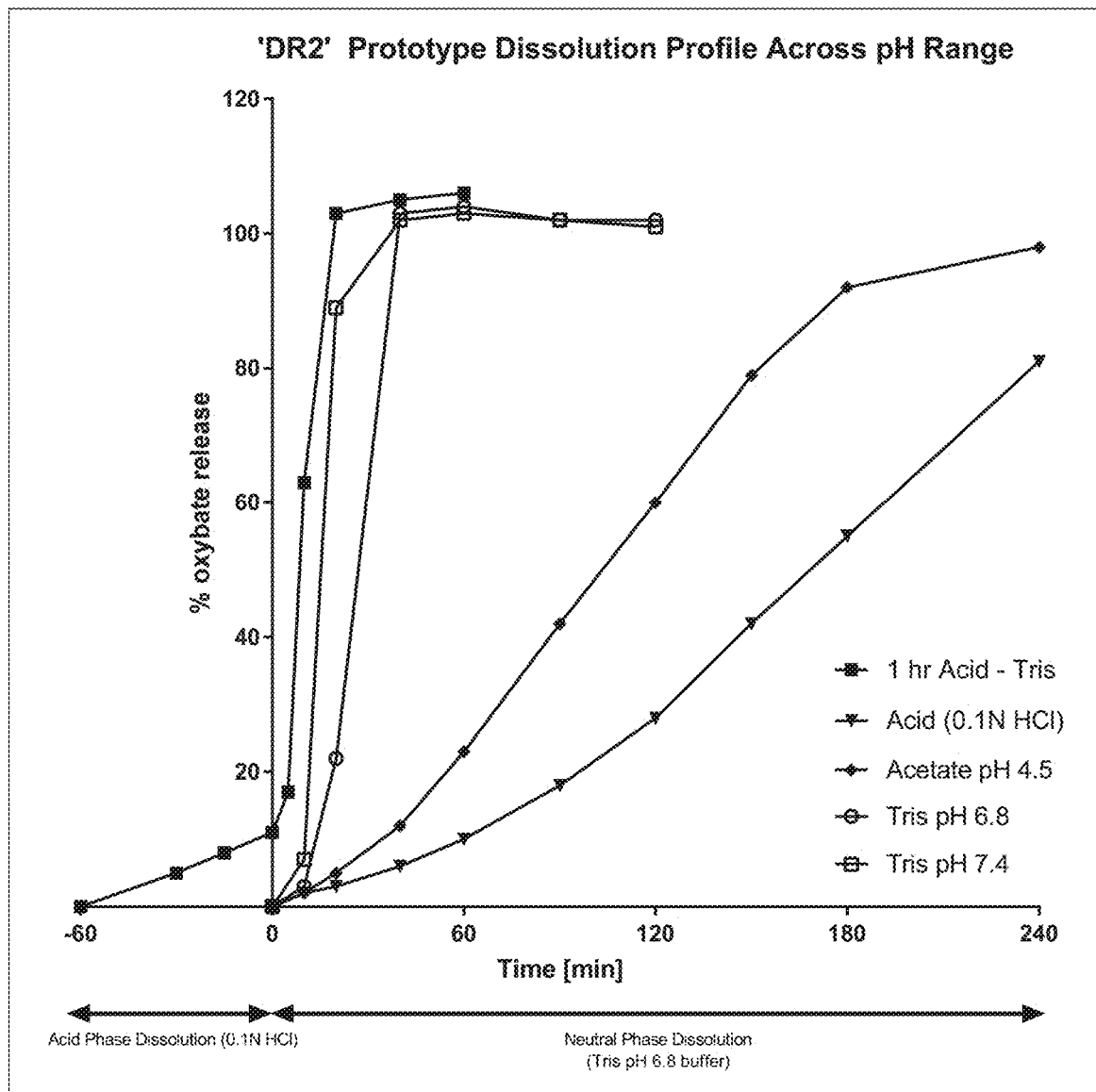
FIG. 19 is a graph comparing the dissolution of a prototype, 'DR2', under different pH conditions. The prototype consists of a calcium oxybate (monohydrate) pellet core onto which a binary polymer film is applied consisting of a mix of ethylcellulose and methacrylic acid ethylacrylate (1:1) co-polymer. A guar gum containing 'top-coat' is also applied.

The in vitro dissolution of prototypes 'DR1' and 'DR2' are compared in FIG. 18. The dissolution was performed over 2 hours in 750 mL 0.1N HCl at 37° C. followed by 2 hours in 1000 mL 0.04M Tris buffer pH 6.8 at 37° C. using USP type II (rotating paddle) apparatus with paddle speed of 100 rpm for both buffer phases. The data demonstrates that a binary polymer film prototype ('DR2') having similar total polymer content on a % w/w basis as a prototype having only an enteric film (DR') can effectively suppress oxybate release in acid. The 'DR2' prototype dissolution was also tested under different pH conditions. The dissolution profiles are presented in FIG. 19. Comparison to the 'SR2' binary polymer prototype of Example 9 shows the increase in pH-dependent dissolution upon increasing methacrylic acid-ethylacrylate content in the functional film coat.

The two 'DR' compositions were administered, in combination with an oxybate solution (IR), to healthy human volunteers two hours after the start of a high-fat, high-calorie breakfast (dose equivalent to 4.5 g sodium oxybate). In a separate pharmacokinetic (PK) study, the 'DR2' composition was administered in combination with an oxybate solution (IR), to healthy volunteers two hours after the start of a high-fat, high calorie breakfast at total doses equivalent to 4.5 g, 7 g and 9 g sodium oxybate (dose escalation study). The three treatments administered in the dose escalation PK study are detailed in Table 10.

TABLE 10

Treatments for 'DR2' Dose Escalation Study

| Treatment | Description |
|---|---|
| 4.5 g dose equivalent to sodium oxybate | 3.0 mL of oxybate solution (containing equivalent to 1.5 g of sodium oxybate) + 4.56 g of 'DR2' pellets (containing equivalent to 3 g of sodium oxybate) |
| 7 g dose equivalent to sodium oxybate | 4.67 mL of oxybate solution (containing equivalent to 2.33 g of sodium oxybate) + 7.09 g of 'DR2' pellets (containing equivalent to 4.67 g of sodium oxybate) |

TABLE 10-continued

Treatments for 'DR2' Dose Escalation Study

| Treatment | Description |
|---|---|
| 9 g dose equivalent to sodium oxybate | 6.0 mL of oxybate solution (containing equivalent to 3 g of sodium oxybate) + 9.12 g of 'DR2' pellets (containing equivalent to 6 g of sodium oxybate) |

Figure 20A:
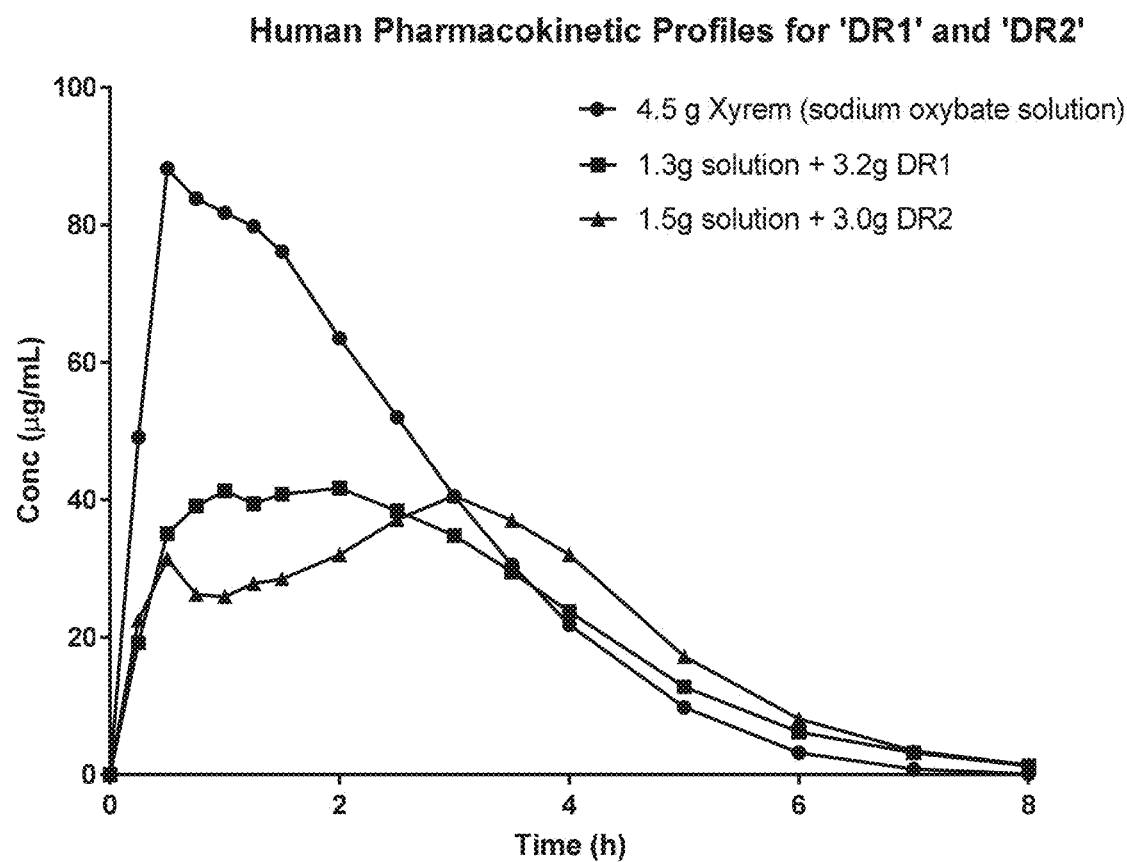
FIG. 20A is a graph comparing the human pharmacokinetic profiles of two DR oxybate prototypes administered to healthy volunteers two hours after the start of a high-fat, high-calorie breakfast. The 'DR1' consists of a calcium oxybate (monohydrate) pellet core onto which a methacrylic acid-ethylacrylate functional film coat is applied. The 'DR2' consists of the same pellet core onto which a binary polymer film is applied consisting of a mix of ethylcellulose and methacrylic acid ethylacrylate (1:1) co-polymer. A guar gum containing 'top-coat' is also applied to 'DR2'.
Figure 20B:
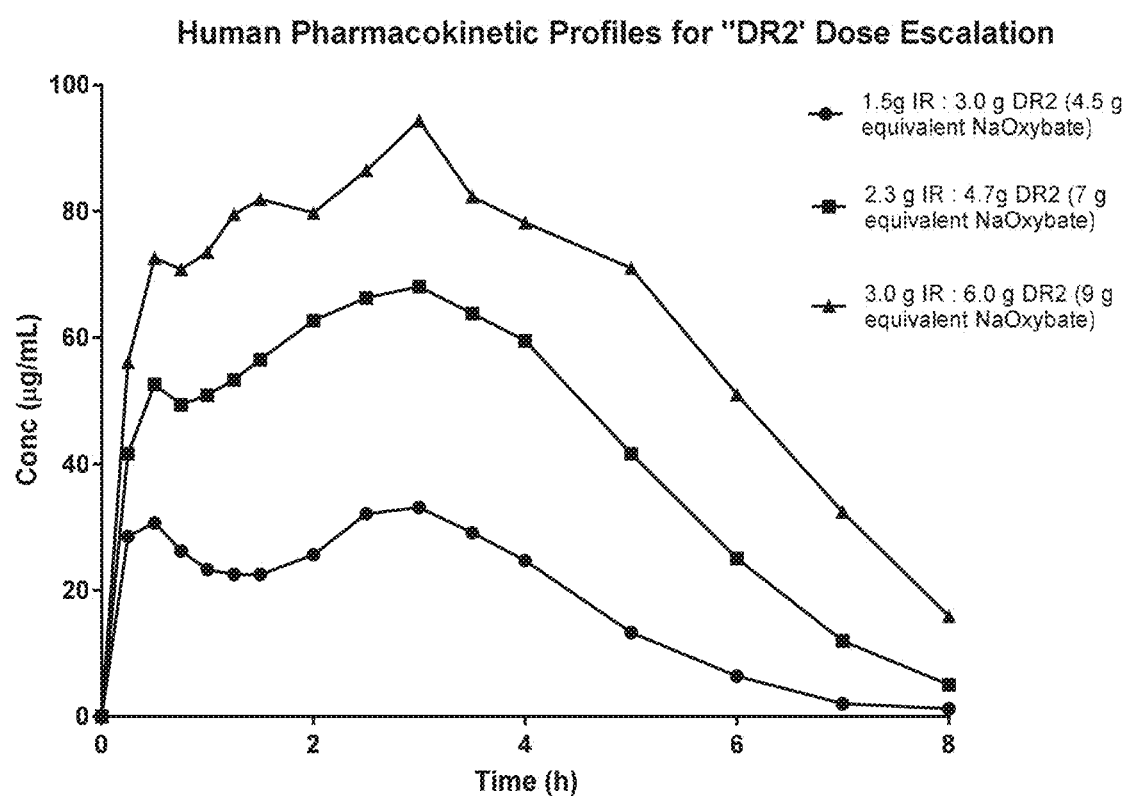
FIG. 20B is a graph of the human pharmacokinetic profiles of the modified release 'DR2' particle in combination with an oxybate solution (a mixture of sodium and potassium oxybate salts) administered at 4.5 g, 7 g and 9 g dose equivalent to the sodium oxybate salt. The compositions were administered two hours after the start of a high-fat, high calorie breakfast.

The PK data is presented in FIGS. 20A and 20B. The mean PK parameters for the dose escalation study are presented in Table 11.

TABLE 11

Mean PK Parameters for 'DR2' Dose Escalation Study

| Dose (g) | N | Cmax (ng/mL) | Tmax (h) | AUC0-t (ug * h/mL) | AUC0-inf (ug * h/mL) | T1/2 (h) | C8h (ug/mL) |
|---|---|---|---|---|---|---|---|
| 4.5 | 12 | 40.6 (27.6) | 2.02 (0.25-4.00) | 142 (38.2) | 148 (36.4) (N = 11) | 0.613 (17.8) (N = 11) | 1.19 (180.6) |
| 7 | 12 | 75.0 (22.5) | 2.75 (0.25-4.00) | 343 (29.2) | 347 (29.4) | 0.671 (22.5) | 5.03 (137.3) |
| 9 | 9 | 104 (19.1) | 2.50 (0.50-5.00) | 537 (29.5) | 542 (29.2) | 0.724 (26.5) | 15.9 (107.3) |

(% CV) except for Tmax (Median (Range))

The data indicates that the use of pH 5.5 triggered polymer film system results in rapid oxybate release (believed to occur in the proximal small intestine). The incorporation of a pH independent polymer (ethylcellulose) extended oxybate release (likely extended into the small intestine). Both compositions dosed incorporating the DR prototypes have the same relative bioavailability to that of the reference, Xyrem® (sodium oxybate solution). Though not wishing to be bound by any one particular theory, this is indicative that oxybate release from the 'DR2' prototype was not overextended in the small intestine, with release within the target small intestinal absorption window.

Figure 21A:
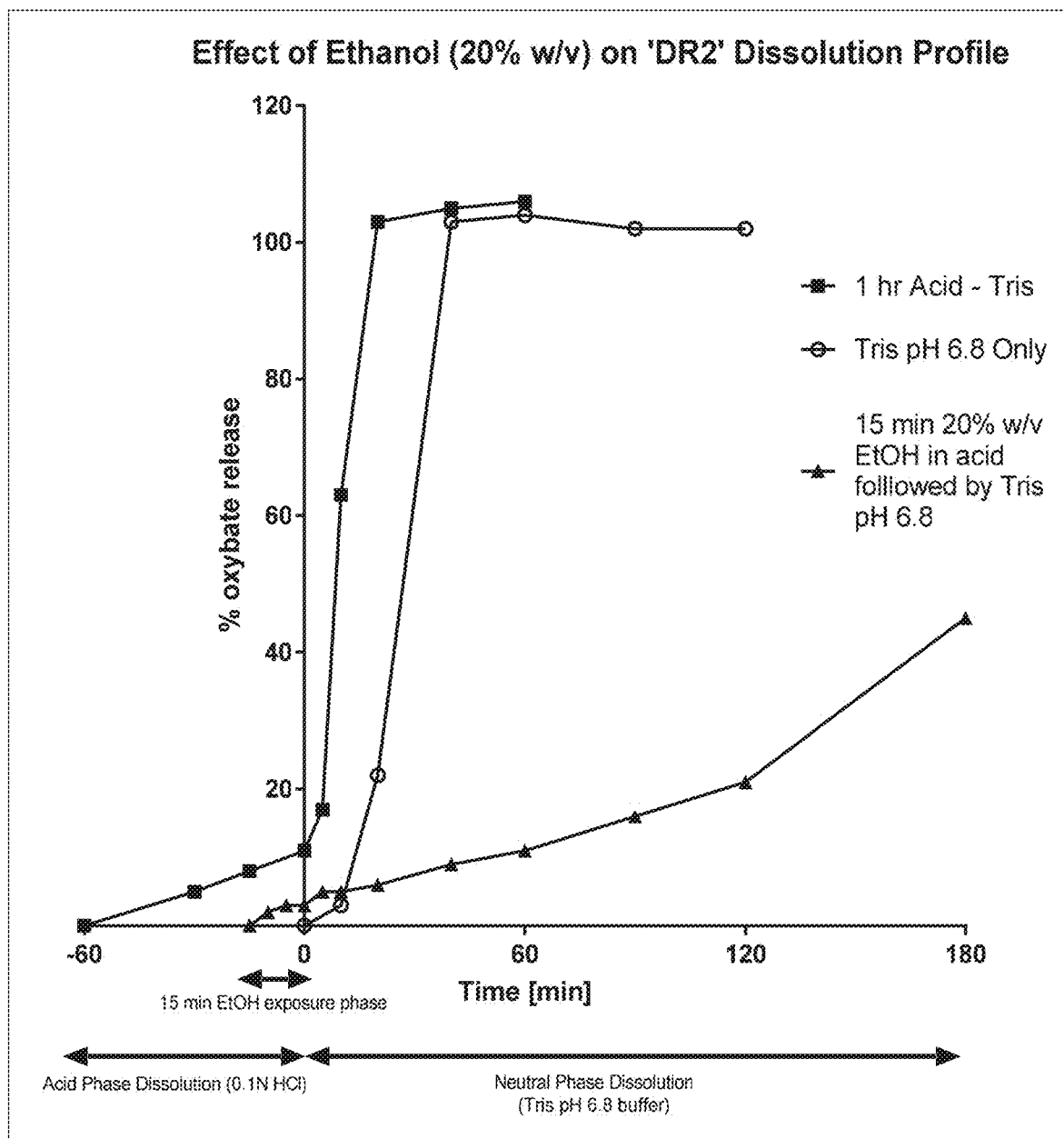
FIG. 21A is a graph comparing the dissolution in Tris pH 6.8 buffer of a binary film prototype of Example 10, 'DR2', in the absence (circles) or presence (triangles) of a 15 minute pre-exposure to 0.1N HCl containing 20% v/v ethanol (note: only the modified release component having the inner and outer binary polymer film coatings was tested).
Figure 21B:
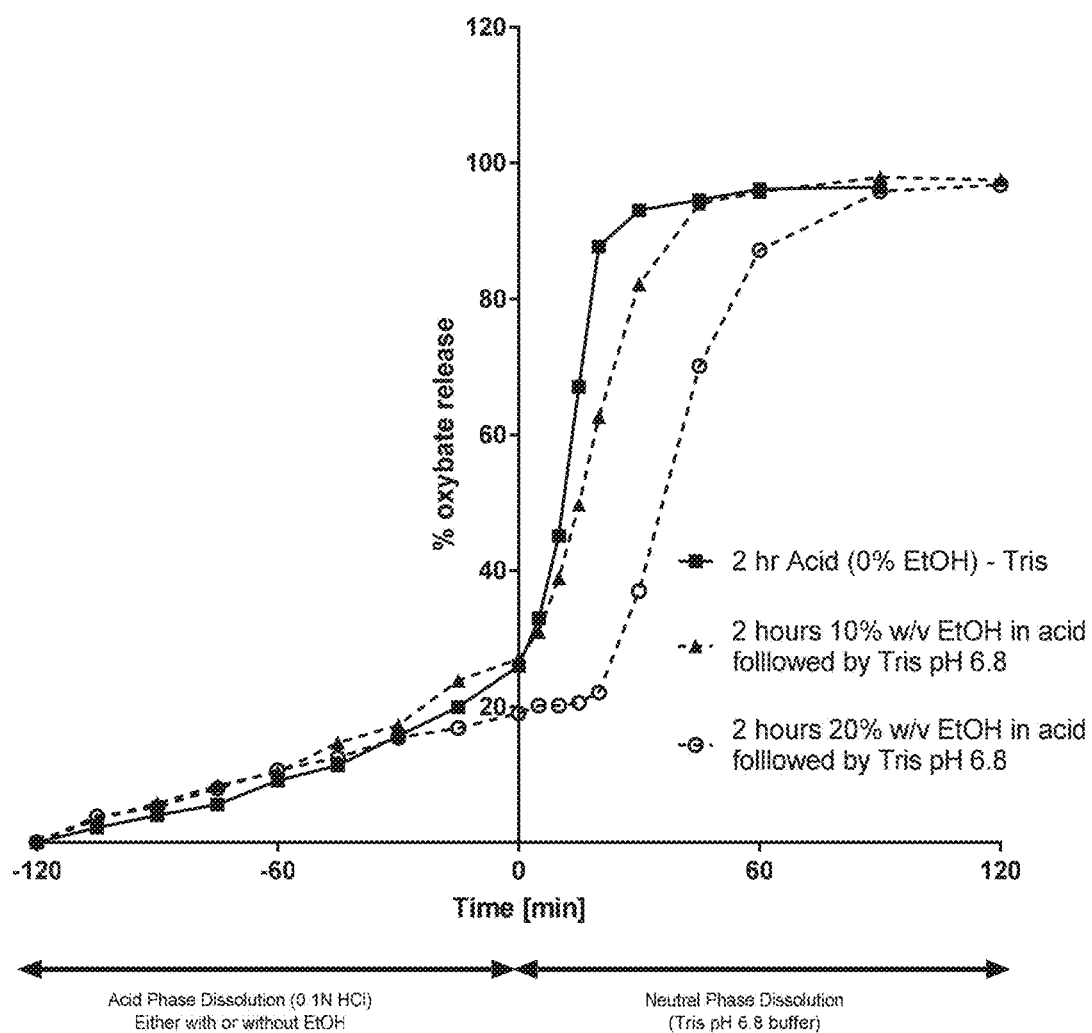
FIG. 21B is a graph presenting the dissolution of a binary polymer film prototype of Example 10, 'DR2', in the presence and absence of EtOH for up to 2 hours in the acid phase, (note: only the modified release component having the inner and outer binary polymer film coatings was tested). The effect of 2 hours EtOH exposure on subsequent oxybate release rate in Tris pH 6.8 buffer is shown.

The effect of 15 minute exposure to 20% v/v ethanol in acid (0.1N HCl) on the resultant dissolution profile of the binary polymer film 'DR2' prototype in Tris pH 6.8 buffer is presented in FIG. 21. It can be seen that exposure to ethanol results in a significant slowing of oxybate dissolution from the coated pellet.

Example 11

Application of Ethylcellulose-Methacrylic Acid Ethylacrylate 1:1 Co-Polymer Binary Polymer Film to Codeine Phosphate Pellet Cores Multi-particulate (pellet) drug carrier cores of codeine phosphate were made by the process of extrusion-spheronisation. The core composition is provided in Table 11. Core components are weighed and then added to the mixing bowl of a Caleva Multi-lab. The excipients (MCC, lactose, LHPC, and HPC) were pre-blended for ca. 3 min. The codeine phosphate was then added and blended for a further 5 min. Water was added to the mixed dry components until a wet mass was formed. The wet mass was extruded (die plate diameter of 0.8 mm). The extrudate was then spheronized and dried to form the pellet core.

TABLE 11

Composition of the codeine phosphate drug carrier (pellet) core

| Component | Quantity (% w/w) |
|---|---|
| Codeine phosphate | 10.0 |
| Lactose (monohydrate) | 41.0 |
| Microcrystalline cellulose | 41.0 |
| Hydroxypropyl cellulose | 5.0 |
| Low-substituted hydroxypropyl cellulose | 3.0 |
| Water* | q.s |

The pellets were oven dried and then screened 0.8 mm-1.25 mm. 1002451A binary polymer film coat consisting ethylcellulose (as the 30% aqueous dispersion, Aquacoat® ECD) and methacrylic acid-ethylacrylate 1:1 copolymer (as Eudragit® L30D-55) was applied to the codeine phosphate pellet cores at varying film thickness. The polymer film was prepared as an aqueous dispersion with polymer ratio of 1:1 (based on % w/w dry polymer) and applied as droplets to the pellet using an atomizing spray gun in a fluid bed coating unit (Calva Mini-Coater). The coated pellets were cured under controlled temperature and humidity conditions. The binary polymer film was applied as a single coat. Samples were prepared having 15, 22 and 30% w/w (% w/w of the codeine phosphate pellet core) binary polymer film composition to evaluate the effect of the coating film thickness on in-vitro dissolution characteristics in the presence and absence of ethanol (EtOH).

Figure 22:
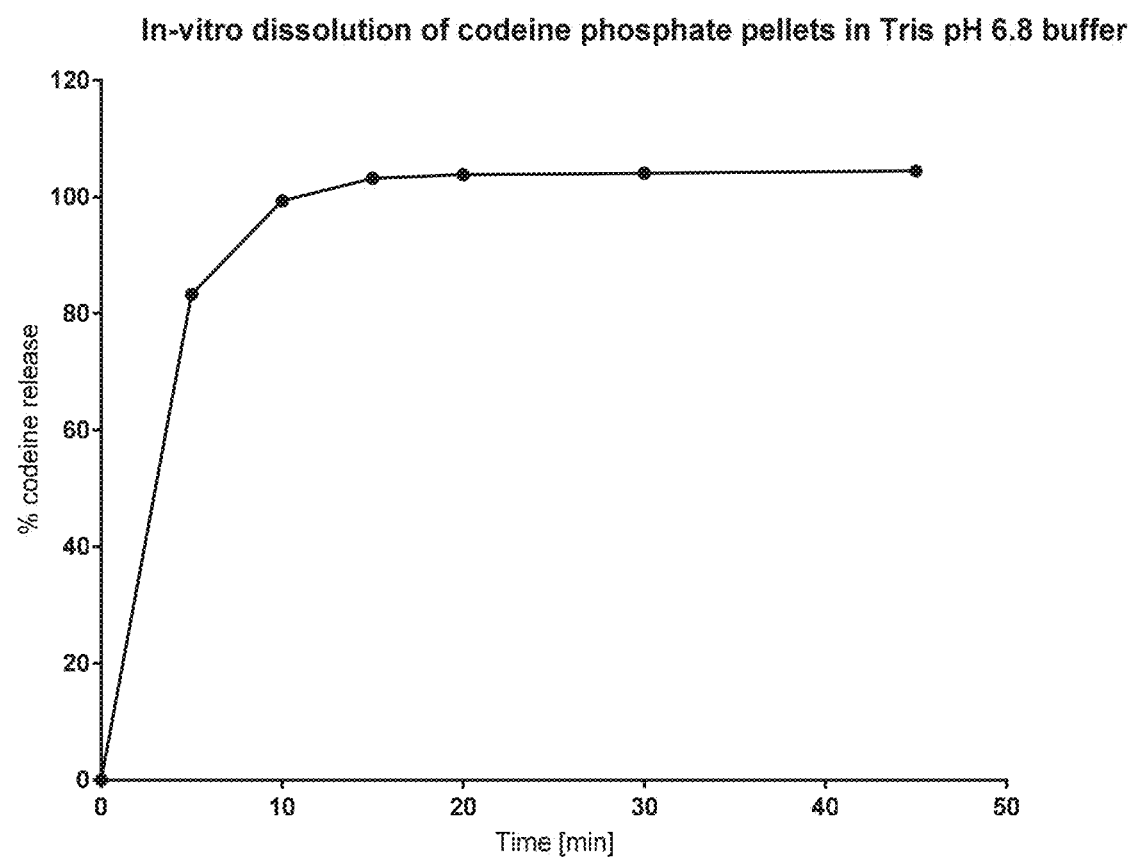
FIG. 22 is a graph showing the in vitro dissolution profile of codeine phosphate from a pellet core when prepared with a binary film coating and when dissolution was tested for 45 minutes in Tris pH 6.8 buffer.

FIG. 22 presents data generated for in-vitro dissolution testing of the codeine phosphate pellet core. The dissolution test was performed using USP II apparatus (paddles) with 300 mL Tris buffer pH 6.8 (37° C., 100 rpm).

Figure 23:
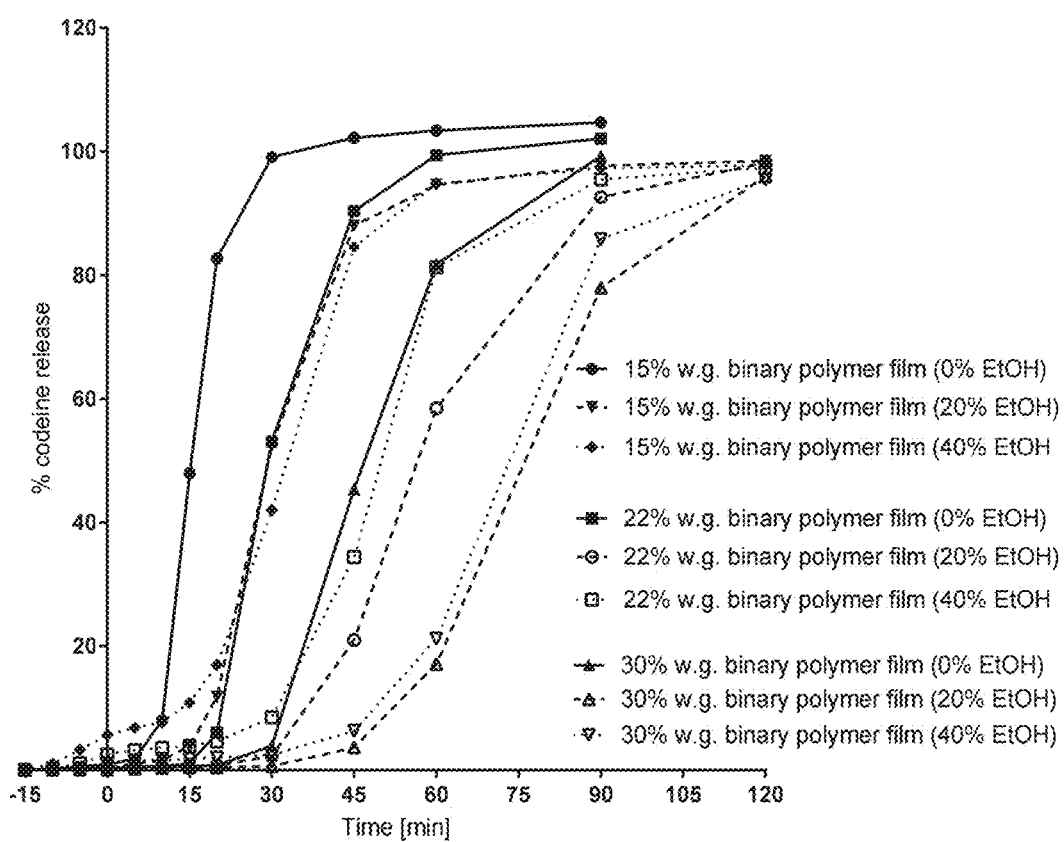
FIG. 23 is a graph showing the impact of polymer film coating thickness on the in vitro dissolution profile of codeine phosphate from a pellet core using three different thicknesses, equivalent to 15% w/w polymer, 22% w/w polymer and 30% w/w polymer of the uncoated codeine phosphate pellet core, dissolution was tested for 15 minutes in acid (0.1N HCl) followed by between 90 to 120 minutes in Tris pH 6.8 buffer and tested in the presence and absence of 20% v/v and 40% v/v ethanol in the 15 minute acid phase.

FIG. 23 presents data for two-stage in-vitro dissolution testing of the binary film coated codeine phosphate pellets. The dissolution test was performed using USP II apparatus (paddles) with 300 mL of 0.1N HCl (15 minutes) followed by 300 mL of Tris buffer pH 6.8 (37° C., 100 rpm) for between 90 and 120 minutes. At all polymer film thicknesses investigated, codeine phosphate release is significantly suppressed in acid. The lag in codeine phosphate release in the Tris pH 6.8 buffer is extended with increasing polymer film thickness. In-vitro dissolution data is also presented following 15 minute pre-exposure of the coated codeine phosphate pellets to 0.1N HCl containing 20% v/v or 40% v/v EtOH. Codeine phosphate dissolution rate following subsequent transfer of the EtOH exposed coated pellets to Tris pH 6.8 buffer is suppressed for between approx. 10-15 minutes, depending on the polymer film thickness.

Figure 24:
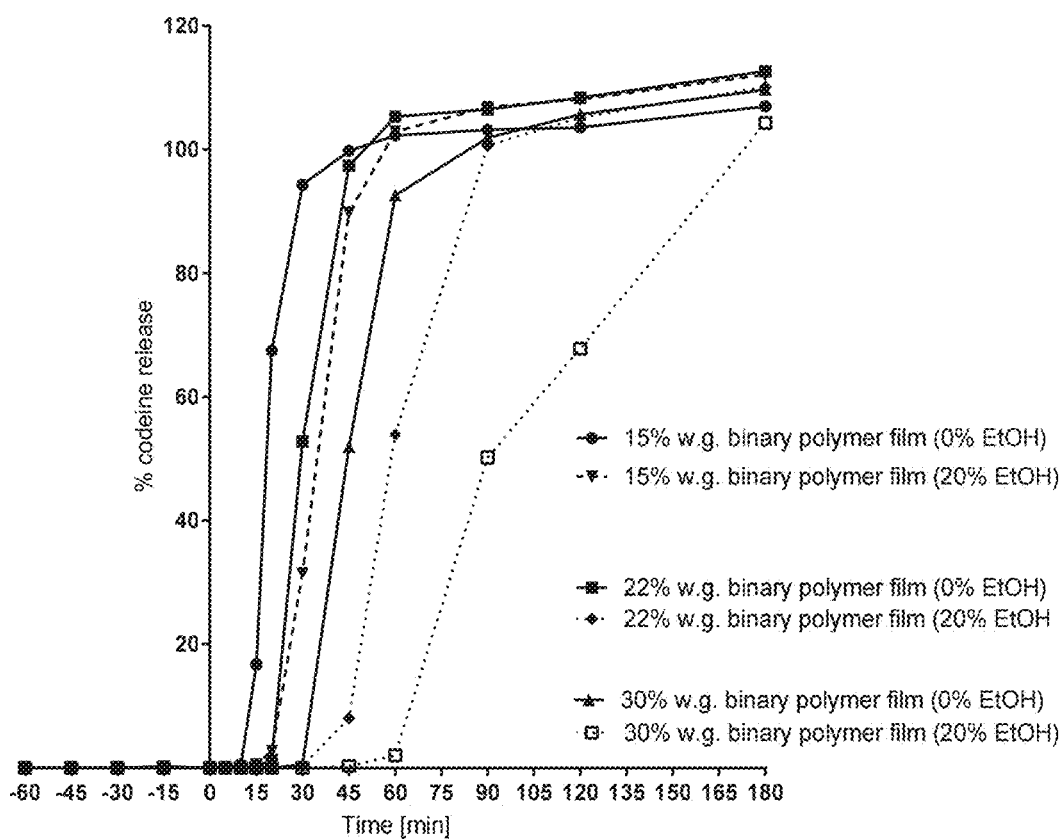
FIG. 24 is a graph showing the impact of polymer film coating thickness on the in vitro dissolution profile of codeine phosphate from a pellet core following the application of a polymer film coat consisting of a 1:1 mixture of ethylcellulose and poly(methacrylic acid-ethyl acrylate co-polymer using three different thicknesses, equivalent to 15% w/w polymer, 22% w/w polymer and 30% w/w polymer of the uncoated codeine phosphate pellet core, dissolution was tested for 60 minutes exposure of the composition to 20% v/v EtOH in acid (0.1 N HCl), with impact of EtOH exposure on in vitro dissolution rate in neutral pH buffer discerned by subsequently testing the composition in Tris pH 6.8 buffer.

FIG. 24 presents data for two-stage in-vitro dissolution testing of the binary film coated codeine phosphate pellets following 60 minutes exposure to 0.1 N HCl containing 20% v/v EtOH. Rapid release of codeine phosphate was not triggered in the presence of 20% v/v EtOH. Codeine phosphate dissolution rate following subsequent transfer of the EtOH exposed coated pellets to Tris pH 6.8 buffer is suppressed for up to 30 minutes, depending on the polymer film thickness.

Example 11

Impact of Guar Gum Containing 'Top Coat' on Codeine Phosphate Release from Binary Polymer Film Coated Pellets Codeine phosphate pellet cores were made by wet mass extrusion-spheronisation as described in Example 1. An aqueous dispersion of ethylcellulose and methacrylic acid-ethylacrylate 1:1 co-polymer was prepared using Aquacoat® ECD and Eudragit® L30D-55 respectively. The polymers were used at a 1:1 ratio (based on % w/w dry polymer) and the dispersion applied to the codeine phosphate pellets using a fluid bed coating process as described in Example 1. In one embodiment, the polymer suspension was applied to a target 30% polymer weight gain (% w/w of the drug carrier core). In another embodiment, the polymer suspension was applied to a target 40% polymer weight gain (% w/w of the drug carrier core). An additional polymer film layer incorporating the polysaccharide guar gum ("GG") was applied to each of the embodiments (i.e. the codeine pellets having either a 30% or 40% weight gain binary polymer coating) to a target 5% polymer weight gain (% w/w of the drug carrier pellet having the first polymer coat applied). This outer polymer film top coat was prepared as an aqueous dispersion of Aquacoat® ECD and Eudragit L30D-55 (1:1 dry polymer ratio) with guar gum at a level of 10% w/w of the EC polymer content. 'Single coated' codeine phosphate pellets having just the inner binary polymer film coating were compared to the 'double coated' codeine phosphate pellets having the additional outer guar gum containing polymer film coating.

The two-phase in vitro dissolution of codeine phosphate from the coated pellets was determined using USP apparatus II (paddles) with 300 mL acid (0.1N HCl) medium for the first phase followed by 300 mL Tris buffer pH 6.8 for the second dissolution phase (37° C., 100 RPM). Pellets with and without the outer GG polymer coat were exposed to the acid phase for 1 hour followed by 4 hours exposure to the neutral Tris buffer. Ethanol was added to the acid phase at either 20% v/v or 40% v/v.

The graph in FIG. 25 shows the dissolution profiles generated for the coated codeine phosphate pellets having 30% weight gain inner binary polymer film coating under such test conditions. No codeine phosphate release was detected in the acid phase dissolution test, including upon incorporation of 20% v/v EtOH for up to 2 hours. The impact of varying EtOH concentration and exposure time during the acid-phase dissolution on subsequent dissolution characteristics in Tris pH 6.8 buffer is was determined. Increasing the EtOH concentration from 10% v/v to 20% v/v results in more prolonged suppression of codeine release in the Tris pH 6.8 buffer.

The graph in FIG. 26 shows the dissolution profiles generated for the coated codeine phosphate pellets having 40% weight gain inner binary polymer film coating under such test conditions. The application of the second coat results in more prolonged suppression of codeine release in the presence of ethanol.

Example 12

Application of Ethylcellulose-Methacrylic Acid Ethylacrylate 1:1 Co-Polymer Binary Polymer Film to Codeine Phosphate Tablet Cores Codeine phosphate tablets were prepared by direct compression of a powder blend of codeine phosphate, Ludipress® and magnesium stearate (Table 12). All components were mixed manually for 15 minutes in a glass vial. Tablets were produced using a laboratory tablet press (Gamlen Tablet Press, Gamlen Tableting, UK) equipped with 5 mm round flat-faced tablet tools. Tablet blend was compressed using a pressure of 74.98 MPa (corresponding to a compression load of 150 Kg).

TABLE 12

Composition of the codeine phosphate drug carrier (tablet) core

| Component | Quantity (% w/w) |
| --- | --- |
| Codeine phosphate | 50.0 |
| Ludipress ® | 49.5 |
| Magnesium stearate | 0.5 |

A binary polymer film consisting ethylcellulose (as the 30% aqueous dispersion, Aquacoat® ECD) and methacrylic acid-ethylacrylate 1:1 co-polymer (as Eudragit® L30D-55) was applied to the codeine phosphate tablet cores at varying film thickness. The polymer film was prepared as an aqueous dispersion with polymer ratio of 1:1 (based on % w/w dry polymer) and applied as droplets to the tablet using an atomizing spray gun in a fluid bed coating unit (Calva Mini-Coater). The coated tablets were cured under controlled temperature and humidity conditions. The binary polymer film was applied as a single coat. Samples were prepared having 5 and 10% w/w (% w/w of the codeine phosphate tablet core) binary polymer film composition to evaluate the effect of the coating film thickness on in-vitro dissolution characteristics in the presence and absence of ethanol (EtOH).

FIG. 27 presents data generated for in-vitro dissolution testing of the codeine phosphate tablet core. The dissolution test was performed using USP II apparatus (paddles) with 300 mL Tris buffer pH 6.8 (37° C., 100 rpm).

FIG. 28 presents data for two-stage in-vitro dissolution testing of the binary film coated codeine phosphate tablets. The dissolution test was performed using USP II apparatus (paddles) with 300 mL of 0.1N HCl followed by 300 mL of Tris buffer pH 6.8 (37° C., 100 rpm). At both polymer film thicknesses investigated, codeine phosphate release is significantly suppressed in acid. The lag in codeine phosphate release in the Tris pH 6.8 buffer is extended with increasing polymer film thickness. In-vitro dissolution data is also presented following 15 minute pre-exposure of the coated codeine phosphate tablets to 0.1N HCl containing 20% v/v EtOH. Codeine phosphate dissolution rate is shown to be reduced following subsequent transfer of the EtOH exposed coated pellets to Tris pH 6.8 buffer.

Example 13

Application of ethylcellulose-methacrylic acid ethylacrylate 1:1 co-Polymer Binary Polymer Film To Oxycodone Hydrochloride Pellet Cores Multi-particulate (pellet) drug carrier cores of oxycodone hydrochloride were made by the process of extrusion-spheronisation. The core composition is provided in Table 13. The dry excipient components, namely microcrystalline cellulose (MCC), lactose monohydrate, low-substituted hydroxypropyl cellulose (L-HPC), and hydroxyl propyl cellulose (HPC), were pre-blended in the mixing bowl of a Calvea Multi-lab for approximately 5 minutes before adding the oxycodone hydrochloride and blending for an additional approximately 5 minutes. Water was added to produce a wet mass suitable for extrusion and spheronisation, producing spherical pellets. The wet mass was extruded (Caleva Mini-lab) through a die plate of 0.8 mm diameter and spheronized. The pellets were dried and screened, with pellets between 0.8 mm-1.25 mm used for coating.

TABLE 13

Composition of the oxycodone hydrochloride drug carrier (pellet) core

| Component | Quantity (% w/w) |
| --- | --- |
| Oxycodone hydrochloride | 10.0 |
| MCC | 41.0 |
| Lactose monohydrate | 41.0 |
| L-HPC | 3.0 |
| HPC | 5.0 |

A binary polymer film consisting ethylcellulose (as the 30% aqueous dispersion, Aquacoat® ECD) and methacrylic acid-ethylacrylate 1:1 co-polymer (as Eudragit® L30D-55) was applied to the oxycodone hydrochloride pellet cores at varying film thickness. The polymer film was prepared as an aqueous dispersion with polymer ratio of 1:1 (based on % w/w dry polymer) and applied as droplets to the tablet using an atomizing spray gun in a fluid bed coating unit (Calva Mini-Coater). The coated tablets were cured under controlled temperature and humidity conditions. The binary polymer film was applied as a single coat. Samples were prepared having 15%, 22% and 30% w/w (% w/w of the codeine phosphate tablet core) binary polymer film composition to evaluate the effect of the coating film thickness on in-vitro dissolution characteristics in the presence and absence of ethanol (EtOH).

FIG. 29 presents data generated for in-vitro dissolution testing of the oxycodone hydrochloride pellet core. The dissolution test was performed using USP II apparatus (paddles) with 300 mL Tris buffer pH 6.8 (37° C., 100 rpm).

FIG. 30 presents data for two-stage in-vitro dissolution testing of the binary film coated oxycodone hydrochloride pellets. The dissolution test was performed using USP II apparatus (paddles) with 300 mL of 0.1N HCl followed by 300 mL of Tris buffer pH 6.8 (37° C., 100 rpm). At all polymer film thicknesses investigated, oxycodone hydrochloride release is significantly suppressed in acid. The lag in oxycodone hydrochloride release in the Tris pH 6.8 buffer is extended with increasing polymer film thickness. In-vitro dissolution data is also presented following 15 minute pre-exposure of the coated oxycodone hydrochloride pellets to 0.1N HCl containing 20% v/v EtOH. Oxycodone hydrochloride dissolution rate following subsequent transfer of the EtOH exposed coated pellets to Tris pH 6.8 buffer is suppressed for between approx. 10-30 minutes, depending on the polymer film thickness.

Example 14: Impact of guar gum containing 'top coat' on oxycodone hydrochloride release from binary polymer film coated pellets Codeine phosphate pellet cores were made by wet mass extrusion-spheronisation as described in Example 4. An aqueous dispersion of ethylcellulose and methacrylic acid-ethylacrylate 1:1 co-polymer was prepared using Aquacoat® ECD and Eudragit® L30D-55 respectively. The polymers were used at a 1:1 ratio (based on % w/w dry polymer) and the dispersion applied to the oxycodone hydrochloride pellets using a fluid bed coating process as described in Example 4. The polymer suspension was applied to a target 30% polymer weight gain (% w/w of the drug carrier core). An additional polymer film layer incorporating the polysaccharide guar gum ("GG") was applied to the coated pellets (i.e. the oxycodone pellets having a 30% weight gain binary polymer coating) to a target 5% polymer weight gain (% w/w of the drug carrier pellet having the first polymer coat applied). This outer polymer film top coat was prepared as an aqueous dispersion of Aquacoat® ECD and Eudragit L30D-55 (1:1 dry polymer ratio) with guar gum at a level of 10% w/w of the EC polymer content. 'Single coated' oxycodone HCl pellets having just the inner binary polymer film coating were compared to the 'double coated' oxycodone HCl pellets having the additional outer guar gum containing polymer film coating.

The two-phase in vitro dissolution of oxycodone HCl from the coated pellets was determined using USP apparatus II (paddles) with 300 mL acid (0.1N HCl) medium for the first phase followed by 300 mL Tris buffer pH 6.8 for the second dissolution phase (37° C., 100 RPM). Pellets with and without the outer GG polymer coat were exposed to the acid phase for 1 hour followed by 3 hours exposure to the neutral Tris buffer. Ethanol was added to the acid phase at 20% v/v. The graph in FIG. 31 shows the dissolution profiles generated for the coated oxycodone HCl pellets under such test conditions.

Example 15

Application of Ethylcellulose-Methacrylic Acid Ethylacrylate 1:1 Co-Polymer Binary Polymer Film to Oxycodone Hydrochloride Tablet Cores Oxycodone hydrochloride tablets were prepared by direct compression of a powder blend of oxycodone hydrochloride, Ludipress® and magnesium stearate (Table 14). All components were mixed manually for 15 minutes in a glass vial. Tablets were produced using a laboratory tablet press (Gamlen Tablet Press, Gamlen Tableting, UK) equipped with 5 mm round flat-faced tablet tools. Tablet blend was compressed using a pressure of 74.98 MPa (corresponding to a compression load of 150 Kg).

TABLE 14

Composition of the oxycodone hydrochloride drug carrier (tablet) core

| Component | Quantity (% w/w) |
| --- | --- |
| Oxycodone hydrochloride | 50.0 |
| Ludipress ® | 49.5 |
| Magnesium stearate | 0.5 |

A binary polymer film consisting ethylcellulose (as the 30% aqueous dispersion, Aquacoat® ECD) and methacrylic acid-ethylacrylate 1:1 co-polymer (as Eudragit® L30D-55) was applied to the oxycodone HCl tablet cores at varying film thickness. The polymer film was prepared as an aqueous dispersion with polymer ratio of 1:1 (based on % w/w dry polymer) and applied as droplets to the tablet using an atomizing spray gun in a fluid bed coating unit (Calva Mini-Coater). The coated tablets were cured under controlled temperature and humidity conditions. The binary polymer film was applied as a single coat. Samples were prepared having 10 and 20% w/w (% w/w of the oxycodone HCl tablet core) binary polymer film composition to evaluate the effect of the coating film thickness on in-vitro dissolution characteristics in the presence and absence of ethanol (EtOH).

FIG. 32 presents data generated for in-vitro dissolution testing of the oxycodone HCl tablet core. The dissolution test was performed using USP II apparatus (paddles) with 300 mL Tris buffer pH 6.8 (37° C., 100 rpm).

FIG. 33 presents data for two-stage in-vitro dissolution testing of the binary film coated oxycodone HCl tablets. The dissolution test was performed using USP II apparatus (paddles) with 300 mL of 0.1N HCl followed by 300 mL of Tris buffer pH 6.8 (37° C., 100 rpm). At both polymer film thicknesses investigated, oxycodone HCl release is significantly suppressed in acid. The lag in oxycodone release in the Tris pH 6.8 buffer is extended with increasing polymer film thickness. In-vitro dissolution data is also presented following 60 minute pre-exposure of the coated codeine phosphate tablets to 0.1N HCl containing 20% v/v EtOH. No increase in oxycodone release was detected during exposure to 20% v/v EtOH. Upon subsequent transfer of the tablets to non-EtOH containing Tris pH 6.8 buffer, oxycodone dissolution rate is shown to be slightly reduced for the tablet having 10% w/w polymer film coating, with the thicker 20% w/w polymer film coating generating an approx. further 30 min extension to the lag in oxycodone release upon transfer to Tris buffer (from 90 min to 120 min).

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

The invention claimed is:

1. A pharmaceutical formulation comprising a film coated drug carrier core, wherein the drug carrier core comprises gamma hydroxybutyrate (GHB) or a pharmaceutically acceptable salt thereof, and wherein the film coating comprises a polymer blend of cellulose and polymethacrylate polymer disposed over the drug carrier core;
wherein the polymer blend comprises at least two alcohol-soluble polymers; at least one alcohol-soluble polymer and at least one alcohol-insoluble polymer; or at least two alcohol-insoluble polymers;
wherein the polymer blend provides an enteric dissolution; and
wherein the release rate of the GHB or a pharmaceutically acceptable salt thereof from the formulation in a second stage of a two-stage dissolution test is decreased after the formulation is exposed to about 5% to about 40% v/v ethanol in a first stage as compared to the release rate of the therapeutic agent from the formulation in the second stage when the formulation is not exposed to ethanol in the first stage; wherein the first stage of the two-stage dissolution test is in 0.1N HCl buffer and the second stage is in Tris pH 6.8 buffer.

2. A method of treatment or prophylaxis of a disease, disorder or symptom comprising administration of a formulation of claim 1 to a patient in need thereof, wherein the disease, disorder or symptom is selected from the group consisting of sleeping disorders, drug abuse, alcohol and/or opiate withdrawal, a reduced level of growth hormone, anxiety, analgesia, effects in certain neurological disorders, Parkinson's Disease, depression, fibromyalgia, endocrine disturbances and tissue protection following hypoxia/anoxia, stroke, myocardial infarction, an increased level of intracranial pressure, excessive daytime sleepiness, cataplexy, sleep paralysis, apnea, narcolepsy, sleep time disturbances, rapid eye movement (REM) sleep behavior disorder (RBD), hypnagogic hallucinations, sleep arousal, insomnia, idiopathic hypersomnia, essential tremor and nocturnal myoclonus.

3. A pharmaceutical formulation comprising a film coated drug carrier core, wherein the drug carrier core comprises gamma hydroxybutyrate (GHB) or a pharmaceutically acceptable salt thereof, and wherein the film coating comprises a polymer blend of cellulose and polymethacrylate polymer disposed over the drug carrier core;
wherein the polymer blend comprises at least two alcohol-soluble polymers; at least one alcohol-soluble polymer and at least one alcohol-insoluble polymer; or at least two alcohol-insoluble polymers;
wherein the polymer blend provides an enteric dissolution; and
wherein not more than 0% to about 40% of the GHB or a pharmaceutically acceptable salt thereof is released from the formulation within about 1 hour of exposure to an acidic aqueous buffer comprising about 5% v/v to about 20% v/v ethanol.

4. A pharmaceutical formulation comprising a film coated drug carrier core, wherein the drug carrier core comprises gamma hydroxybutyrate (GHB) or a pharmaceutically acceptable salt thereof, and wherein the film coating comprises a polymer blend of cellulose and polymethacrylate polymer disposed over the drug carrier core;
wherein the polymer blend comprises at least two alcohol-soluble polymers; at least one alcohol-soluble polymer and at least one alcohol-insoluble polymer; or at least two alcohol-insoluble polymers;
wherein the polymer blend provides an enteric dissolution; and
wherein a release rate of the GHB or a pharmaceutically acceptable salt thereof from the formulation when about 5% v/v to about 35% v/v ethanol is present in 0.1 N HCl buffer dissolution media is within about 1% to about 10% of the release rate of the GHB or a pharmaceutically acceptable salt thereof from the formulation in the absence of ethanol for about 60 minutes in 0.1 N HCl buffer dissolution media.

5. The formulation of claim 1, wherein the polymer blend comprises ethyl cellulose and at least one polymethacrylate.

6. The formulation of claim 1, wherein the polymer blend comprises at least one polymer with pH-dependent dissolution and at least one polymer with pH-independent dissolution properties.

7. The formulation of claim 6, wherein the polymer with pH-independent dissolution properties is selected from the group consisting of ethyl cellulose, ethyl acrylate methyl methacrylate co-polymer, ethyl acrylate-methyl methacrylate-trimethylammonioethyl methacrylate chloride co-polymer, and combinations thereof.

8. The formulation of claim 6, wherein the polymer with pH-dependent dissolution properties is selected from the group consisting of methacrylic acid-ethyl acrylate co-polymer, methacrylic acid methyl methacrylate co-polymer, methyl acrylate-methyl methacrylate-methacrylic acid co-polymer, and combinations thereof.

9. The formulation of claim 6, wherein the polymer with pH-dependent dissolution properties is a methacrylic acid-ethyl acrylate co-polymer, and wherein the ratio of methacrylic acid to ethyl acrylate is about 1:1.

10. The formulation of claim 1, wherein the film coating is a first coating and the formulation further comprises a second coating comprising at least one polymer, wherein the second coating is disposed over the first coating.

11. The formulation of claim 10, wherein the second coating comprises a blend of at least two polymers.

12. The formulation of claim 11, wherein the blend of at least two polymers comprises ethyl cellulose and methacrylic acid-ethyl acrylate co-polymer.

13. The formulation of claim 10, wherein the second coating further comprises a polysaccharide gum selected from the group consisting of acacia gum, guar gum, tragacanth gum, xanthan gum, and mixtures thereof.

14. The formulation of claim 10, wherein the polymer in the second coating is a cellulose polymer, and wherein the second coating further comprises guar gum, which is present at 1-15% w/w of the cellulose polymer.

15. The formulation of claim 1, wherein the pharmaceutically acceptable salt of GHB is selected from the group consisting of sodium oxybate, calcium oxybate, potassium oxybate, magnesium oxybate, and combinations thereof.

16. The pharmaceutical formulation of claim 1, wherein the release rate of the GHB or a pharmaceutically acceptable salt thereof from the formulation in the second stage is decreased after the formulation is exposed to about 10% v/v ethanol in the first stage for about 15 minutes to about 30 minutes as compared to the release rate of the GHB or a pharmaceutically acceptable salt thereof from the formulation in the second stage when the formulation is not exposed to ethanol in the first stage.

17. The pharmaceutical formulation of claim 1, wherein the release rate of the GHB or a pharmaceutically acceptable salt thereof from the formulation in the second stage is decreased after the formulation is exposed to about 20% v/v ethanol in the first stage for about 15 minutes to about 120 minutes as compared to the release rate of the GHB or a pharmaceutically acceptable salt thereof from the formulation in the second stage when the formulation is not exposed to ethanol in the first stage.

18. The pharmaceutical formulation of claim 4, wherein the release rate of the GHB or a pharmaceutically acceptable salt thereof from the formulation when about 5% v/v to about 20% v/v ethanol is present in the dissolution media is within about 1% to about 10% of the release rate of the GHB or a pharmaceutically acceptable salt thereof from the formulation in the absence of ethanol for about 1 hour to about 2 hours when tested in 0.1N HCl.

19. A pharmaceutical formulation comprising a film coated drug carrier core, wherein the drug carrier core comprises gamma hydroxybutyrate (GHB) or a pharmaceutically acceptable salt thereof, and wherein the film coating comprises a polymer blend of cellulose and polymethacrylate polymer disposed over the drug carrier core;
wherein the polymer blend comprises at least two alcohol-soluble polymers; at least one alcohol-soluble polymer and at least one alcohol-insoluble polymer; or at least two alcohol-insoluble polymers; and
wherein the polymethacrylate polymer in the polymer blend is methacrylic acid-ethyl acrylate co-polymer, methacrylic acid methyl methacrylate co-polymer, or methyl acrylate-methyl methacrylate-methacrylic acid co-polymer.

20. A pharmaceutical formulation comprising a film coated drug carrier core, wherein the drug carrier core comprises gamma hydroxybutyrate (GHB) or a pharmaceutically acceptable salt thereof, and wherein the film coating comprises a polymer blend of cellulose and polymethacrylate polymer at a weight ratio of about 1:3 to about 3:1 disposed over the drug carrier core; and
wherein the polymethacrylate polymer in the polymer blend is methacrylic acid-ethyl acrylate co-polymer, methacrylic acid methyl methacrylate co-polymer, or methyl acrylate-methyl methacrylate-methacrylic acid co-polymer.

21. The pharmaceutical formulation of claim 20, wherein the release rate of the GHB or a pharmaceutically acceptable salt thereof from the formulation in a second stage of a two-stage dissolution test is decreased after the formulation is exposed to about 5% to about 40% v/v ethanol in a first stage as compared to the release rate of the GHB or a pharmaceutically acceptable salt thereof from the formulation in the second stage when the formulation is not exposed to ethanol in the first stage; wherein the first stage of the two-stage dissolution test is in 0.1N HCl buffer and the second stage is in Tris pH 6.8 buffer.

22. The pharmaceutical formulation of claim 20, wherein not more than 0% to about 40% of the GHB or a pharmaceutically acceptable salt thereof is released from the formulation within about 1 hour of exposure to an acidic aqueous buffer comprising about 5% v/v to about 20% v/v ethanol.

23. The pharmaceutical formulation of claim 20, wherein a release rate of the GHB or a pharmaceutically acceptable salt thereof from the formulation when about 5% v/v to about 35% v/v ethanol is present in 0.1 N HCl buffer dissolution media is within about 1% to about 10% of the release rate of the GHB or a pharmaceutically acceptable salt thereof from the formulation in the absence of ethanol for about 60 minutes in 0.1 N HCl buffer dissolution media.

24. The pharmaceutical formulation of claim 20, wherein the pharmaceutically acceptable salt of GHB is selected from the group consisting of sodium oxybate, calcium oxybate, potassium oxybate, magnesium oxybate, and combinations thereof.

25. The formulation of claim 20, wherein the polymer blend comprises ethyl cellulose.

26. The formulation of claim 20, wherein the polymer blend comprises methacrylic acid-ethyl acrylate co-polymer, and wherein the ratio of methacrylic acid to ethyl acrylate is about 1:1.

27. The formulation of claim 20, wherein the film coating is a first coating and the formulation further comprises a second coating comprising at least one polymer, wherein the second coating is disposed over the first coating.

28. The formulation of claim 27, wherein the second coating comprises ethyl cellulose and methacrylic acid-ethyl acrylate co-polymer.

29. The formulation of claim 27, wherein the second coating further comprises a polysaccharide gum selected from the group consisting of acacia gum, guar gum, tragacanth gum, xanthan gum, and mixtures thereof.

30. The formulation of claim 27, wherein the polymer in the second coating is a cellulose polymer, and wherein the second coating further comprises guar gum, which is present at 1-15% w/w of the cellulose polymer.

31. The formulation of claim 19, wherein the polymer blend comprises ethyl cellulose.

32. The formulation of claim 19, wherein the polymer blend comprises methacrylic acid-ethyl acrylate co-polymer, and wherein the ratio of methacrylic acid to ethyl acrylate is about 1:1.

33. The formulation of claim 19, wherein the film coating is a first coating and the formulation further comprises a second coating comprising at least one polymer, wherein the second coating is disposed over the first coating.

34. The formulation of claim 33, wherein the second coating comprises ethyl cellulose and methacrylic acid-ethyl acrylate co-polymer.

35. The formulation of claim 33, wherein the polymer in the second coating is a cellulose polymer, and wherein the second coating further comprises guar gum, which is present at 1-15% w/w of the cellulose polymer.

36. The formulation of claim 3, wherein the polymer blend comprises ethyl cellulose.

37. The formulation of claim 3, wherein the polymer blend comprises methacrylic acid-ethyl acrylate co-polymer, and wherein the ratio of methacrylic acid to ethyl acrylate is about 1:1.

38. The formulation of claim 3, wherein the film coating is a first coating and the formulation further comprises a second coating comprising at least one polymer, wherein the second coating is disposed over the first coating.

39. The formulation of claim 38, wherein the second coating comprises ethyl cellulose and methacrylic acid-ethyl acrylate co-polymer.

40. The formulation of claim 38, wherein the polymer in the second coating is a cellulose polymer, and wherein the second coating further comprises guar gum, which is present at 1-15% w/w of the cellulose polymer.

41. A method of treatment or prophylaxis of a disease, disorder or symptom comprising administration of a formulation of claim 19 to a patient in need thereof, wherein the disease, disorder or symptom is selected from the group consisting of sleeping disorders, drug abuse, alcohol and/or opiate withdrawal, a reduced level of growth hormone, anxiety, analgesia, effects in certain neurological disorders, Parkinson's Disease, depression, fibromyalgia, endocrine disturbances and tissue protection following hypoxia/anoxia, stroke, myocardial infarction, an increased level of intracranial pressure, excessive daytime sleepiness, cataplexy, sleep paralysis, apnea, narcolepsy, sleep time disturbances, rapid eye movement (REM) sleep behavior disorder (RBD), hypnagogic hallucinations, sleep arousal, insomnia, idiopathic hypersomnia, essential tremor and nocturnal myoclonus.

42. A method of treatment or prophylaxis of a disease, disorder or symptom comprising administration of a formulation of claim 20 to a patient in need thereof, wherein the disease, disorder or symptom is selected from the group consisting of sleeping disorders, drug abuse, alcohol and/or opiate withdrawal, a reduced level of growth hormone, anxiety, analgesia, effects in certain neurological disorders, Parkinson's Disease, depression, fibromyalgia, endocrine disturbances and tissue protection following hypoxia/anoxia, stroke, myocardial infarction, an increased level of intracranial pressure, excessive daytime sleepiness, cataplexy, sleep paralysis, apnea, narcolepsy, sleep time disturbances, rapid eye movement (REM) sleep behavior disorder (RBD), hypnagogic hallucinations, sleep arousal, insomnia, idiopathic hypersomnia, essential tremor and nocturnal myoclonus.

43. The formulation of claim 1, wherein the film coating is disposed over the drug carrier core as an aqueous dispersion of the polymer blend.

44. The formulation of claim 3, wherein the film coating is disposed over the drug carrier core as an aqueous dispersion of the polymer blend.

45. The formulation of claim 4, wherein the film coating is disposed over the drug carrier core as an aqueous dispersion of the polymer blend.

46. The formulation of claim 19, wherein the film coating is disposed over the drug carrier core as an aqueous dispersion of the polymer blend.

47. The formulation of claim 20, wherein the film coating is disposed over the drug carrier core as an aqueous dispersion of the polymer blend.

* * * * *